US007323175B2

(12) United States Patent
Smith et al.

(10) Patent No.: US 7,323,175 B2
(45) Date of Patent: Jan. 29, 2008

(54) IMMUNOGENICITY OF GLUCAN BINDING PROTEIN

(75) Inventors: Daniel J. Smith, Natick, MA (US); Martin A. Taubman, Newtonville, MA (US)

(73) Assignee: The Forsyth Institute, Boston, MA (US)

( * ) Notice: Subject to any disclaimer, the term of this patent is extended or adjusted under 35 U.S.C. 154(b) by 314 days.

(21) Appl. No.: 10/383,930

(22) Filed: Mar. 7, 2003

(65) Prior Publication Data

US 2004/0127400 A1 Jul. 1, 2004

Related U.S. Application Data

(60) Provisional application No. 60/402,483, filed on Aug. 8, 2002, provisional application No. 60/363,209, filed on Mar. 7, 2002.

(51) Int. Cl.
*A61K 39/02* (2006.01)
*A61K 39/38* (2006.01)
*A61K 38/00* (2006.01)

(52) U.S. Cl. .............. 424/190.1; 424/9.1; 424/9.2; 424/184.1; 424/185.1; 424/193.1; 424/197.11; 424/203.1; 424/234.1; 424/244.1; 435/69.1; 435/183; 435/193; 435/253.4; 530/300; 530/350

(58) Field of Classification Search ............... 424/9.1, 424/9.2, 184.1, 185.1, 190.1, 193.1, 197.11, 424/234.1, 244.1; 435/69.1, 183, 193, 253.4; 530/300, 350
See application file for complete search history.

(56) References Cited

U.S. PATENT DOCUMENTS

| | | | | |
|---|---|---|---|---|
| 5,019,400 A | * | 5/1991 | Gombotz et al. ........... 424/497 |
| 5,223,409 A | | 6/1993 | Ladner et al. ............. 435/69.7 |
| 5,686,075 A | | 11/1997 | Taubman et al. ...... 424/197.11 |

FOREIGN PATENT DOCUMENTS

| | | |
|---|---|---|
| WO | WO90/02809 | 3/1990 |
| WO | WO91/17271 | 11/1991 |
| WO | WO92/01047 | 1/1992 |
| WO | WO92/09690 | 6/1992 |
| WO | WO92/15679 | 9/1992 |
| WO | WO92/18619 | 10/1992 |
| WO | WO92/20791 | 11/1992 |
| WO | WO93/01288 | 1/1993 |

OTHER PUBLICATIONS

Banas, et al., *Infect. Immun.*, 58(3):667-673 (1990).
Banas, et al., *FEMS Microbiol. Lett.*, 154:289-292 (1997).
Chia, et al., *Infect. Immun.*, 69(4):2493-2501 (2001).
Cole, et al., *Monoclonal Antibodies and Cancer Therapy*, pp. 77-96 (1985).
Fuchs, et al., *Biotechnology*, 9:1369-1372 (1991).
Furst, et al., *Nucleic Acids Res.*, 17(16):6724 (1989).
Galfre, et al., *Nature*, 266(5602):550-552 (1977).
GenBank Accession No. AY046410 (2001).
GenBank Accession No. AY046411 (2001).
GenBank Accession No. AY046412 (2001).
GenBank Accession No. AY046413 (2001).
GenBank Accession No. AY046414 (2001).
Griffiths, et al., *EMBO J.*, 12(2):725-734 (1993).
Hamada, et al., *Microbiol. Rev.*, 44(2):331-384 (1980).
Hay, et al., *Hum. Antibod. Hybridomas*, 3:81-85 (1992).
Higgins, et al., *CABIOS Communications*, 5(2):151-153 (1989).
Hopp, et al., *Proc. Natl. Acad. Sci. USA*, 78(6):3824-3828 (1981).
Huse, et al., *Science*, 246:1275-1281 (1989).
Keyes, et al., *Arch. Oral Biol.*, 9:377-400 (1964).
Köhler, et al., *Nature*, 266(5602):495-497 (1975).
Kolenbrander, P.E., *Annu. Rev. Microbiol.*, 54:413-437 (2000).
Lerner, E.A., *Yale J. Biol. Med.*, 54(5):387-402 (1981).
Loo, et al., *J. Bacteriol.*, 182(5):1374-1382 (2000).
Ma, et al., *Eur. J. Immunol.*, 24:131-138 (1994).
Mattos-Graner, et al., *J. Dent. Res.*, 79(6):1371-1377 (2000).
Mattos-Graner, et al., *Infect. Immun.*, 69(11):6931-6941 (2001).
Merrifield, R.B., *Synthesis of a Tetrapeptide*, 85:2149-2154 (1963).
Navarre, et al., *Mol. Microbiol.*, 14(1):115-121 (1994).
Reinscheid, et al., *J. Bacteriol.*, 183(40:1175-1183 (2001).
Russell, R.R.B., *J. Gen. Microbiol.*, 112:197-201 (1979).
Sato, et al., *Infect. Immun.*, 65(2):668-675 (1997).
Schubert, et al., *Arch. Microbiol.*, 173(1):21-28 (2000).
Smith, et al., *Oral Microbiol. Immun.*, 5(2):57-62 (1990).
Smith, et al., *Oral Microbiol. Immun.*, 13(5):278-285 (1998).
Smith, et al., *Infect. Immun.*, 62(6):2545-2552 (1994).
Smith, et al., *Infect. Immun.*, 69(5):3135-3142 (2001).
Smith, et al., *Infect. Immun.*, 69(8):4767-4773 (2001).
Smith, et al., *Infect. Immun.*, 64(8):3069-3073 (1996).
Socransky, et al., *J. Clin. Microbiol.*, 22(2):303-305 (1985).
Svendsen, et al., *Lab. Anim. Sci.*, 45(1):89-93 (1995).
Tam, J.P., *Proc. Natl. Acad. Sci. USA*, 85(15):5409-5413 (1988).
Taubman, et al., *J. Dent. Res.*, Abstract 2666, 76:347 (1997).
Van Houte, et l., *J. Dent. Res.*, 68(3):451-459 (1989).
U.S. non-published pending U.S. Appl. No. 09/562,328, by Andrew Lees, Martin A. Taubman and Daniel J. Smith, filed May 1, 2000.
U.S. Appl. No. 08/967,573, by Daniel J. Smith and Martin A. Taubman, filed Nov. 10, 1997.

* cited by examiner

*Primary Examiner*—Rodney P Swartz
(74) *Attorney, Agent, or Firm*—Mintz, Levin, Cohn, Ferris, Glovsky and Popeo, P.C.; Ingrid A. Beattie

(57) ABSTRACT

Immunogenic compositions and subunit vaccines for dental caries are described which comprise peptide subunits of glucan binding protein-B and peptide subunits of glucan binding protein-B in combination with peptide subunits of glucosyltransferase. Methods of provoking an immune response to *S. mutans* glucan binding protein-B or glucosyltransferase. Methods of immunizing a mammal against dental caries are also described, along with antibodies which bind particular epitopes of glucan binding protein-B or glucosyltransferase.

25 Claims, 12 Drawing Sheets

MAP Mono- & Di-epitopic Peptide and Protein Antigens

IMMUNOGENICITY OF GLUCAN BINDING PROTEIN

RELATED APPLICATIONS

This application claims the benefit of U.S. Provisional Application No. 60/363,209, filed Mar. 7, 2002 and U.S. Provisional Application 60/402,483, filed Aug. 8, 2002, the entire contents of which are hereby incorporated by reference.

GOVERNMENT SUPPORT

The invention was supported, in whole or in part, by a grant DE-06153 from National Institute for Dental Research. The Government has certain rights in the invention.

BACKGROUND OF THE INVENTION

*Mutans streptococci* have been implicated in the initiation of dental caries in humans. *Streptococcus mutans* have several virulence factors that allow the bacteria to accumulate within the dental biofilm and produce and tolerate the acids that cause dental caries. The ability of cariogenic *mutans streptococci* to accumulate in the dental biofilm is thought to be a consequence of the synthesis of glucans by glucosyltransferases, followed by the binding of the bacteria to these polymers via the cell-associated glucan binding proteins (Gbps). Biofilm development occurs in two distinct phases. During the first phase, bacterial surface proteins interact with host or bacterial products adsorbed on the tooth surface. In the second phase, a biofilm forms as bacteria accumulate by aggregation with the same or other species and produce an extracellular polysaccharide matrix.

Epitopes associated with these functions are thought to be primary targets for immunogenic attack, provided that the relevant sequences are located in molecular areas that can be accessible to antibody. Several *mutans streptococcal* proteins with glucan binding activity have been described (Russell, R. R., *J. Gen. Microbiol.*, 112:197–201 (1979); Smith D. J. et al., *Infect. Immun.* 62:2545–2552 (1994); Sato, Y., et al., *Infect. Immun.*, 65:668–675 (1997)). One of these components, glucan-binding protein-B (GbpB), has been shown to induce protective immune responses against experimental dental caries following systemic or mucosal immunization (Smith D. J. et al., *Infect. Immun.* 64:3069–3073 (1996) and Smith D. J. et al., Oral Microbiol. Immunol. 13:278–285(1998)). Furthermore, there is evidence that the expression of GbpB is directly related to biofilm formation (Mattos-Graner, R.O., et al., *Infect. and Immun.* 69(11) 6931–6941(2001)). However, use of the intact GbpB protein in a vaccine may induce immunity to irrelevant or unwanted epitopes.

SUMMARY OF THE INVENTION

The invention provides improved immunogens and vaccine compositions for inducing antibody production against Streptococcal antigens. Accordingly, the invention features a composition containing a fragment of a glucan binding protein-B (GbpB), which binds to a major histocompatibility complex (MHC) class II protein, e.g., an HLA protein selected from the group consisting of DRA, DRB1, DRB2, DQA1, DQB1, DPA1, DPB1, DMA, DMB, DOA, and DOB. The GbpB protein is preferably derived from a *Streptococcus mutans* strain. For example, the Streptococcal GbpB contains an amino acid sequence selected from the group consisting of SEQ ID NO's: 29, 30, 31, 32, and 33. Preferably, the GbpB protein contains the amino acid sequence of SEQ ID NO: 29 (*S. mutans* strain SJ32)

The fragment is greater than 6 and less than 431 residues in length. For example, the fragment is less than 400 residues in length, less than 100 residues in length, or less than 50 residues in length. Preferably, the fragment is 10–25 residues in length. The fragment contains an amino acid sequence selected from the group consisting of SEQ ID NO's: 1, 2, 3, 4, 5, 6, 7, 8, 9, 10, 11, 12, 13, 14, 15, 16, 17, 18, 19, 20, 21, and 22. Preferably, the fragment contains an amino acid sequence selected from the group consisting of SEQ ID NO's: 1 and 3.

Also within the invention is a chimeric polypeptide containing a fragment of two or more streptococcal proteins. For example, the composition contains a GbpB polypeptide and a glucosyltransferase (GTF) polypeptide. The polypeptides are covalently linked. The chimeric polypeptide contains greater than two epitopes (diepitopic polypeptide), and may contain 3, 4, 5 or more epitopes (multiepitopic polypeptide). Optionally, the polypeptide contains two or more copies of a single epitope. The GbpB polypeptide preferably contains an amino acid sequence selected from the group consisting of SEQ ID NO's: 1, 2, 3, 4, 5, 6, 7, 8, 9, 10, 11, 12, 13, 14, 15, 16, 17, 18, 19, 20, 21, and 22, and the glucosyltransferase polypeptide comprises a catalytic domain of SEQ ID NO: 34, 35, 36, 37, 38, 39, or 40. Preferably, the catalytic domain contains an amino acid sequence of SEQ ID NO: 24 or 25. Alternatively (or in addition), the glucosyltransferase polypeptide contains a glucan binding domain of SEQ ID NO: 34, 35, 36, 37, 38, 39, or 40. Preferably, the glucan binding domain comprises an amino acid sequence of SEQ ID NO: 23, and the glucosyltransferase polypeptide comprises an amino acid sequence selected from the group consisting of SEQ ID NO: 23, 24, 25, 26, 27, AND 28. For example, a diepitopic polypeptide construct includes a GbpB polypeptide containing SEQ ID NO: 1 and a glucosyltransferase polypeptide containing SEQ ID NO: 23 or a GbpB polypeptide containing SEQ ID NO: 1 and a glucosyltransferase polypeptide containing SEQ ID NO: 25. The di- or multi-epitopic constructs optionally contain a peptidyl core matrix. The matrix contains one or a plurality of lysine residues.

The compositions are used to elicit production of an antibody in a mammal. The method is carried out by administering to the mammal a composition containing a MHC class II-binding fragment of GbpB or a composition containing both a GbpB polypeptide and a glucosyltransferase polypeptide. In the latter case, the amount of an anti-GbpB antibody produced by the mammal is at least 10% greater than an amount produced by a mammal immunized with a composition comprising a GbpB peptide in the absence of a GTF peptide. Anti-GbpB titers in animals immunized with a di or multi-epitopic peptide constructs are preferably at least 20%, at least 50%, at least 75%, and at least 100% greater than titers achieved in animals immunized with a mono-epitopic peptide. Similarly, anti-GTF titers in animals immunized with a di or multi-epitopic peptide constructs are preferably at least 20%, at least 50%, at least 75%, and at least 100% greater than titers achieved in animals immunized with a mono-epitopic peptide. The immunization leads to production of mucosal immunity (IgA isotype) as well as systemic immunity (e.g., IgG isotype). Also, within the invention is a substantially pure antibody produced by any of the methods described above.

The polypeptides (including antibody molecules) within the invention are substantially pure. A polypeptide is substantially pure when it is separated from those contaminants, which accompany it in its natural state (proteins and other naturally-occurring organic molecules). In the case of an antibody preparation, the antibodies are purified from other blood components such as cells and other blood proteins. Typically, the polypeptide is substantially pure when it constitutes at least 60%, by weight, of the protein in the preparation. Preferably, the protein in the preparation is at least 75%, more preferably at least 90%, and most preferably at least 99%, by weight, of the desired protein. Purity is measured by any appropriate method, e.g., column chromatography, polyacrylamide gel electrophoresis, or HPLC analysis. Accordingly, substantially pure polypeptides include synthetic polypeptides, recombinant polypeptides derived from a eucaryote but produced in E. coli or another procaryote, or in a eucaryote other than that from which the polypeptide was originally derived.

The peptides are prepared synthetically or by recombinant DNA technology. The term peptide is used interchangeably with polypeptide in the present specification to designate a series of amino acids connected one to the other by peptide bonds between the alpha-amino and alpha-carboxy groups of adjacent amino acids. Optionally, one or more peptide bonds are replaced with an alternative type of covalent bond (a "peptide mimetic") which is less susceptible to cleavage by peptidases compared to a peptide bond. Where proteolytic degradation of the peptides following injection into the subject is a problem, replacement of a particularly sensitive peptide bond with a noncleavable peptide mimetic yields a peptide mimetic, which is more stable and thus more useful as a therapeutic. Such mimetics, and methods of incorporating them into peptides, are well known in the art. Similarly, the replacement of an L-amino acid residue is a standard way of rendering the peptide less sensitive to proteolysis. Also useful are amino-terminal blocking groups such as t-butyloxycarbonyl, acetyl, theyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4,-dinitrophenyl. The polypeptides or peptides are either in their neutral (uncharged) forms or in forms which are salts, and either free of modifications such as glycosylation, side chain oxidation, or phosphorylation or containing these modifications, subject to the condition that the modification not destroy the immune stimulatory activity of the polypeptides.

Derivative peptide epitopes have an amino acid sequence, which differs from the amino acid sequence of a naturally-occurring receptor peptide. Such derivative peptides have at least 50% identity compared to a reference sequence of amino acids, e.g., a naturally-occurring glutamate receptor peptide. Preferably, a derivative is 90, 95, 98, or 99% identical to a naturally-occurring protein sequence. The derivative contains a conservative amino acid substitution. By conservative substitution is meant a replacement of an amino acid residue with another, which is biologically and/or chemically similar, e.g., one hydrophobic residue for another, or one polar residue for another. The substitutions include combinations such as Gly, Ala; Val, Ile, Leu; Asp, Glu; Asn, Gln; Ser, Thr; Lys, Arg; and Phe, Tyr. Nucleotide and amino acid comparisons described herein are carried out using the Lasergene software package (DNASTAR, Inc., Madison, Wis.). The MegAlign module used is the Clustal V method (Higgins et al., 1989, CABIOS 5(2):151–153). The parameter used is gap penalty 10, gap length penalty 10.

In addition to eliciting active immunity by immunizing a mammal with streptococcal immunogens, the method encompasses methods of conferring passive immunity. For example, antibodies produced in vitro or in vivo are purified and administered to a mammal. The antibody preparation contains antibodies, which specifically bind to streptococcal antigens such as GbpB and/or GTF. For example, the antibodies used in a passive immunization regimen were raised by immunization of a first mammal with a composition containing a purified antibody which specifically binds to an MHC class II binding fragment of GbpB or one or more of the multi-epitopic constructs described above. Following purification of the antibodies from the first animal, the antibodies are administered to a second animal. Alternatively, antibodies are produced in culture, purified, and administered to a mammal to confer passive immunity. Antibodies elicited by immunization or administered passively inhibit one or more activities, e.g., colonization, of oral Streptococci.

Other features and advantages of the invention will be apparent from the following detailed description and from the claims.

DETAILED DESCRIPTION OF THE INVENTION

Figure 1:
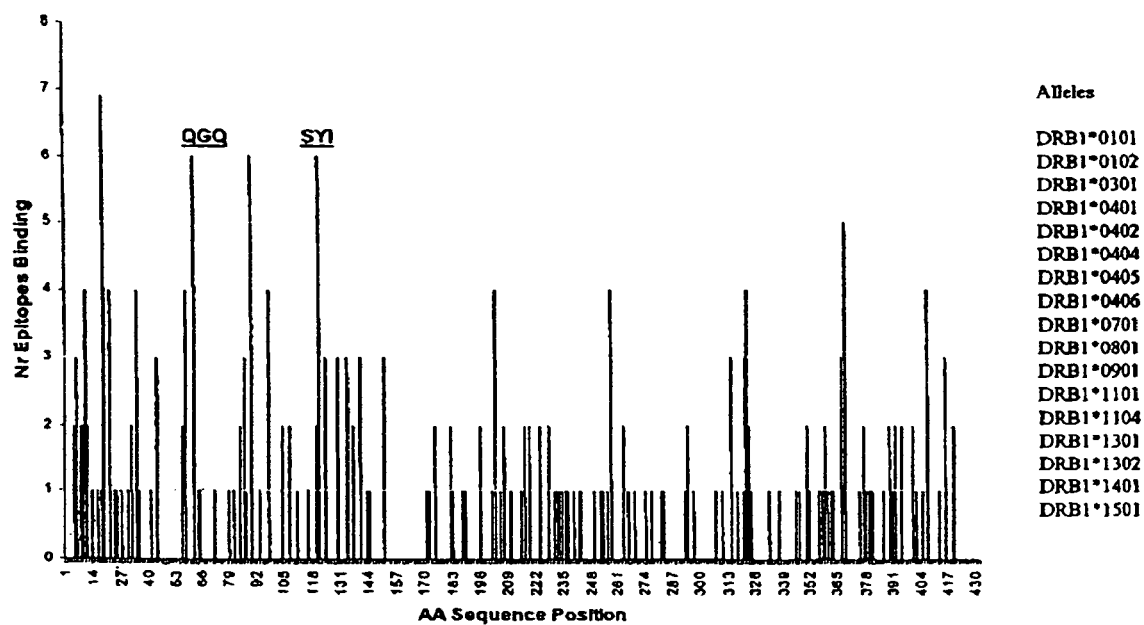
FIG. 1 is a chart depicting the results of an MHC class motif-matching algorithm used to compare GbpB primary sequence against a set of DBRI alleles represented as matches versus sequence.

*Mutans streptococcus* is the principle etiologic agent of the infectious disease dental caries. This oral pathogen infects the oral cavity during early childhood and normally remains associated with the host's dentition for life. The accumulation of bacteria within the dental biofilm is possible due to the effect of several virulence factors. The bacterial components associated with the accumulation phase of mutans streptococci include glucosyltransferases, their glucan products and glucan binding proteins. At least three *S. mutans* glucan binding proteins have been identified, GbpA, GbpB and GbpC. GbpA shares homology with the putative glucan binding domain of glucosyltransferase and the gbpA gene was found to encode a constitutively expressed secreted protein. Cell surface associated GbpC is related to the Spa family of streptococcal proteins and is only expressed during conditions of stress. GbpB is immunogenically distinct from the other glucan binding proteins expressed by *S. mutans* and *Streptococcus sobrinus* and also differs in size and purification properties.

Glucan binding protein-B is a single polypeptide chain, which is 431–432 residues in length. Analysis of the primary sequence revealed a leucine zipper domain. However, GbpB bore no sequence homology with glucan binding domains of glucosyltransferases or *S. mutans* glucan binding protein A. This prevented the specific targeting of GbpB domains of putative glucan binding function using subunit vaccine approaches that had been employed successfully with synthetic peptide or recombinant construct derived from GTF glucan binding domains as described in U.S. Pat. No. 5,686,075 and U.S. application Ser. No. 09/290,049, the entire contents of which are herein incorporated by reference.

The GbpB sequence bears significant homology with peptidoglycan hydrolases from other gram positive microorganisms, and comparative genomic analysis of the gbpB region suggested a functional relationship between genes involved in cell shape and cell wall maintenance. Attempts to knock out the gbpB gene indicated that expression of GbpB is essential for the organism. Immunogenic interference with GbpB function reduces the adverse effects associated with the growth of cariogenic *S. mutans* in the oral cavity.

Tables 5–9 include the amino acid sequence of GbpB from various strains *S. mutans*.

TABLE 5

Deduced Amino Acid Sequence of *S. mutans* strain SJ32 GbpB
GenBank accession number AY046410

MKKRILSAVLVSGVTLSSATTLSAVKADDFDAQIASQDSKINNLTAQQQA (SEQ ID NO:29)

AQAQVNTIQGQVSALQTQQAELQAENQRLEAQSATLGQQIQTLSSKIVAR

NESLKQQARSAQKSNAATSYINAIINSKSVSDAINRVSAIREVVSANEKM

LQQQEQDKAAVEQKQQENQAAINTVAANQETIAQNTNALNTQQAQLEAAQ

LNLQAELTTAQDQKATLVAQKAAAEEAARQAAAAQAAAEAKAAAEAKALQ

EQAAQAQVAANNNTQATDASDQQAAAADNTQAAQTGDSTEQSAAQAVNNS

DQESTTATEAQPSASSASTAAVAANTSSANTYPAGQCTWGVKSLAPWVGN

YWGNGGQWAASAAAAGYRVGSTPSAGAVAVWNDGGYGHVAYVTGVQGGQI

QVQEANYAGNQSIGNYRGWFNPGSVSYIYPN

TABLE 6

Deduced Amino Acid Sequence of *S. mutans* strain 3VF4 GbpB
GenBank accession number AY046411

MKKRILSAVLVSGVTLSSATTLSAVKADDFDAQIASQDSKINNLTAQQQA (SEQ ID NO:30)

AQAQVNTIQGQVSALQTQQAELQAENQRLEAQSATLGQQIQTLSSKIVAR

NESLKQQARSAQKSNAATSYINAIINSKSVSDAINRVSAIREVVSANEKM

LQQQEQDKAAVEQKQQENQAAINTVAANQETIAQNTNALNTQQAQLEAAQ

TABLE 6-continued

Deduced Amino Acid Sequence of *S. mutans* strain 3VF4 GbpB
GenBank accession number AY046411

LNLQAELTTAQDQKATLVAQKAAAEEAARQAAAAQAAAEAKAAAEAKALQ

EQAAQAQAAANNNTQATDASDQQAAAADNTQAAQTGDSTEQSAAQAVNNS

DQESTTATEAQPSASSASTAAVAANTSSANTYPAGQCTWGVKSLAPWVGN

YWGNGGQWAASAAAAGYRVGSTPSAGAVAVWNDGGYGHVAYVTGVQGGQI

QVQEANYAGNQSIGNYRGWFNPGSVSYIYPN

TABLE 7

Deduced Amino Acid Sequence of *S. mutans* strain 15JP2 GbpB
GenBank accession number AY046412

MKKRILSAVLVSGVTLSSATTLSAIKADDFDAQIASQDSKINNLTAQQQA (SEQ ID NO:31)

AQAQVNTIQGQVSALQTQQAELQAENQRLEAQSATLGQQIQTLSSKIVAR

NESLKQQARSAQKSNAATSYINAIINSKSVSDAINRVSAIREVVSANEKM

LQQQEQDKAAVEQKQQENQAAINTVAANQETIAQNTNALNTQQAQLEAAQ

LNLQAELTTAQDQKATLVAQKAAAEEAARQAAAAQAAAEAKAAAEAKALQ

EQAAQAQAAANNNTQATDASDQQAAAADNTQAAQTGDSTDQSAAQAVNN

SDQESTTATAAQPSASSASTAAVAANTSSANTYPAGQCTWGVKSLAPWVG

NYWGNGGQWAASAAAAGYRVGSTPSAGAVAVWNDGGYGHVAYVTGVQGGQ

IQVQEANYAGNQSIGNYRGWFNPGSVSYIYPN

TABLE 8

Deduced Amino Acid Sequence of *S. mutans* strain 3SN1 GbpB
GenBank accession number AY046413

MKKRILSAVLVSGVTLSSATTLSAVKADDFDAQIASQDSKINNLTAQQQA (SEQ ID NO:32)

AQAQVNTTQGQVSALQTQQAELQAENQRLEAQSATLGQQIQTLSSKIVAR

NESLKQQARSAQKSNAATSYINAIINSKSVSDAINRVSAIREVVSANEKM

LHQQEQDKAAVEQKHQENQAAINTVAANQETIAQNTNALNTQQAQLEAAQ

LNLQAELTTAQDQKATLVAQKAAAEEAARQAAAAQAAAEAKAAAEAKALQ

EQAAQAQAAANNNTQATDASDQQAAAADNTQAAQTGDSTDQSAAQAVNN

SDQESTTATAAQPSASSASTAAVAANTSSANTYPAGQCTWGVKSLAPWVG

NYWGNGGQWAASAAAAGYRVGSTPSAGAVAVWNDGGYGHVAYVTGVQGGQ

IQVQEANYAGNQSIGNYRGWFNPGSVSYIYPN

TABLE 9

Deduced Amino Acid Sequence of *S. mutans* strain 5SM3 GbpB
GenBank accession number AY046414

MKKRILSAVLVSGVTLSSATTLSAVKADDFDAQIASQDSKINNLTAQQQA (SEQ ID NO:33)

AQAQVNTIQGQVSALQTQQAELQAENQRLEAQSATLGQQIQTLSSKIVAR

NESLKQQARSAQKSNAATSYINAIINSKSVSDAINRVSAIREVVSANEKM

LQQQEQDKAAVEQKQQENQAAINTVAANQETIAQNTNALNTQQAQLEAAQ

TABLE 9-continued

Deduced Amino Acid Sequence of *S. mutans* strain 5SM3 GbpB
GenBank accession number AY046414

LNLQAELTTAQDQKATLVAQKAAAEEAARQAAAAQAAAEAKAAAEAKALQ

EQAAQAQAAANNNTQATDASDQQAAAADNTQAAQTGDSTEQSAAQAVNNS

DQESTTATEAQPSASSASTAVVTANTSSANTYPAGQCTWGVKSLAPWVGN

YWGNGGQWAASAAAAGYRVGSTPSAGAVAVWNDGGYGHVAYVTGVQGGQI

QVQEANYAGNQSIGNYRGWFNPGSVSYIYPN

The compositions described herein, e.g., subunit vaccine compositions and immunogenic compositions, contain an amino acid sequence subunit of GbpB that is of sufficient length to raise an immune response in a mammal to which it is administered. As used herein, the terms "subunit" or "fragment" refer to a portion of the GbpB protein that is less than the whole naturally-occurring protein. For example, a fragment contains at least 5 contiguous amino acids of the full length naturally-occurring protein. Vaccines containing the peptide constructs described herein elicit antibodies, which bind specifically to functional domains of GbpB and/or GTF and have the additional advantage that such vaccines do not induce immunity to irrelevant or unwanted epitopes. Useful peptides are of sufficient length to raise an immune response in a mammal to which it is administered but will be less than the complete amino acid sequence of the intact GbpB. Typically, the peptide is at least 5–7 amino acids in length. Preferably the peptide is at least 12 amino acids in length; more preferable the peptide is at least 23 amino acids in length. GbpB polypeptides are derived from *S. mutans*. However, glucan binding proteins from the other strains of *S. mutans*, which share significant homology and/or function, can also be utilized. For example, a peptide in the immunogenic compositions and subunit vaccines of the invention typically comprise at least six amino acids with at least four matches to MHC Class II binding motifs. Preferably, the peptide has greater than five amino acid matches and most preferably the peptide has greater than six amino acid matches to an MHC class II binding motif. The matches are determined, for example, using a matrix-based algorithm for epitope prediction known in the art.

Peptides as shown in FIG. 1 which have a significant peak resulting from a comparison of GbpB primary sequence against a set of DBRI alleles from MHC class II motif are also contemplated. For example, according to FIG. 1, peptides which extend at least 6 amino acid residues to the right in length from residues 16, 62, 90, 121, 322 and 369 are peptides having at least four matching residues to DBR1 alleles and are contemplated for use in the compositions of the instant application. Suitable peptides may also encompass amino acid residues to the left of the indicated peak.

HLA-Binding Peptides of GbpB

GbpB peptides were synthesized and evaluated for immunogenicity, reactivity with the parent protein, and induction of caries-protective immunity. Exemplary peptides include the following fragments of glucan binding protein-B: KSNAATSYINAIINSKSVSD (the SYI peptide GbpB residues 113–132) (SEQ ID NO: 1); KHKLITIQGQVSALQTQQAG (SEQ ID NO: 2); the SAS peptide TATEAQPSASSASTAAVAAN residues 306–325 (SEQ ID NO: 3);

| Sequence | SEQ ID |
|---|---|
| KSNAATSYINAIINSKSVSD (the SYI peptide GbpB residues 113–132; | (SEQ ID NO: 1) |
| KHKLITIQGQVSALQTQQAG; | (SEQ ID NO: 2) |
| the SAS peptide TATEAQPSASSASTAAVAAN residues 306–325; | (SEQ ID NO: 3) |
| LSAVLVSGVTLSSATTLSAV residues 6–25; | (SEQ ID NO: 4) |
| LSSATTLSAVKADDFDAQIA residues 16–35; | (SEQ ID NO: 5) |
| QIASQDSKINNLTAQQQAAQ residues 33–52; | (SEQ ID NO: 6) |
| QDSKINNLTAQQQAAQAQVN residues 37–56; | (SEQ ID NO: 7) |
| QQAAQAQVNTIQGQVSALQT residues 48–67; | (SEQ ID NO: 8) |
| QAQVNTIQGQVSALQTQQAE residues 52–71; | (SEQ ID NO: 9) |
| QQIQTLSSKIVARNESLKQQ residues 88–107; | (SEQ ID NO: 10) |
| ATSYINAIINSKSVSDAINR residues 117–136; | (SEQ ID NO: 11) |
| VSAIREVVSANEKMLQQQEQ residues 137–156; | (SEQ ID NO: 12) |
| TVAANQETIAQNTNALNTQQ residues 174–193; | (SEQ ID NO: 13) |
| AQLEAAQLNLQAELTTAQDQ residues 194–213; | (SEQ ID NO: 14) |

-continued

| | | |
|---|---|---|
| KATLVAQKAAAEEAARQAAA | residues 214–233; | (SEQ ID NO: 15) |
| ALQEQAAQAQVAANNNTQAT | residues 248–267; | (SEQ ID NO: 16) |
| TEQSAAQAVNNSDQESTTAT | residues 289–308; | (SEQ ID NO: 17) |
| QPSASSASTAAVAANTSSAN | residues 311–330; | (SEQ ID NO: 18) |
| GNYWGNGGQWAASAAAAGYR | residues 349–368; | (SEQ ID NO: 19) |
| AGYRVGSTPSAGAVAVWNDG | residues 365–384; | (SEQ ID NO: 20) |
| DGGYGHVAYVTGVQGGQIQV | residues 383–402; | (SEQ ID NO: 21) |
| QEANYAGNQSIGNYRGWFNP | residues 403–422; | (SEQ ID NO: 22) |
| GNYWGNGGQWAASAAAAGRY | | (SEQ ID NO: 41). |

GNYWGNGGQWAASAAAAGRY (SEQ ID NO: 41). Amino acid residue coordinates refer to full length GbpB (SEQ ID NO:29). Equivalent peptides are intended to include equivalent sites (e.g., positions or residues) in other mutans streptococcal glucan binding proteins. For example, other glucan binding peptides can be found in *S. sobrinus* or other *S. mutans* strains. The equivalents can be identified, for example, by aligning the amino acid sequences of other mutans streptococcal GbpB's, as is routinely done by one of skill in the art.

As used herein, a vaccine composition is a composition, which elicits an immune response in a mammal to which it is administered. Elicitation of GbpB-specific antibodies protects the immunized mammal against subsequent challenge by the immunizing agent or an immunogenically cross-reactive agent. For example, production of mucosal antibodies specific for GbpB reduces the amount of *S. mutans* in an immunized mammal. Protection can be complete or partial, such as a reduction or elimination of symptoms or infection as compared with an unvaccinated mammal. An immunogenically cross-reactive agent can be, for example the whole protein (GbpB) from which a subunit peptide used as the immunogen is derived. Alternatively, an immunogenically cross-reactive agent can be a different protein, which is recognized in whole or in part by the antibodies elicited by the immunizing agent.

As used herein, an immunogenic composition encompasses a composition, which elicits an immune response in a mammal to which it is administered and which may or may not protect the immunized mammal against subsequent challenge with the immunizing agent or an immunogenically cross-reactive agent.

The raised immune response is characterized by a B cell response, a T cell response or both a B cell and T cell response. The B cell response is associated with the appearance of mucosal antibody, which is predominately IgA, and systemic antibody, which is predominantly IgG. The antibodies elicited by immunization preferably recognize both the immunizing agent and an immunogenically cross-reactive agent (e.g., the immunizing peptide and the intact GbpB protein). The antibody response protects the immunized mammal against subsequent challenge or infection with the immunizing agent or an immunogenically cross-reactive agent.

In addition to the peptides listed in Table 1, other immunogenic domains of GbpB, as well as domains of non-GbpB origin, which enhance adjuvanticity or produce an immunogenic response against other infectious agents are optionally included in the compositions of the invention. For example, the vaccine or immunogenic composition contains an additional immunogenic component which is an immunogenic portion of a pathogen including, but not limited to, diphtheria, pertussis, tetanus, measles, influenza, poliovirus, and retroviruses resulting in a multivalent composition raising an immune response to greater than one infectious disease or agent. A multivalent vaccine includes immunogenic epitopes and appropriate adjuvant sequences targeting early childhood infections.

GbpB-GTF Chimeric Peptides

Immunogenic compositions containing one or more domains of GbpB combined with one or more domains of GTF were produced and evaluated for the ability to elicit antibody production. This strategy permits a combined attack on the molecular pathogenesis of *mutans streptococci* utilizing two or more epitopes. Synthetic peptides containing an amino acid sequence of one or more functional domains of *Streptococcus mutans* glucosyltransferases induce immune responses, which reduce recolonization of the bacteria. Chimeric peptides containing GTF sequences and GbpB sequences provide a more comprehensive attack on the colonization of the bacteria by increasing the enzyme inhibitory capacity of the immune response, eliminating responses to irrelevant epitopes and reducing the glucan binding capacity.

Tables 10–16 include the amino acid sequence of GTF isozymes from various *Streptococci*.

TABLE 10

Deduced Amino Acid Sequence of *S. mutans* GTF-B

| | |
|---|---|
| MDKKVRYKLRKVKKRWVTVSVASAVMTLTTLSGGLVKADSNESK | (SEQ ID NO:34) |
| SQISNDSNTSVVTANEESNVITEATSKQEAASSQTNHTVTTSSSSTSVVNPKEVVSNP | |
| YTVGETASNGEKLQNQTTTVDKTSEAAANNISKQTTEADTDVIDDSNAANLQILEKLP | |

TABLE 10-continued

Deduced Amino Acid Sequence of *S. mutans* GTF-B

NVKEIDGKYYYYDNNGKVRTNFTLIADGKILHFDETGAYTDTSIDTVNKDIVTTRSNL

YKKYNQVYDRSAQSFEHVDHYLTAESWYRPKYILKDGKTWTQSTEKDFRPLLMTWWPD

QETQRQYVNYMNAQLGINKTYDDTSNQLQLNIAAATIQAKIEAKITTLKNTDWLRQTI

SAFVKTQSAWNSDSEKPFDDHLQNGAVLYDNEGKLTPYANSNYRILNRTPTNQTGKKD

PRYTADNTIGGYEFLLANDVDNSNPVVQAEQLNWLHFLMNFGNIYANDPDANFDSIRV

DAVDNVDADLLQIAGDYLKAAKGIHKNDKAANDHLSILEAWSDNDTPYLHDDGDNMIN

MDNKLRLSLLFSLAKPLNQRSGMNPLITNSLVNRTDDNAETAAVPSYSFIRAHDSEVQ

DLIADIIKAEINPNVVGYSFTMEEIKKAFEIYNKDLLATEKKYTHYNTALSYALLLTN

KSSVPRVYYGDMFTDDGQYMAHKTINYEAIETLLKARIKYVSGGQAMRNQQVGNSEII

TSVRYGKGALKATDTGDRTTRTSGVAVIEGNNPSLRLKASDRVVVNMGAAHKNQAYRP

LLLTTDNGIKAYHSDQEAAGLVRYTNDRGELIFTAADIKGYANPQVSGYLGVWVPVGA

ALIKMFALRLARPHQQMASVHQNAALDSRVMFEGFSNFQAFATKKEEYTNVVIAKNVD

KFAEWGVTDFEMAPQYVSSTDGSFLDSVIQNGYAFTDRYDLGISKPNKYGTADDLVKA

IKALHSKGIKVMADWVPDQMYAFPEKEVVTATRVDKYGTPVAGSQIKNTLYVVDGKSS

GKDQQAKYGGAFLEELQAKYPELFARKQISTGVPMDPSVKIKQWSAKYFNGTNILGRG

AGYVLKDQATNTYFNISDNKEINFLPKTLLNQDSQVGFSYDGKGYVYYSTSGYQAKNT

FISEGDKWYYFDNNGYMVTGAQSINGVNYYFLSNGLQLRDAILKNEDGTYAYYGNDGR

RYENGYYQFMSGVWRHFNNGEMSVGLTVIDGQVQYFDEMGYQAKGKFVTTADGKIRYF

DKQSGNMYRNRFIENEEGKWLYLGEDGAAVTGSQTINGQHLYFRANGVQVKGEFVTDH

HGRISYYDGNSGDQIRNRFVRNAQGQWFYFDNNGYAVTGARTINGQLLYFRANGVQVK

GEFVTDRYGRISYYDGNSGDQIRNRFVRNAQGQWFYFDNNGYAVTGARTINGQHLYFR

ANGVQVKGEFVTDRHGRISYYDGNSGDQIRNRFVRNAQGQWFYFDNNGYAVTGARTIN

GQHLYFRANGVQVKGEFVTDRYGRISYYDANSGERVRIN

TABLE 11

Deduced Amino Acid Sequence of *S. mutans* GTF-C

MEKKVRFKLRKVKKRWVTVSIASAVVTLTSLSGSLVKADSTDDR (SEQ ID NO:35)

QQAVTESQASLVTTSEAAKETLTATDTSTATSATSQPTATVTDNVSTTNQSTNTTANT

ANFVVKPTTTSEQAKTDNSDKIITTSKAVNRLTATGKFVPANNNTAHPKTVTDKTVPI

KPKIGKLKQPSSLSQDDIAALGNVKNIRKVNGKYYYYKEDGTLQKNYALNINGKTFFF

DETGALSNNTLPSKKGNITNNDNTNSFAQYNQVYSTDVANFEHVDHYLTAESWYRPKY

ILKDGKTWTQSTEKDFRPLLMTWWPDQETQRQYVNYMNAQLGIHQTYNTATSPLQLNL

AAQTIQTKIEEKITAEKNTNWLRQTISAFVKTQSAWNSDSEKPFDDHLQKGALLYSNN

SKLTSQANSNYRILNRTPTNQTGKKDPRYTADRTIGGYEFLLANDVDNSNPVVQAEQL

NWLHFLMNFGNIYANDPDANFDSIRVDAVDNVDADLLQIAGDYLKAAKGIHKNDKAAN

DHLSILEAWSYNDTPYLHDDGDNMINMDNRLRLSLLYSLAKPLNQRSGMNPLITNSLV

NRTDDNAETAAVPSYSFIRAHDSEVQDLIRNIIRTEINPNVVGYSFTTEEIKKAFEIY

NKDLLATEKKYTHYNTALSYALLLTNKSSVPRVYYGDMFTDDGQYMAHKTINYEAIET

TABLE 11-continued

Deduced Amino Acid Sequence of S. mutans GTF-C

LLKARIKYVSGGQAMRNQQVGNSEIITSVRYGKGALKATDTGDRTTRTSGVAVIEGNN

PSLRLKASDRVVVNMGAAHKNQAYRPLLLTTDNGIKAYHSDQEAAGLVRYTNDRGELI

FTAADIKGYANPQVSGYLGVWVPVGAAADQDVRVAASTAPSTDGKSVHQNAALDSRVM

FEGFSNFQAFATKKEEYTNVVIAKNVDKFAEWGVTDFEMAPQYVSSTDGSFLDSVIQN

GYAFTDRYDLGISKPNKYGTADDLVKAIKALHSKGIKVMADWVPDQMYALPEKEVVTA

TRVDKYGTPVAGSQIKNTLYVVDGKSSGKDQQAKYGGAFLEELQAKYPELFARKQIST

GVPMDPSVKIKQWSAKYFNGTNILGRGAGYVLKDQATNTYFSLVSDNTFLPKSLVNPN

HGTSSSVTGLVFDGKGYVYYSTSGNQAKNAFISLGNNWYYFDNNGYMVTGAQSINGAN

YYFLSNGIQLRNAIYDNGNKVLSYYGNDGRRYENGYYLFGQQWRYFQNGIMAVGLTRV

HGAVQYFDASGFQAKGQFITTADGKLRYFDRDSGNQISNRFVRNSKGEWFLFDHNGVA

VTGTVTFNGQRLYFKPNGVQAKGEFIRDANGYLRYYDPNSGNEVRNRFVRNSKGEWFL

FDHNGIAVTGARVVNGHASILSLMVFRLRESSLQSVKVVSNTMILIPEMKFVIVM

TABLE 12

Deduced Amino Acid Sequence of S. mutans GTF-D

METKRRYKMHKVKKHWVTVAVASGLITLGTTTLGSSVSAETEQQ          (SEQ ID NO:36)

TSDKVVTQKSEDDKAASESSQTDAPKTKQAQTEQTQAQSQANVADTSTSITKETPSQN

ITTQANSDDKTVTNTKSEEAQTSEERTKQSEEAQTTASSQALTQAKAELTKQRQTAAQ

ENKNPVDLAAIPNVKQIDGKYYYIGSDGQPKKNFALTVNNKVLYFDKNTGALTDTSQY

QFKQGLTKLNNDYTPHNQIVNFENTSLETIDNYVTADSWYRPKDILKNGKTWTASSES

DLRPLLMSWWPDKQTQIAYLNYMNQQGLGTGENYTADSSQESLNLAAQTVQVKIETKI

SQTQQTQWLRDIINSFVKTQPNWNSQTESDTSAGEKDHLQGGALLYSNSDKTAYANSD

YRLLNRTPTSQTGKPKYFEDNSSGGYDFLLANDIDNSNPVVQAEQLNWLHYLMNYGSI

VANDPEANFDGVRVDAVDNVNADLLQIASDYLKAHYGVDKSEKNAINHLSILEAWSDN

DPQYNKDTKGAQLPIDNKLRLSLLYALTRPLEKDASNKNEIRSGLEPVITNSLNNRSA

EGKNSERMANYIFIRAHDSEVQTVIAKIIKAQINPKTDGLTFTLDELKQAFKIYNEDM

RQAKKKYTQSNIPTAYALMLSNKDSITRLYYGDMYSDDGQYMATKSPYYDAIDTLLKA

RIKYAAGGQDMKITYVEGDKSHMDWDYTGVLTSVRYGTGANEATDQGSEATKTQGMAV

ITSNNPSLKLNQNDKVIVNMGAAHKNQEYRPLLLTTKDGLTSYTSDAAAKSLYRKTND

KGELVFDASDIQGYLNPQVSGYLAVWVPVGASDNQDVRVAASNKANATGQVYESSSAL

DSQLIYEGFSNFQDFVTKDSDYTNKKIAQNVQLFKSWGVTSFEMAPQYVSSEDGSFLD

SIIQNGYAFEDRYDLAMSKNNKYGSQQDMINAVKALHKSGIQVIADWVPDQIYNLPGK

EVVTATRVNDYGEYRKDSEIKNTLYAANTKSNGKDYQAKYGGAFLSELAAKYPSIFNR

TQISNGKKIDPSEKITAWKAKYFNGTNILGRGVGYVLKDNASDKYFELKGNQTYLPKQ

MTNKEASTGFVNDGNGMTFYSTSGYQAKNSFVQDAKGNWYYFDNNGHMVYGLQQLNGE

VQYFLSNGVQLRESFLENADGSKNYFGHLGNRYSNGYYSFDNDSKWRYFDASGVMAVG

LKTINGNTQYFDQDGYQVKGAWITGSDGKKRYFDDGSGNMAVNRFANDKNGDWYYLNS

DGIALVGVQTINGKTYYFGQDGKQIKGKIITDNGKLKYFLANSGELARNIFATDSQNN

TABLE 12-continued

Deduced Amino Acid Sequence of S. mutans GTF-D

WYYFGSDGVAVTGSQTIAGKKLYFASDGKQVKGSFVTYNGKVHYYHADSGELQVNRFE

ADKDGNWYYLDSNGEALTGSQRINDQRVFFTREGKQVKGDVAYDERRLLVYR

TABLE 13

Deduced Amino Acid Sequence of S. sobrinus GTF-I

| | |
|---|---|
| MEKNVRFKMHKVKKRWVTLSVASATMLASALGASVASADTDTAS | (SEQ ID NO:37) |

DDSNQAVVTGDQTTNNQATDQTSIAATATSEQSASTDAATDQASAAEQTQGTTASTDT

AAQTTTNANEAKWVPTENENQGFTDEMLAEAKNVATAESDSIPSDLAKMSNVKQVDGK

YYYYDQDGNVKKNFAVSVGDKIYYFDETGAYKDTSKVDADKSSSAVSQNATIFAANNR

AYSTSAKNFEAVDNYLTADSWYRPKSILKDGKTWTESGKDDFRPLLMAWWPDTETKRN

YVNYMNKVVGIDKTYTAETSQADLTAAAELVQARIEQKITSENNTKWLREAISAFVKT

QPQWNGESEKPYDDHLQNGALLFDNQTDLTPDTQSNYRLLNRTPTNQTGSLDSRFTYN

PNDPLGGYDFLLANDVDNSNPVVQAEQLNWLHYLLNFGSIYANDADANFDSIRVDAVD

NVDADLLQISSDYLKAAYGIDKNNKNANNHVSIVEAWSDNDTPYLHDDGDNLMNMDNK

FRLSMLWSLAKPLDKRSGLNPLIHNSLVDREVDDREVETVPSYSFARAHDSEVQDIIR

DIIKAEINPNSFGYSFTQEEIEQAFKIYNEDLKKTDKKYTHYNVPLSYTLLLTNKGSI

PRVYYGDMFTDDGQYMANKTVNYDAIESLLKARMKYVSGGQAMQNYQIGNGEILTSVR

YGKGALKQSDKGDATTRTSGVGVVMGNQPNFSLDGKVVALNMGAAHANQEYRALMVST

KDGVATYATDADASKAGLVKRTDENGYLYFLNDDLKGVANPQVSGFLQVWVPVGAADD

QDIRVAASDTASTDGKSLHQDAAMDSRVMFEGFSNFQSFATKEEEYTNVVIANNVDKF

VSWGITDFEMAPQYVSSTDGQFLDSVIQNGYAFTDRYDLGMSKANKYGTADQLVKAIK

ALHAKGLKVMADWVPDQMYTFPKQEVVTVTRTDKFGKPIAGSQINHSLYVTDTKSSGD

DYQAKYGGAFLDELKEKYPELFTKKQISTGQAIDPSVKIKQWSAKYFNGSNILGRGAD

YVLSDQVSNKYFNVASDTLFLPSSLLGKVVESGIRYDGKGYIYNSSATGDQVKASFIT

EAGNLYYFGKDGYMVTGAQTINGANYFFLENGTALRNTIYTDAQGNSHYYANDGKRYE

NGYQQFGNDWRYFKDGNMAVGLTTVDGNVQYFDKDGVQAKDKIIVTRDGKVRYFDQHN

GNAATNTFIADKTGHWYYLGKDGVAVTGAQTVGKQKLYFEANGQQVKGDFVTSDEGKL

YFYDVDSGDMWTDTFIEDKAGNWFYLGKDGAAVTGAQTIRGQKLYFKANGQQVKGDIV

KGTDGKIRYYDAKSGEQVFNKTVKAADGKTYVIGNDGVAVDPSVVKGQTFKDASGALR

FYNLKGQLVTGSGWYETANHDWVYIQSGKALTGEQTINGQHLYFKEDGHQVKGQLVTG

TDGKVRYYDANSGDQAFNKSVTVNGKTYYFGNDGTAQTAGNPKGQTFKDGSDIRFYSM

EGQLVTGSGWYENAQGQWLYVKNGKVLTGLQTVGSQRVYFDENGIQAKGKAVRTSDGK

IRYFDENSGSMITNQWKFVYGQYYYFGNDGARIYRGWN

TABLE 14

Deduced Amino Acid Sequence of S. sobrinus GTF-U

| | |
|---|---|
| MEKKLHYKLHKVKKHWVTIAVASIGLVSLVGAGTVSAEDKVAND | (SEQ ID NO:38) |

TTAQATVGVDTGQDQATTNDANTNTTDTDTADQSANTNQDQAGSDQSNNQDQAKQDTA

TABLE 14-continued

Deduced Amino Acid Sequence of S. sobrinus GTF-U

NTDRNQADNSQTDNNQATDQATSPATDGTSVQRRDAANVATAADQEGQTAPSEQEKSA

ALSLDNVKLIDGKYYYVQADGSYKKNFAITVNGQMLYFDSDTGALSSTSTYSFSQGTT

NLVDDFSSHNKAYDSTAKSFELVNGYLTANSWYRPAGILRNGQTWEASNENDLRPVLM

SWWPDKDTQVAYVNYMNKYLSANETEVTNETSQVDLNKEAQSIQTKIEQKITSDNSTQ

WLRTAMEAFVAAQPKWNMSTENFNKGDHLQGGALLYTNSDLTPWANSDYRLLNRTPTQ

QDGTKKYFTEGGEGGYEFLLSNDVDNSNPVVQAEQLNQLHYLMNWGDIVMGDKDANFD

GVRVDAVDNVNADLLQVYSNYFKDNYKVTDSEANALAHISILEAWSLNDNQYNEDTNG

TALSIDNSSRLTSLAVLTKQPGQRIDLSNLISESVNKERANDTAYGDTIPTYSFVRAH

DSEVQTVIAKIVKEKIDTNSDGYTFTLDQLKDAFKIYNEDMAKVNKTYTHYNIPAAYA

LLLSNMESVPRVYYGDLYTDDGQYMAKKSPYYDAIATMLQGRIAYVSGGQSEEVHKVN

GNNQILSSVRYGQDLMSADDTQGTDLSRTSGLVTLVSNDPNLDLGGDSLTVNMGRAHA

NQAYRPLILGTKDGVQSYLKDSDTNIVKYTDANGNLTFTADDIKGYSTVDMSGYLAVW

VPVGAKDGQDVRVAADTNQKADGKSLKTSAALDSQVIYEGFSNFQDFANNDADYTNKK

IAENADFFKKLGITSFEMAPQYVSATDGSFLDSIIQNGYAFSDRYDLAMSKNNKYGSK

DDLANALKALHANGIQAIADWVPDQTYQLPGEEVVTAKRTNSYGNPTFDAYINNALYA

TNTKSSGSDYQAQYGGAFLDELKAKYPDMFTVNMISTGKPIDPSTKIKQWEAKYFNGT

NVLGKGAGYVLSDDATGKYFTVNENGDFLPASFTGDQNAKTGFYYDGTGMAYYSTSGN

KAVNSFIYEGGHYYYFDKDGHMVTGSYKAEDGNDYYFLPNGIQMRDAIYQDAQGNSYY

YGRTGILYKGDNWYPFVDPNNANKTVFRYFDANNVMAIGYRNMYGQTYYFDENGFQAK

GQLLTDDKGTHYFDEDNGAMAKNKFVNVGDDWYYMDGNGNAVKGQYPVNNQILYFNPE

TGVQVKGQFITDAQGRTSYYDANSGALKSSGFFTPNGSDWYYAENGYVYKGFKQVAEN

QDQWYYFDQTTGKQAKGAAKVDGRDLYFNPDSGVQVKGDFATDESGNTSFYHGDNGDK

VVGGFFTTGNNAWYYADNNGNLVKGFQEIDGKWYHFDEVTGQQAKGAALVNGQQLYFD

VDSGIQVKGDFVTDGQGNTSYYDVNSGDKKVNGFFTTGDNAWYYADGQGNLAKGRKSI

DNQDLYFDPATGKQVKGQLVSIDGRNYYFDSGSGNMAKNRFVRIGDQWIYFGNDGAAT

NL

TABLE 15

Deduced Amino Acid Sequence of S. downei GTF-S

MEKNLRYKLHKVKKQWVAIGVTTVTLSFLAGGQVVAADTNNNDG     (SEQ ID NO:39)

TSVQVNKMVPSDPKFDAQAQNGQLAQAMFKAANQADQTATSQVSPATDGRVDNQVTPA

ANQPAANVANQDVANPATDAGALNRQSAADTSTDGKAVPQTSDQPGHLETVDGKTYYV

DANGQRLKNYSMVIDGKTYYFDGQTGEAQTDLPKTGQANQDNVPDSYQANNQAYSNEA

SSFETVDNYLTADSWYRPRKILKNGQSWQASSEGDLRPILMTWWPDAATKAAYANFWA

KEGLISGSYRQNSANLDAATQNIQSAIEKKIASEGNTNWLRDKMSQFVKSQNQWSIAS

ENETVYPNQDHMQGGALLFSNSKDTEHANSDWRLLNRNPTFQTGKQKYFTTNYAGYEL

LLANDVDNSNPVVQAEQLNHLHYLMNWGDIVMGDKDANFDGVRVDAVDNVNADLLQIQ

RDYYKAKYGTDQNEKNAIDHLSILEAWSGNDNDYVKDQNNFSLSIDNDQRSGMLKAFG

TABLE 15-continued

Deduced Amino Acid Sequence of *S. downei* GTF-S

YASAYRGNLSNLATAGLKNRSANPDSDPVPNYVFIRAHDSEVQTRIAKIIREKLGKTN

ADGLTNLTLDDLNKAFDIYNQDMNATDKVYYPNNLPMAYAWMLQNKDTVTRVYYGDMY

TDNGQYMATKTPFYNAIETLLKGRIKYVAGGQAVSYKQDWSSGILTSVRYGKGANSAS

DAGNTETRNSGMALLINNRPNFRAYRNLTLNMGAAHKSQAYRPLLLSTKDGIATYLND

SDVDSRQYKYTDSQGNLSFSASELQSVANAQVSGMIQVWVPVGAADNQDVRTSPSTQA

TKDGNIYHQSDALDSQVIYEGFSNFQAFAQSPDQYTNAVIAKNGDLFKSWGITQFEMA

PQYVSSEDGTFLDSVILNGYAFSDRYDLAMSKNNKYGSKQDLANAIKGLQSAGIKVLS

DLVPNQLYNLPGKEVVTATRVNQYGQAKSGATINKTPYVANTRSYGDYQEQYGGKFLD

DLQKLYPRLFSTKQISTGKPIDPSVKITNWSAKYFNGSNILGRGAKYVLSEGNKYLNL

ADGKLFLPTVLNNTYGQPQVSANGFISKNGGIHYLDKNGQEVKNRFKEISGSWYYFDS

DGKMATGKTKIGNDTYLFMPNGKQLKEGVWYDGKKAYYYDDNGRTWTNKGFVEFRVDG

QDKWRYFNGDGTIAIGLVSLDNRTLYFDAYGYQVKGQTVTINGKSYTFDADQGDLVQT

DNANPAPQGQAGWKLLGDNQWGYRKDGQLLTGEQTIDGQKVFFQDNGVQVKGGTATDA

SGVLRFYDRDQGHQVGKGWYSTSDDNWVYVNESGQVLTGLQTIDGQTVYFDDKGTQAK

GKAVWDENGNLRYFDADSGNMLRDRWKNVDGNWYYFNRNGLATRW

TABLE 16

Deduced Amino Acid Sequence of *S. salivarius* GTF-I

MENKIHYKLHKVKKQWVTIAVASVALATVLGGLSVTTSSVSADE     (SEQ ID NO:40)

TQDKTVTQSNSGTTASLVTSPEATKEADKRTNTKEADVLTPAKETNAVETATTTNTQA

TAEAATTATTADVAVAAVPNKEAVVTTDAPAVTTEKAEEQPATVKAEVVNTEVKAPEA

ALKDSEVEAALSLKNIKNIDGKYYYVNEDGSHKENFAITVNGQLLYFGKDGALTSSST

YSFTPGTTNIVDGFSINNRAYDSSEASFELIDGYLTADSWYRPASIIKDGVTWQASTA

EDFRPLLMAWWPNVDTQVNYLNYMSKVFNLDAKYSSTDKQETLKVAAKDIQIKTEQKI

QAEKSTQWLRETISAFVKTQPQWNKETENYSKGGGEDHLQGGALLYVNDSRTPWANSD

YRRLNRTATNQTGTIDKSILDEQSDPNHMGGFDFLLANDVDLSNPVVQAEQLNQIHYL

MNWGSIVMGDKDANFDGIRVDAVDNVDADMLQLYTNYFREYYGVNKSEANALAHISVL

EAWSLNDNHYNDKTDGAALAMENKQRLALLFSLAKPIKERTPAVSPLYNNTFNTTQRD

EKTDWINKDGSKAYNEDGTVKQSTIGKYNEKYGDASGNYVFIRAHDNNVQDIIAEIIK

KEINPKSDGFTITDAEMKQAFEIYNKDMLSSDKKYTLNNIPAAYAVMLQNMETITRVY

YGDLYTDDGHYMETKSPYYDTIVNLMKSRIKYVSGGQAQRSYWLPTDGKMDNSDVELY

RTNEVYTSVRYGKDIMTANDTEGSKYSRTSGQVTLVANNPKLNLDQSAKLNVEMGKIH

ANQKYRALIVGTADGIKNFTSDADAIAAGYVKETDSNGVLTFGANDIKGYETFDMSGF

VAVWVPVGASDNQDIRVAPSTEAKKEGELTLKATEAYDSQLIYEGFSNFQTIPDGSDP

SVYTNRKIAENVDLFKSWGVTSFEMAPQFVSADDGTFLDSVIQNGYAFADRYDLAMSK

NNKYGSKEDLRDALKALHKAGIQAIADWVPDQIYQLPGKEVVTATRTDGAGRKIADAI

IDHSLYVANSKSSGKDYQAKYGGEFLAELKAKYPEMFKVNMISTGKPIDDSVKLQWWK

AEYFNGTNVLERGVGYVLSDEATGKYFTVTKEGNFIPLQLTGKEKVITGFSSDGKGIT

TABLE 16-continued

Deduced Amino Acid Sequence of S. salivarius GTF-I

YFGTSGTQAKSAFVTFNGNTYYFDARGHMVTNSEYSPNGKDVYRFLPNGIMLSNAFYI

DANGNTYLYNSKGQMYKGGYTKFDVSETDKDGKESKVVKFRYFTNEGVMAKGVTVIDG

FTQYFGEDGFQAKDKLVTFKGKTYYFDAHTGNGIKDTWRNINGKWYYFDANGVAATGA

QVINGQKLYFNEDGSQVKGGVVKNADGTYSKYKEGFGELVTNEFFTTDGNVWYYAGAN

GKTVTGAQVINGQHLYFNADGSQVKGGVVKNADGTYSKYNASTGERLTNEFFTTGDNN

WYYIGANGKSVTGEVKIGDDTYFFAKDGKQVKGQTVSAGNGRISYYYGDSGKRAVSTW

IEIQPGVYVYFDKNGLAYPPRVLN

Exemplary GTF peptides are shown in Tables 17–19.

TABLE 17

Catalytic Domain Peptides of GTF

| | |
|---|---|
| DANFDSIRVDAVDNVDADLLQI | (SEQ ID NO: 25) |
| PLDKRSGLNPLIHNSLVDREVDDRE | (SEQ ID NO: 26) |

TABLE 18

Glucan-binding Domain Peptides of GTF

| | |
|---|---|
| TGAQTIKGQKLYFKANGQQVKG | (SEQ ID NO: 23) |
| DGKLRYYDANSGDQAFNKSV | (SEQ ID NO: 27) |

TABLE 19

Surface Domain Peptide of GTF

| | |
|---|---|
| QWNGESEKPYDDHL | (SEQ ID NO: 28) |

Diepitopic peptide constructs, which induce protective antibody to both S. mutans GbpB, and GTF of mutans streptococci are made using known methods. One peptide is drawn from the GbpB sequence and the other peptide is drawn from the GTF sequence. Useful GTF sequences are described in U.S. Pat. No. 5,686,075 and U.S. patent application Ser. No. 09/290,049. The multiepitopic sequences are placed on a multiple antigenic peptide (MAP) backbone, expressed recombinantly or in an attenuated expression vector or by other methods known in the art. For example, diepitopic immunogenic and vaccine compositions include S. mutans GbpB peptide KSNAATSYINAIINSKSVSD (SEQ ID NO: 1) combined with S. sobrinus GTF-B residues 1303 to 1324;

| | |
|---|---|
| TGAQTIKGQKLYFKANGQQVKG<br>or S mutans GTF-B residues 442 to 462; | (SEQ ID NO: 23) |
| DANFDSIRVDAVDNVDADLLQ. | (SEQ ID NO: 24) |

The peptides are directly linked to one another or are separated by intervening residues (e.g., one or more lysines). The compositions optionally contain an immunogenicity-enhancing agent, such as a bacterially-derived adjuvant. For example, a GbpB or GTF peptide is conjugated to a known protein, (such as tetanus toxoid) or a carrier (such as a synthetic polymer carrier) to give a macromolecular structure to the composition, which enhances immunogenicity. The compositions contain at least two different peptides, and the peptides are synthesized and covalently attached to a peptidyl core matrix to yield a macromolecule with a high density of peptides in a single structure. Each peptide in such a structure comprises a GbpB peptide, which is of sufficient length to raise an immune response in a mammal to which it is administered. The composition optionally contains a plurality of copies of a GbpB or GTF peptide. Synthetic peptide vaccine design was carried out using a MAP construct using known methods, e.g., Tam et al., PNAS USA 85:5409–5413 (1988).

A peptidyl core matrix contains of amino acids such as lysine, arginine and histidine. In particular, at least 2 peptides are synthesized on a core matrix of at least one lysine to yield a macromolecular vaccine composition. Particularly, at least 2 peptides are synthesized on a core matrix of 3 lysines. In another example, the vaccine composition is made by covalently attaching 4 peptides to a core matrix of 3 lysines yielding a radially branched peptide with four dendritic arms. The four peptides present can be the same or different. Such multiepitopic peptide constructs induced enhanced immune responses. Moreover, the combination of sequences from several strains into a synthetic or recombinant multi-epitopic construct increases the protective potential of subunit vaccines for dental caries.

Vaccine Formulations

Suitable peptide(s) are incorporated into a microparticle, e.g., a PGLA microparticle, for improved delivery and immune response. Such bioadhesive microparticles can facilitate primary and secondary mucosal antibody formation. Additionally, other ways of enhancing immune responses to mucosally applied peptides (antigens) include use of mucosal adjuvants such as detoxified versions of cholera toxin or E. coli heat-labile toxins (Smith et al., Infect. Immunity 69(8):4767–4773 (2002)).

Peptides are formulated with a physiologically acceptable medium. The physiological medium may include, but is not limited to, water, buffered saline, polyols (e.g., glycerol, propylene glycol, liquid polyethylene glycol) and dextrose solutions. The optimum concentration of the active ingredient(s) in the chosen medium can be determined empirically, according to procedures well known in the art, and will depend on the ultimate pharmaceutical formulation desired. Methods of introduction of exogenous peptides at the site of treatment include, but are not limited to, intradermal, intramuscular, intraperitoneal, intravenous, subcutaneous, oral, sublingual, intraocular, rectal and intranasal. Other suitable methods of introduction can also include rechargeable or biodegradable devices and slow release polymeric devices. The compositions of this invention can also be administered as part of a combinatorial therapy with other agents.

Peptides are administered at an intravenous dosage of approximately 1 to 100 µmoles of the polypeptide per kg of body weight per day. Administration is typically parenteral. For example, the peptides are administered intravenously, subcutaneously, intramuscularly, intraperitoneally, orally, or intranasally.

Antibody Production

The peptides of the invention are used to raise antibodies or to elicit an immune response. The term "antibody" as used herein refers to immunoglobulin molecules and immunogenically active portions of immunoglobulin molecules, i.e., molecules that contain an antigen binding site that specifically binds an antigen. A molecule that specifically binds to a peptide of the invention is a molecule that binds to that peptide or a fragment thereof, but does not substantially bind other molecules in a sample, e.g., a biological sample, which naturally contains the peptide. Examples of immunogenically active portions of immunoglobulin molecules include F(ab) and F(ab')$_2$ fragments which can be generated by treating the antibody with an enzyme such as pepsin. The invention provides polyclonal, monoclonal, and transgenic antibodies that bind to a peptide of the invention. The term "monoclonal antibody" or "monoclonal antibody composition", as used herein, refers to a population of antibody molecules that contain only one species of an antigen binding site capable of immunoreacting with a particular epitope of a peptide of the invention. A monoclonal antibody composition thus typically displays a single binding affinity for a particular peptide of the invention with which it inimunoreacts.

Polyclonal antibodies are prepared as described above by immunizing a suitable subject with a desired immunogen, e.g., the whole glucan binding protein-B, a peptide of the invention or fragment thereof. The antibody titer in the immunized subject can be monitored over time by standard techniques, such as with an enzyme linked immunosorbent assay (ELISA) using immobilized peptide or protein. If desired, the antibody molecules directed against the peptide can be isolated from the mammal (e.g., from the blood) and further purified by well-known techniques, such as protein A chromatography to obtain the IgG fraction. Also, antibodies can be isolated from the yolks of immunized chicken eggs (IgY) (Svendsen et al., *Lab. Anim. Sci.* 45:89–93 (1995)) or transgenic antibodies can be prepared in plants or other hosts and extracted for human use (Ma et al., *Eur. J. Immol.*, 24:131–138 (1994)). At an appropriate time after immunization, e.g., when the antibody titers are highest, antibody-producing cells can be obtained from the subject and used to prepare monoclonal antibodies by standard techniques, such as the hybridoma technique originally described by Kohler and Milstein, *Nature*, 256:495–497 (1975), the human B cell hybridoma technique (Kozbor et al., *Immunol. Today*, 4:72 (1983)), the EBV-hybridoma technique (Cole et al., *Monoclonal Antibodies and Cancer Therapy*, Alan R. Liss, Inc., pp. 77–96 (1985)) or trioma techniques. The technology for producing hybridomas is well known (see generally Ausubel, et al. (Eds.), *Current Protocols in Immunology*, John Wiley & Sons, Inc., New York, N.Y. (2001)). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds a peptide of the invention.

Any of the many well known protocols used for fusing lymphocytes and immortalized cell lines can be applied for the purpose of generating a monoclonal antibody to a peptide of the invention (see, e.g., *Current Protocols in Immunology, supra*; Galfre et al., *Nature*, 266:55052 (1977); R. H. Kenneth, in *Monoclonal Antibodies: A New Dimension In Biological Analyses*, Plenum Publishing Corp., New York, N.Y. (1980); and Lerner, *Yale J. Biol. Med.*, 54:387–402 (1981)). Moreover, the ordinarily skilled worker will appreciate that there are many variations of such methods that also would be useful.

Alternative to preparing monoclonal antibody-secreting hybridomas, a monoclonal antibody to a peptide of the invention can be identified and isolated by screening a recombinant combinatorial immunoglobulin library (e.g., an antibody phage display library) with the peptide to thereby isolate immunoglobulin library members that bind the peptide. Kits for generating and screening phage display libraries are commercially available (e.g., the Pharmacia *Recombinant Phage Antibody System*, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al., *Bio/Technology*, 9:1370–1372 (1991); Hay et al., *Hum. Antibod. Hybridomas*, 3:81–85 (1992); Huse et al., *Science*, 246:1275–1281 (1989); Griffiths et al., *EMBO J.*, 12:725–734 (1993).

Additionally, recombinant antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art. The invention also is intended to cover human antibodies. Methods for production, isolation purification and use are known to those skilled in the art using standard methodologies.

Active immunization with *Streptococcus mutans* has been shown to induce protection against experimental dental caries. Protection results from continuous secretion of salivary antibody to Gbp-B. Also contemplated by the present application is the use of the peptides described herein for conferring passive immunity to a mammal by administration of antibodies directed to the peptides of the invention using the methods described by Smith et. al., *Infect. and Immun.* 69(5):3135–3142 (2001). Passive immunity and protection from *Streptococcus mutans* can result from administration of antibodies specific to Gbp-B peptides (e.g., SEQ ID NOS. 1–22) as described herein. Routes for administration include intravenous, intranasal, topical, and dietary, including the inclusion of the antibody in mouthwash, toothpaste or chewing gum. The administration of Gbp-B peptide antibodies can have an immunotherapeutic efficacy for dental caries by interfering with the accumulation of *S. mutans* in the biofilm and the subsequent events that cause dental caries.

The present invention further relates to a method of provoking an immune response to glucan binding protein or to glucosyltransferase in a mammal by administering an immunogenic or vaccine composition of the invention. Preferably, the immune response results in interference with glucan binding in the biofilm in mammals after administration of the vaccine composition. Alternatively, the immune response results in interference with the enzymatic activity of glucosyltransferase in mammals. The immune response elicited by the compositions and methods of the invention can be humoral or systemic; for example, the immune response can be a mucosal response. The immune response elicited by the method of the present invention results in reduction of the colonization or accumulation of mutans streptococcal strains in the mammal to which the vaccine or immunogenic composition is administered.

The compositions of the present invention are administered to any mammal in which the prevention and/or reduction of dental caries is desired. Suitable mammals include primates, humans, cats, dogs, mice, rats and other mammals in which it is desirable to inhibit dental caries. The present invention provides a vaccine that is useful for preventing, halting or reducing the progression of dental caries in a mammal to which the vaccine is administered.

In the method of the present invention of provoking an immune response to GbpB, mammals in which an immune response to GbpB is desired are given the vaccine or immunogenic compositions described herein. The compositions can be included in a formulation, which is administered to an individual being treated; such a formulation can also include a physiologically compatible carrier (e.g., a physiological buffer), stabilizers, flavorants, adjuvants and other components. The vaccine can be administered by a variety of routes (e.g., parenterally, mucosally, intranasally, intraocularly, intravenously, rectally, orally) and the components of the formulation will be selected accordingly. The amount to be administered and the frequency of administration can be determined empirically and will take into consideration the age and size of the mammal being treated and the stage of the dental caries disease (e.g., prior to colonization of *mutans streptococci*, soon after colonization of *mutans streptococci* or in later stages of colonization).

EXAMPLE 1

Identification of Immunogenic Regions

Peptides presented in conjunction with class II MHC molecules were derived from GbpB that has been processed in the phagosome of the antigen processing cell. The peptides bind to MHC molecules on the surface of these cells in a linear fashion. The binding was determined by the interaction of the peptide's amino acid side chains with the binding pockets in the MHC molecule. The characteristics of peptides that are likely to bind to a given MHC were directly deduced from pooled sequencing data of MHC alleles, resulting in an estimated binding probability. Thus, in order to identify potential B cell epitopes within GbpB sequence, which can be used for design of subunit vaccines, a matrix-based algorithm for epitope prediction (EpiMatrix; EpiVax, Inc, Providence, RI) was used to search the primary amino acid sequence of GbpB for known MHC class II binding motifs.

The motif-matching algorithms analyzed the GbpB sequence against each MHC class II allele to indicate regions of sequence that contain clusters of binding motifs. Those sequences with sufficiently high estimated binding probabilities (EBP) were used to predict MHC ligands. FIG. 1 illustrates regions of predicted epitopes as the number of motif matches associated with a given sequence. Four regions within the expressed protein sequence were identified which had at least 6 matches within the N terminal region of the expressed protein sequence. One of these regions, beginning at residue 16, fell within the 27 residue signal peptide. Three other regions in the N terminal third of the molecule began at residue 62, residue 90 and residue 121. One peptide in the C terminal region, beginning with residue 369, had 5 matches. Independent analysis of other sets of known alleles also identified these as regions with higher estimated binding probabilities. These latter analyses also showed the 10-mer region following residue 322 to have more binding potential than predicted from the results shown in FIG. 1. Table 1 indicates the peptide sequences that were identified by this method.

TABLE 1

| Amino Acid Sequence of GbpB Peptide | SEQ ID NO: |
|---|---|
| 113 KSNAATSYINAIINSKSVSD 132 | SEQ ID NO: 1 |
| KHKLITIQGQVSALQTQQAG | SEQ ID NO: 2 |
| 306 TATEAQPSASSASTAAVAAN 325 | SEQ ID NO: 3 |
| 6 LSAVLVSGVTLSSATTLSAV 25 | SEQ ID NO: 4 |
| 16 LSSATTLSAVKADDFDAQIA 35 | SEQ ID NO: 5 |
| 33 QIASQDSKINNLTAQQQAAQ 52 | SEQ ID NO: 6 |
| 37 QDSKINNLTAQQQAAQAQVN 56 | SEQ ID NO: 7 |
| 48 QQAAQAQVNTIQGQVSALQT 67 | SEQ ID NO: 8 |
| 52 QAQVNTIQGQVSALQTQQAE 71 | SEQ ID NO: 9 |
| 88 QQIQTLSSKIVARNESLKQQ 107 | SEQ ID NO: 10 |
| 117 ATSYINAIINSKSVSDAINR 136 | SEQ ID NO: 11 |
| 137 VSAIREVVSANEKMLQQQEQ 156 | SEQ ID NO: 12 |
| 174 TVAANQETIAQNTNALNTQQ 193 | SEQ ID NO: 13 |
| 194 AQLEAAQLNLQAELTTAQDQ 213 | SEQ ID NO: 14 |
| 214 KATLVAQKAAAEEAARQAAA 233 | SEQ ID NO: 15 |
| 248 ALQEQAAQAQVAANNNTQAT 267 | SEQ ID NO: 16 |
| 289 TEQSAAQAVNNSDQESTTAT 308 | SEQ ID NO: 17 |
| 311 QPSASSASTAAVAANTSSAN 330 | SEQ ID NO: 18 |
| 349 GNYWGNGGQWAASAAAAGYR 368 | SEQ ID NO: 19 |
| 365 AGYRVGSTPSAGAVAVWNDG 384 | SEQ ID NO: 20 |
| 383 DGGYGHVAYVTGVQGGQIQV 402 | SEQ ID NO: 21 |
| 403 QEANYAGNQSIGNYRGWFNP 422 | SEQ ID NO: 22 |

Peptide Constructs

MAP constructs of three 20-mer peptides (SYI, QGQ, SAS), which included the predicted binding epitopes following residues 62, 121 and 322 were synthesized using the following peptides:

```
SYI (KSNAATSYINAIINSKSVSD; GbpB residues 113-132)    (SEQ ID NO: 1)

QGQ (QAQVNTIQGQVSALQTQQAE; GbpB residues 52-71);     (SEQ ID NO: 9)
and

SAS (TATEAQPSASSASTAAVAAN; residues 306-325).        (SEQ ID NO: 3)
```

The constructs (SYI, QGQ and SAS; SEQ ID NOs. 1, 3 and 9) were selected for synthesis and further analysis based on the estimated high MHC Class II binding probability identified in the matrix-based approach described above. Peptides were synthesized (Applied Diagnostics, Foster City, Calif.) using the stepwise solid phase method of Merrifield R. B., *J. Amer. Chem. Soc.* 85:2149–2154 (1963) on a core matrix of lysines to yield macromolecules with four peptides per molecule, after the method of Tam et al., *PNAS USA* 85:5409–5413 (1988). Synthesis was successful with two of the three peptides (SYI and QGQ). Purity (>90%) was assessed using HPLC, amino acid analysis, and molecular weight determination by mass spectrometry.

Glucan Binding Protein (GbpB)

GbpB was purified from *S. mutans* strain SJr by ion exchange chromatography on MONO-Q HR 5/5 (Pharmacia) in the presence of urea. Bacteria were cultivated in sucrose-free defined medium as previously described by Navarre and Schneewind in *Mol. Microbiol.* 14:115–121 (1994). GbpB prepared in this manner migrates as a single protein band in SDS-polyacrylamide gel electrophoresis.

ELISA

Serum IgG and salivary IgA antibodies were tested by enzyme-linked immunosorbent assay (ELISA). Polystyrene microtiter plates (Flow Laboratories) were coated with 2.5 mg/ml of SYI or QGQ or 0.5 mg/ml of *S. mutans* GbpB. Antibody activity was then measured by incubation with 1:400 and 1:4000 dilutions of sera, or 1:4 dilutions of saliva. Plates were then developed for IgG antibody with rabbit anti-rat IgG, followed in sequence by alkaline phosphatase goat anti-rabbit IgG (Biosource Inc.) and p-nitrophenylphosphate (Sigma Chemical Co., St. Louis, Mo.). A mouse monoclonal reagent to rat a chain (Zymed, South San Francisco, Calif.) was used with biotinylated goat anti-mouse IgG (Zymed), followed by avidin-alkaline phosphatase (ICN Biomedicals, Inc., Auroa, Ohio), followed by p-nitrophenylphosphate to reveal levels of salivary IgA antibody to peptides. Reactivity was recorded as absorbance (A405 nm) in a micro plate reader (Biotek Instruments, Winooski, VT). Data are reported as ELISA units (EU), which were calculated relative to the levels of appropriate reference sera or salivas from Sprague Dawley rats twice immunized with the respective peptide construct. Dilutions of sera producing an A405 nm of approximately 1.0 were considered 100 EU for serum IgG antibody measurements. Dilutions of saliva producing an A405 nm of approximately 0.8 were considered 100 EU for salivary IgA antibody.

Immunogenicity of Peptides

Figure 2:
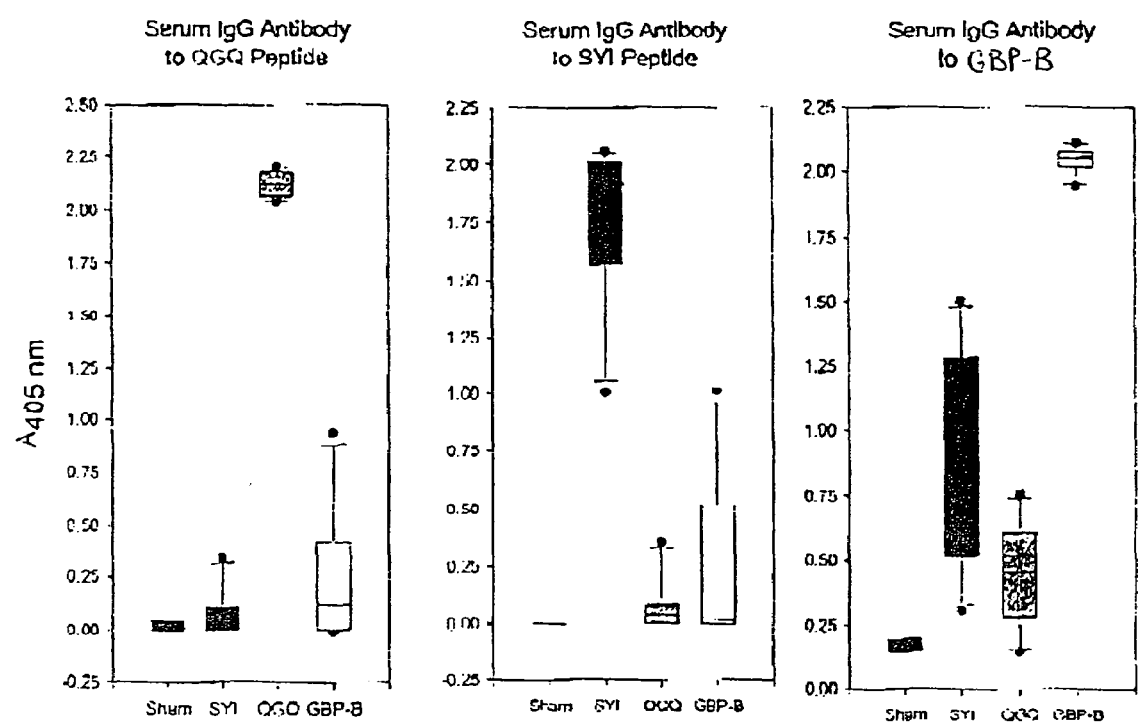
FIG. 2 depicts box plots of serum IgG antibody to GbpB peptide constructs QGQ and SYI. Serum IgG antibody activity was measured in ELISA against QGQ (left panel) and SYI (middle panel) peptide constructs and GbpB protein (right panel). Sham-immunized and SYI, QGQ- and GbpB-immunized groups represent the immune experience of 6 rats per group 35 days after the initial of two subcutaneous immunizations. The absorbency was measured at 405 nm.

Sprague Dawley CD strain 45 day-old female rats (Charles River Laboratories, Wilmington, Mass.) were used for injection. Four groups of 6 rats/group were injected subcutaneously in the vicinity of the salivary glands with 50 µg each of SYI or QGQ peptide constructs, or 10 µg of GbpB, or sham-immunized with buffer alone. The initial injection included complete Freund adjuvant (CFA; Difco Laboratories, Detroit, Mich.); one subsequent injection 21 days later included incomplete FA. Animals were bled prior to injection and 14 days after the second injection. In this experiment, rats were first momentarily anesthetized with a gas mixture of 50% carbon dioxide and 50% oxygen, and then anesthetized by intra-peritoneal injection of a mixture (0.65 ml/kg) of 3 parts ketamine (Ketaset, 100 mg/ml, Fort Dodge Lab, Ft. Dodge, Iowa) and seven parts xylazine (Rompun, 20 mg/ml, Bayer Corp., Shawnee Mission, Kans.). Saliva secretion was stimulated by subcutaneous injection of 0.6 ml carbachol (containing 0.1 mg/ml in saline; Sigma Chemical Co., St. Louis, Mo.) per kilogram of rat weight. After fluid collection, rats were injected subcutaneously first with 0.1 ml/kg of atropine sulfate (0.4 mg/ml; American Pharmaceutical Partners, Inc., Los Angeles, Calif.) and then with yohimbine (yobine, 2.0 mg/ml; Lloyd Laboratories, Shenandoah, Id.) at a volume equal to 1.4 times that used for anesthesia. Sera from coagulated and centrifuged blood were stored frozen at −20° C. until measurement of antibody activity. Serum taken thirty-five days after the first injection was analyzed in ELISA for serum IgG antibody levels to each peptide construct and to GbpB (FIG. 2).

All rats injected with the QGQ peptide responded with high levels of serum antibody to the QGQ peptide, whereas no significant response to QGQ epitopes were seen in sham immunized rats or rats injected with SYI. Interestingly, the sera from two of the four rats injected with GbpB protein also reacted with QGQ.

All rats injected with the SYI peptide also demonstrated elevated levels of serum IgG antibody to the inciting SYI MAP peptide construct, in contrast to sham- or QGQ-injected rats. Again, serum IgG from one of the four rats injected with the parent GbpB protein also showed a significant reaction with the SYI peptide.

All sera were also evaluated in ELISA using plates coated with GbpB. Rats from SYI (6/6) or QGQ (4/6) peptide-injected groups reacted with the parent GbpB protein. Although the levels of serum IgG antibody from peptide-injected rats that were reactive with GbpB did not achieve levels from protein-injected rats, the overall response in the SYI-injected rats to native GbpB epitopes was significant. Taken together, these results supported the immunogenicity of these peptides predicted using the bioinformatics approach. Furthermore, they also suggested that the linear epitope(s) found especially on the SYI peptide construct were shared with those on the intact parent GbpB protein.

Protective Immunity

Peptides and multiple-epitope peptide constructs were tested in an art-recognized rat model for human dental caries. The SYI peptide was selected to test this assumption since this peptide induced more consistent immune responses reactive with GbpB than did the QGQ peptide.

Two groups (n=13/group) of 25 day-old Sprague-Dawley female rats were singly caged. Rats were subcutaneously (sc) injected in the salivary gland vicinity with 50 µg of SYI MAP peptide construct or phosphate buffered saline (control animals). Antigen was incorporated with complete Freund's adjuvant (CFA). Nine days later, rats were reinjected with PBS or with SYI at the same dose in incomplete FA. Six days after the second injection, blood and saliva was collected under anesthesia described above. About fifteen days after the second injection, rats were placed in tubs (6 rats/tub), given diet 2000, and orally infected with approximately $10^8$ S. mutans SJ32 for 3 consecutive days. Rats were again singly caged after the infection protocol was completed and continued on diet 2000 for the duration of the experiment. Blood and saliva were collected 78 days after initial infection, followed by sacrifice. In preparation for the scoring of dental caries, rat skulls were defleshed by dermaphagic beetles, followed by a rinse with 70% ethanol.

Figure 3:
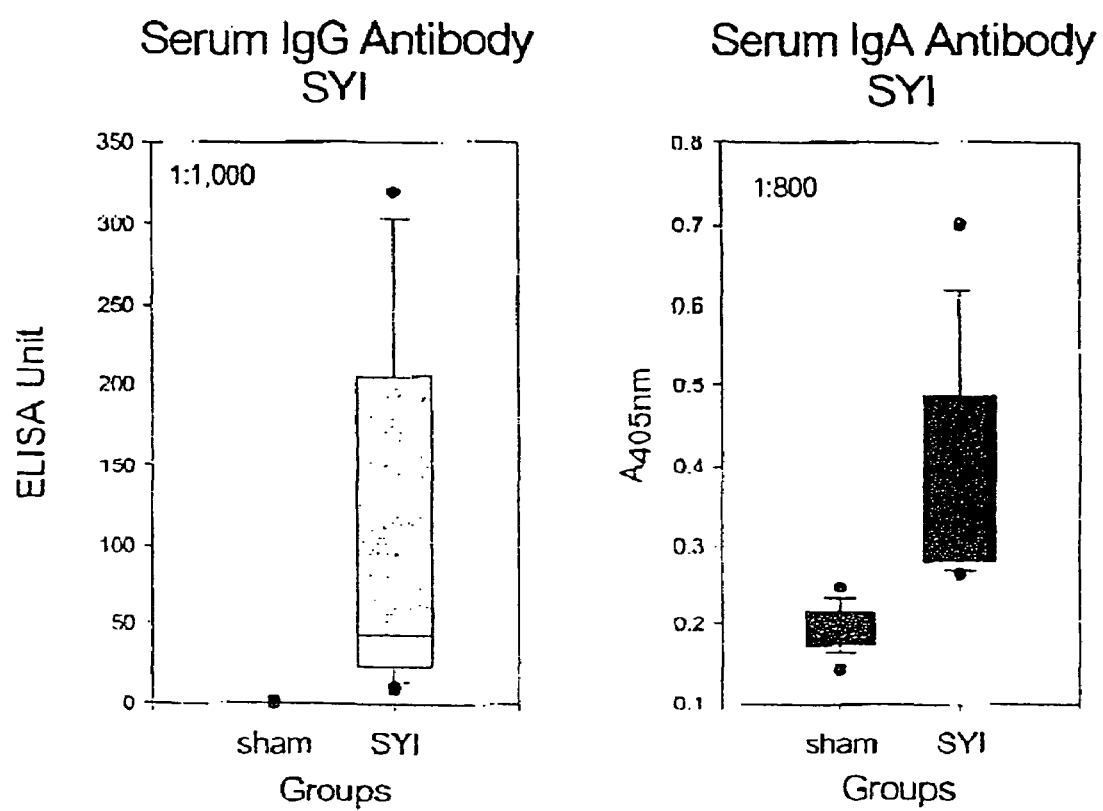
FIG. 3 depicts box plots of serum IgG and IgA antibody to SYI in the protection experiment. IgG (left panel) and IgA (right panel) antibody activity was measured in ELISA against SYI in sera collected at the end of the protection experiment. Sham-immunized and SYI-immunized groups represent the immune experience of 13 rats per group three months after the initial of two subcutaneous immunizations. The absorbency was measured at 405 nm.
Figure 4:
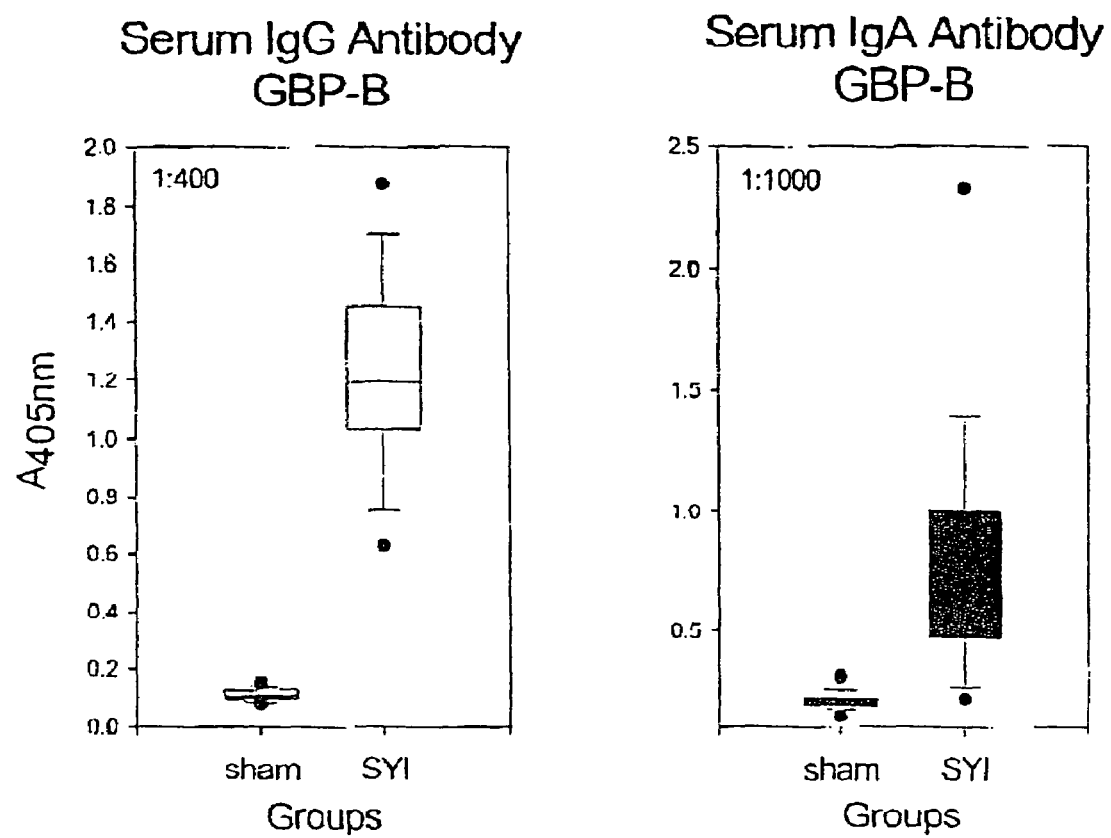
FIG. 4 depicts box plots of serum IgG and IgA antibody to GbpB in the protection experiment. IgG (left panel) and IgA (right panel) antibody activity was measured in ELISA against GbpB in sera collected at the end of the protection experiment. Sham-immunized and SYI-immunized groups represent the immune experience of 13 rats/per group three months after the initial of two subcutaneous immunizations. The absorbency was measured at 405 nm.

Sera collected at the end of the 78 day infection period were analyzed for IgG and IgA antibody to both the peptide construct (FIG. 3) and to GbpB (FIG. 4). As expected, immunization with the peptide induced serum antibody in both isotypes to the inciting SYI peptide. Also, consistent with the previous experiment, SYI immunization also induced IgG antibody to intact GbpB in all rats, although some rats did not demonstrate serum IgA antibody levels to GbpB, at least at the dilutions tested. Saliva was collected prior to infection and at the end of the experiment was analyzed in ELISA for IgA antibody to SYI and GbpB (Table 2). Several (5/13) SYI-immunized rats demonstrated induction of salivary IgA antibody to both the peptide and the intact protein at either time point, although group levels were not significantly different under the conditions of measurement.

TABLE 2

| Group | Test Antigen | Mean EU | SE |
|---|---|---|---|
| Sham-immunized | GbpB | 7.1 | 5.1 |
| SYI-immunized | GbpB | 31.1 | 16.5 |
| Sham-immunized | SYI | 3.6 | 2.4 |
| SYI-immunized | SYI | 12.5 | 5.9 |

Figure 5:
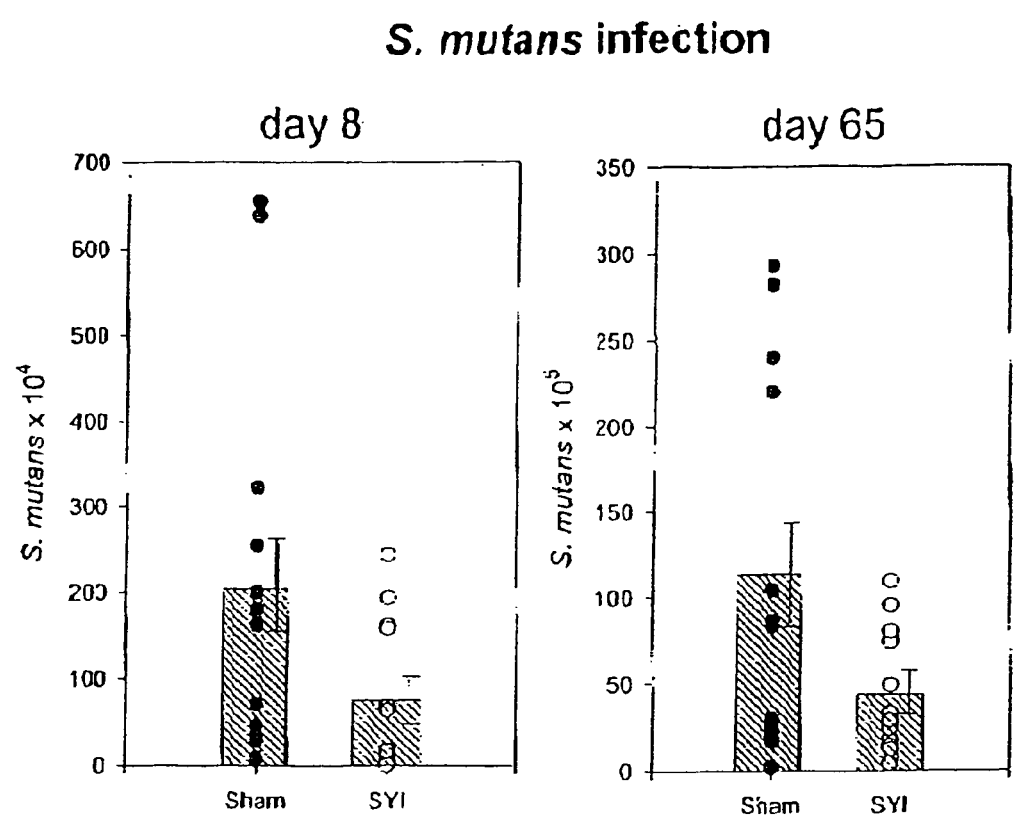
FIG. 5 depicts the level of infection after challenge with S. mutans. Each plot represents the number of S. mutans SJr cultivated after systematic swabbing of molar surfaces eight days and 65 days after initial infection with S. mutans SJr. Bars indicate the mean colony forming units of S. mutans SJr in sham- or SYI-immunized groups. Open and closed circles indicate levels of infection of individual rats.
Figure 6:
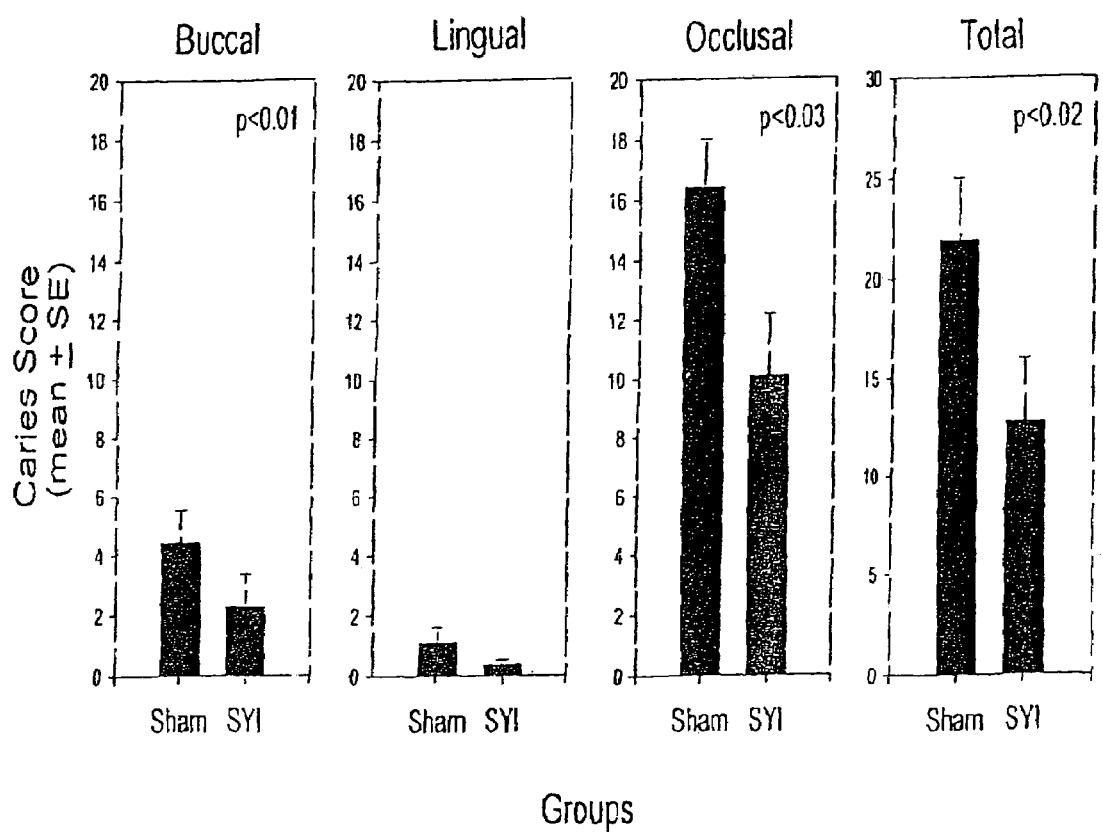
FIG. 6 depicts dental caries after 78 days of infection with S. mutans SJr. The buccal, lingual, occlusal and total molar caries scores for sham and SYI-immunized groups are shown in respective panels.

The protective response of the SYI immunization was evaluated by systematic swabbing of molar teeth for S. mutans infection (FIG. 5) and measurement of caries on molar surfaces (FIG. 6).

Bacterial Recoveries

The mutans streptococcal flora was assessed at 70 days after infection. After systematic swabbing of teeth, sonication, and plating appropriate dilutions on mitis salivarius agar (MS; total streptococci), and MS agar with 0.2 mg/ml streptomycin sulfate (MSS; Streptococcus mutans strain SJr), plates were incubated for 48 hours at 37° C. in 90% $N_2$, 10% $CO_2$. S. mutans colony forming units (CFU) were then enumerated microscopically on MSS agar.

Caries Assessment

The extent and depth of carious lesions in all rat molar teeth (caries score) were microscopically evaluated by standard methods. Caries scores were determined separately on smooth and on occlusal dental surfaces. Thus, measurements of protective influence of immunization support the conservation of at least one epitope on SYI capable of inducing a caries-protective response in this model. The mean levels of infecting (streptomycin tolerant) S. mutans SJr recovered from SYI-immunized groups were lower than sham-immunized group recoveries both eight and 65 days after infection was initiated, although these differences did not achieve statistical significance at the p <0.05 level because of the variation in bacterial recoveries. The trend in the infection data was supported by measurements of dental caries. Caries scores on smooth (buccal) and occlusal surfaces as well as total caries scores of SYI-peptide immunized rats were significantly lower than those of sham-immunized and infected rats (FIG. 6).

EXAMPLE 2

Diepitopic Immunization Studies

GTF and glucan binding protein B (GbpB) from mutans streptococci have each been implicated in the molecular pathogenesis of dental caries caused by these organisms. Native GTF and GbpB, as well as synthetic peptides derived from each protein, have been shown to induce protective immune responses to infection with cariogenic mutans streptococci in experimental models.

Two diepitopic synthetic peptide constructs were synthesized in a MAP format. Both peptides contained SYI, a 20-mer sequence from GbpB that bioinformatic analyses indicated was similar in sequence to an MHC class II binding peptide. One diepitopic peptide (SYI-CAT) also contained a 22-mer sequence from the catalytic domain of GTF. The other diepitopic construct (SYI-GLU) contained a 22-mer sequence from the glucan binding domain of GTF.

Diepitopic and monoepitopic MAP constructs were synthesized by AnaSpec, Inc. (San Jose, Calif.). Eight groups of Sprague-Dawley rats (n=4–8/group) were initially injected subcutaneously with one the following, together with complete Freund adjuvant: (1) buffer alone, (2) MAP-CAT, (3) MAP-GLU, (4) MAP-SYI, (5) MAP-CATGTF-SYIGbpB, (6) MAP-GLUGTF-SYIGbpB, (7) S. mutans GbpB, or (8) S. sobrinus GTF. On day 21, the 8 groups were again injected with the same contents, except the second injections substituted incomplete Freund adjuvant. Animals were then bled and salivated on days 42 and 63. Sera were tested for antibody activity against peptides and proteins using an alkaline phosphatase enzyme-linked immunosorbent assay (ELISA). Antibody levels were compared using one and two way ANOVA, followed by Dunn's multiple comparison test.

Sera from blood taken 42 days after the second injection were examined for IgG antibody activity against constituent peptides or native proteins. The serum IgG response to GLU was similar whether SYI-GLU or GLU alone was used for injection. In contrast, SYI-CAT induced an IgG response to CAT that was significantly higher than that induced by CAT alone. Both diepitopic peptide constructs induced IgG antibody that reacted with GTF and GbpB native proteins. Sera from SYI-CAT-immunized animals reacted with GTF to a significantly greater degree than SYI-GLU. These results indicate that diepitopic synthetic peptides, especially SYI-CAT, induce an immune response that provides a broader range of protective antibody epitopes in a subunit dental caries vaccine. Furthermore, these results indicate that the combination of SYI with CAT potentiated the immune response to this important GTF catalytic domain.

Sequences Used in Diepitopic Immunization Studies:

1. GTF-derived catalytic (CAT) peptide: DANFDSIRVDAVDNVDADLLQI (SEQ ID NO:25)

2. GTF-derived glucan binding (GLU) peptide: TGAQTIKGQKLYFKANGQQVKG (SEQ ID NO:23)

3. GbpB-derived MHC class II (SYI) peptide: KSNAATSYINAIINSKSVSD (SEQ ID NO:1)

4. Diepitopic SYI-CAT peptide, two copies of each in multiple antigenic peptide (MAP) format:

KSNAATSYINAIINSKSVSD (SEQ ID NO:1)—DANFDSIRVDAVDNVDADLLQI (SEQ ID NO:25)

5. Diepitopic SYI-GLU peptide, two copies of each in multiple antigenic peptide (MAP) format:

KSNAATSYINAIINSKSVSD (SEQ ID NO:1)—TGAQTIKGQKLYFKANGQQVKG (SEQ ID NO:23)

Results of Diepitopic Immunization Studies:

Sera were tested at a 1:200 dilution in groups of 4–7 rats.

Both diepitopic constructs induce significant antibody to Gbp-B (Table 3).

TABLE 3

Serum IgG responses to GBP-b (glucan binding protein B)

| Group | Serum IgG antibody to GbpB Mean ± SE |
|---|---|
| Sham | 0.027 ± 0.014 |
| SYI-CAT | 0.783 ± 0.268 |
| SYI-GLU | 0.847 ± 0.186 |
| SYI | 0.599 ± 0.201 |
| CAT | 0.029 ± 0.009 |
| GLU | 0.022 ± 0.009 |
| GluB | 1.838 ± 0.052 |

Figure 7:
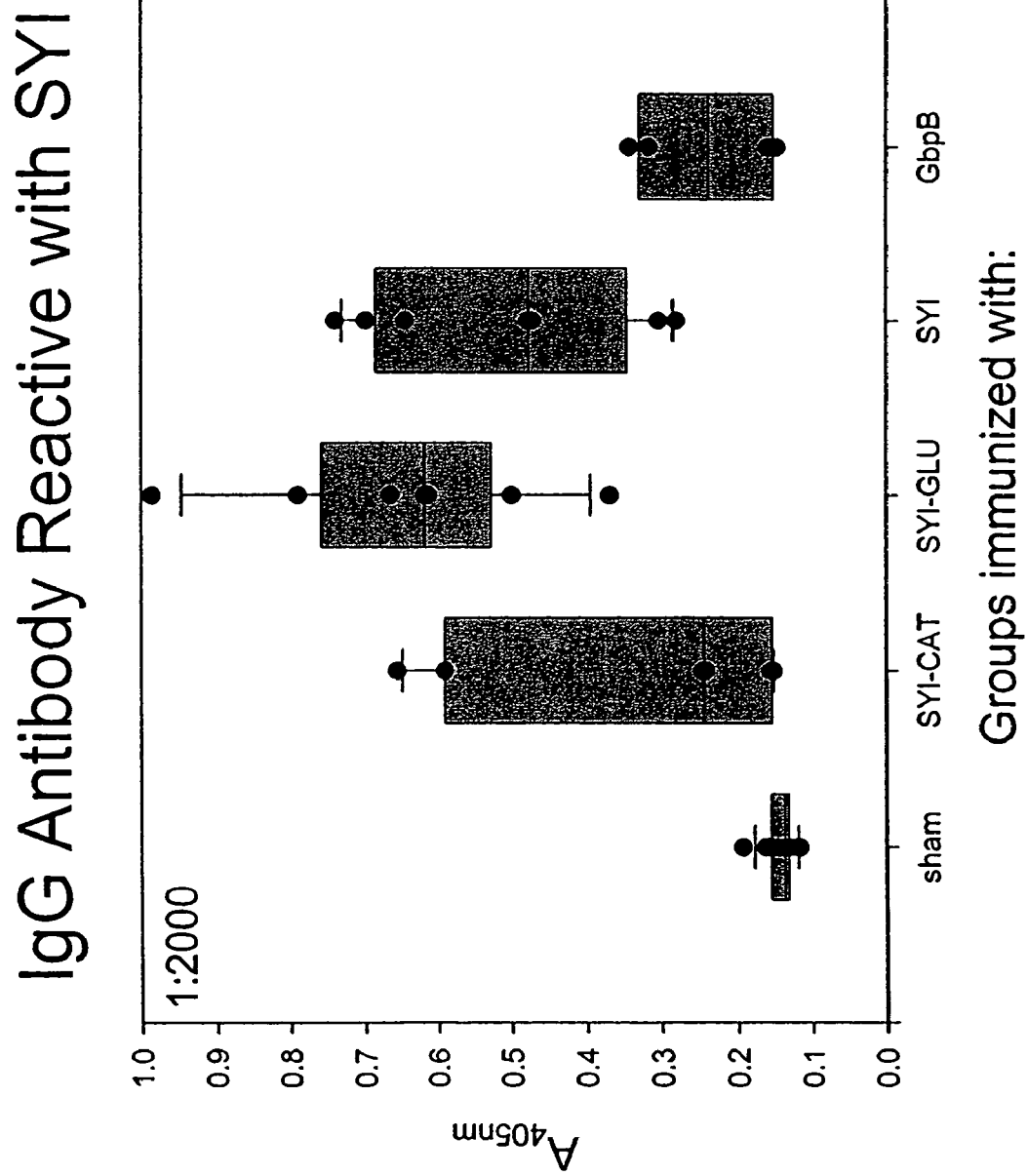
FIG. 7 is a box plot showing serum IgG antibody binding to SYI peptide depicted as absorbency units at 405 nm as measured in an ELISA assay. Sera was collected on day 63.
Figure 8:
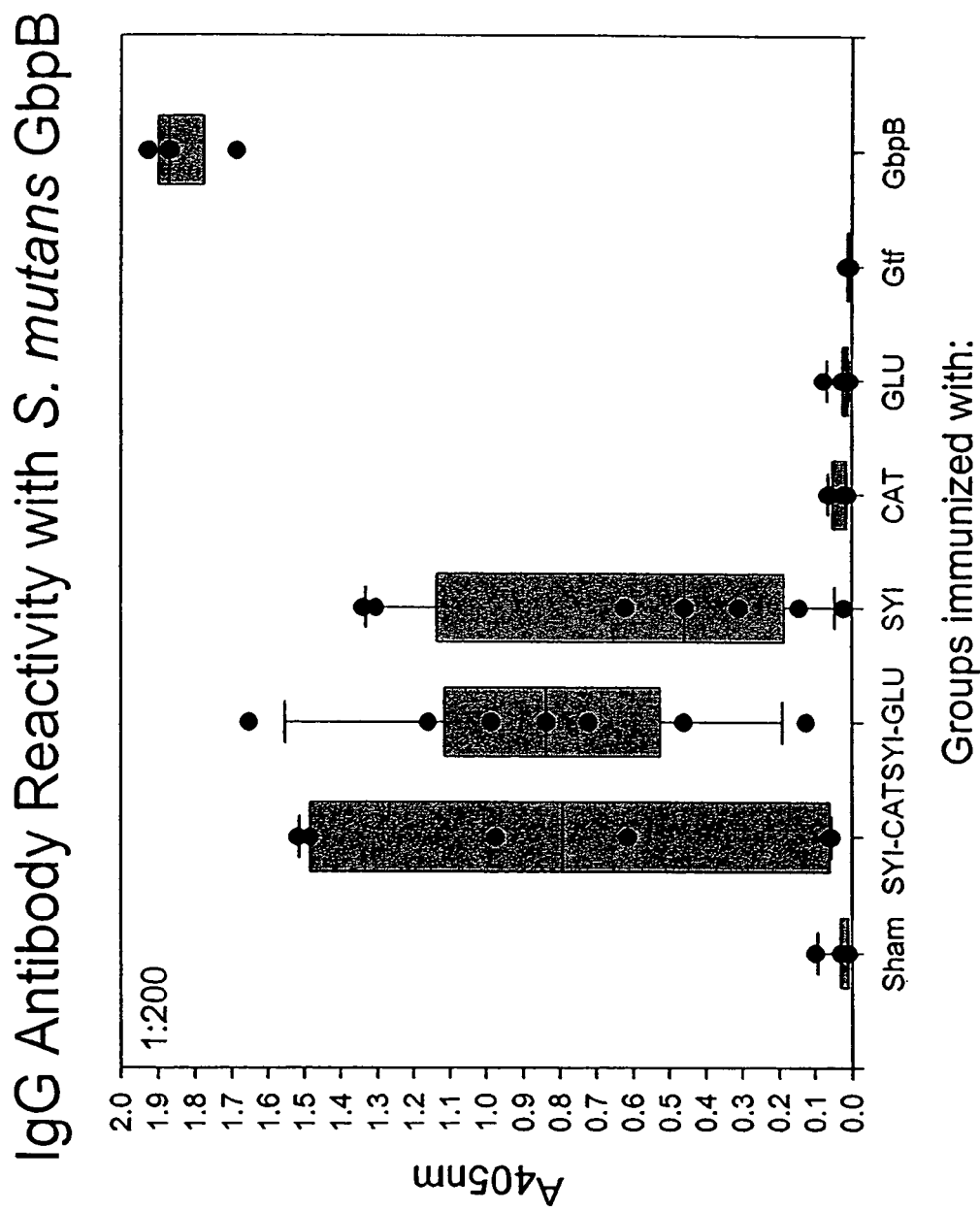
FIG. 8 is a box plot showing serum IgG antibody binding to *S. mutans* GbpB depicted as absorbency units at 405 nm as measured in an ELISA assay. Sera was collected on day 63.
Figure 9:
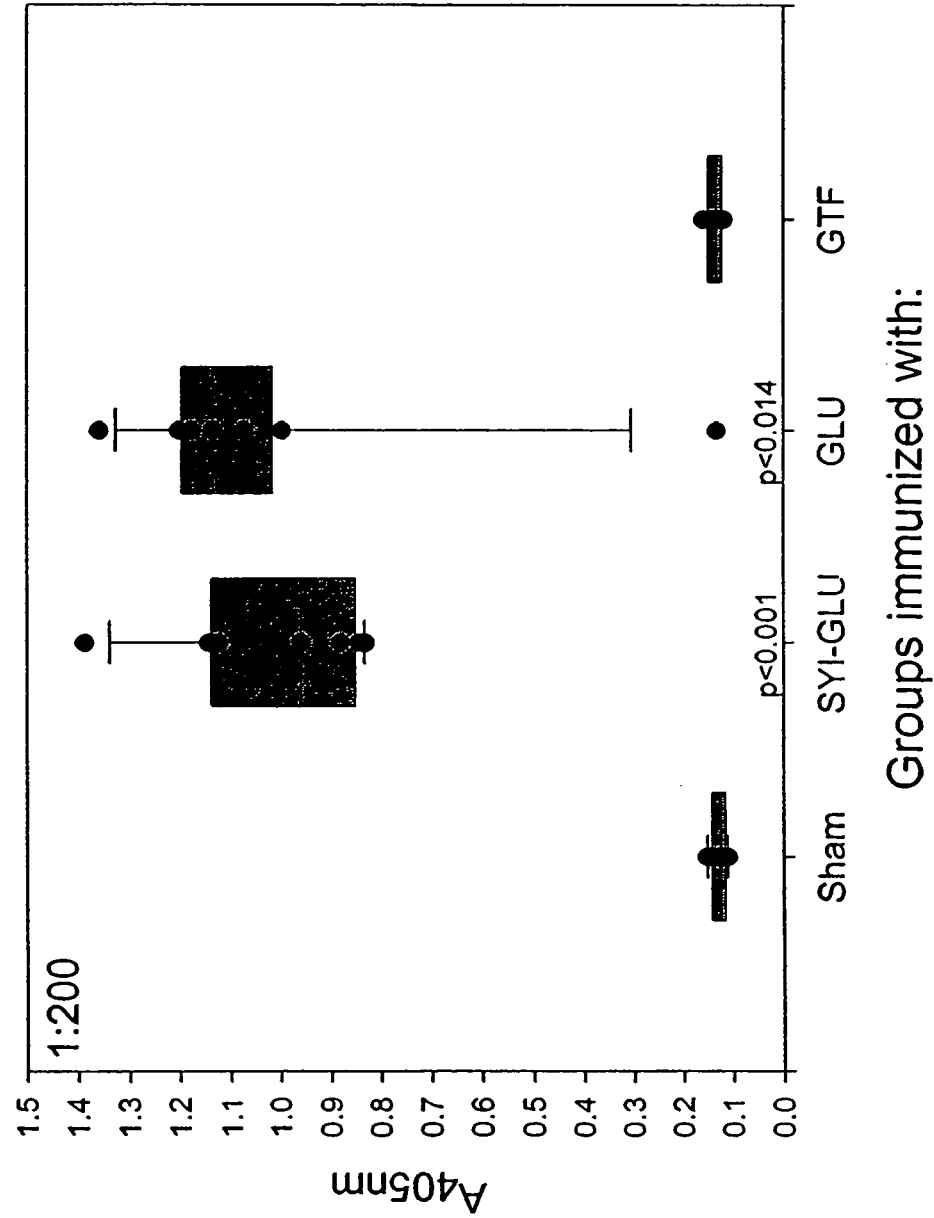
FIG. 9 is a box plot showing serum IgG antibody binding to GLU peptide depicted as absorbency units at 405 nm as measured in an ELISA assay. Sera was collected on day 63.

The SYI-GLU diepitopic construct enhances anti-peptide (SYI) and anti-glucan binding protein responses (FIG. 7). Rats immunized with either diepitopic construct develop antibody to the parent GbpB protein (FIG. 8).

Figure 10:
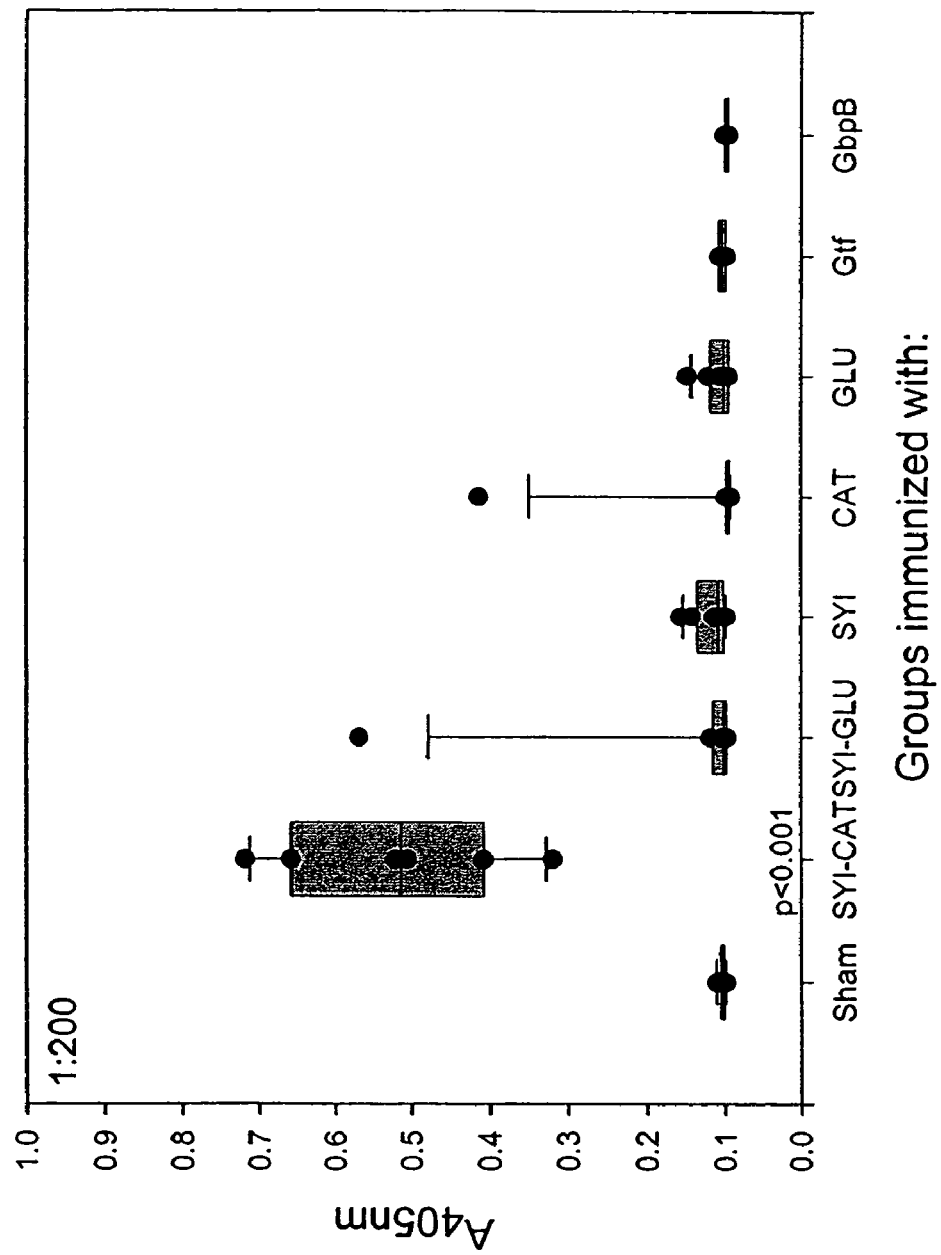
FIG. 10 is a box plot showing serum IgG antibody binding to CAT peptide depicted as absorbency units at 405 nm as measured in an ELISA assay. Sera was collected on day 63.
Figure 11:
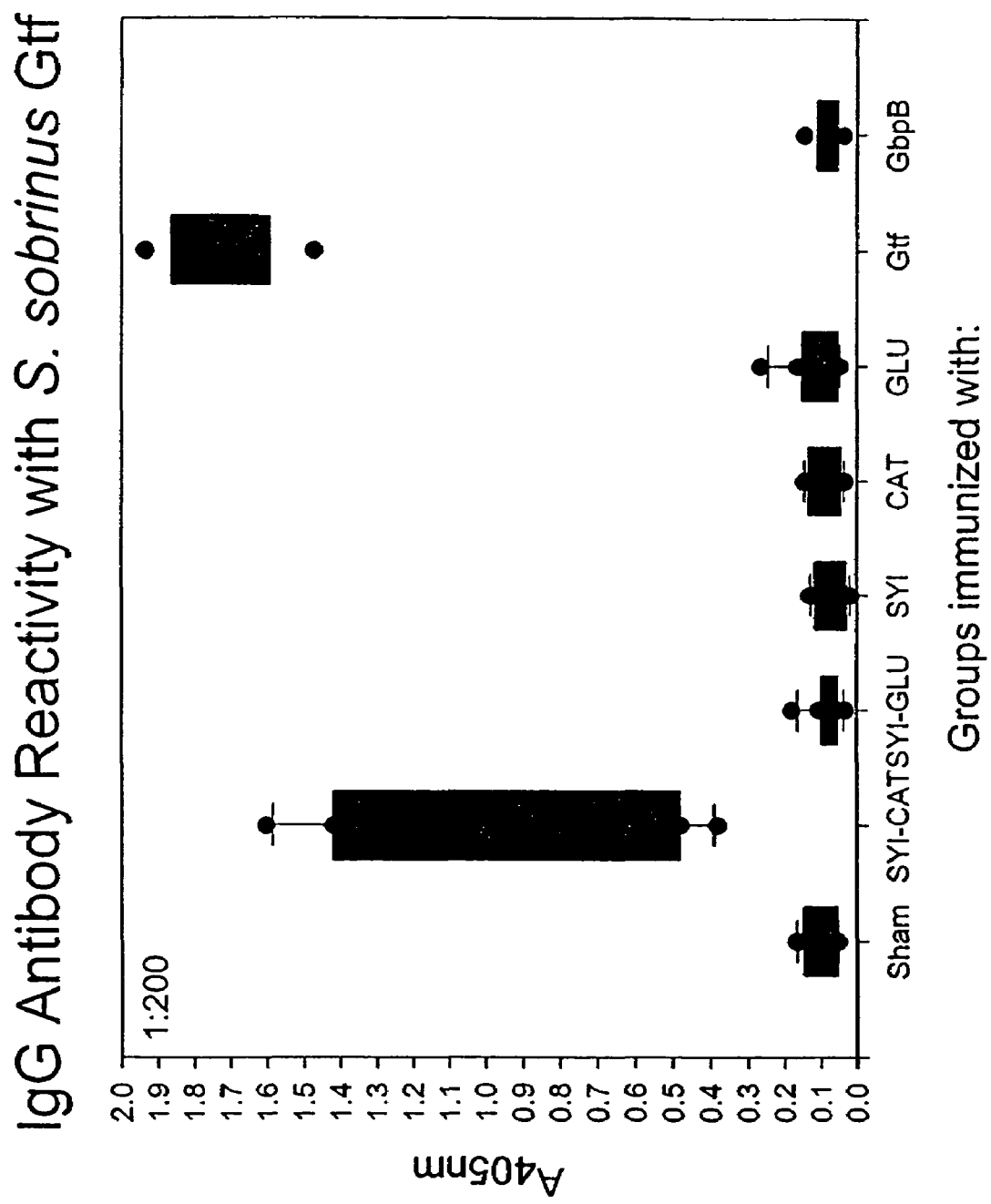
FIG. 11 is a box plot showing serum IgG antibody binding to *S. sobrinus* GTF depicted as absorbency units at 405 nm as measured in an ELISA assay. Sera was collected on day 63.
Figure 12:
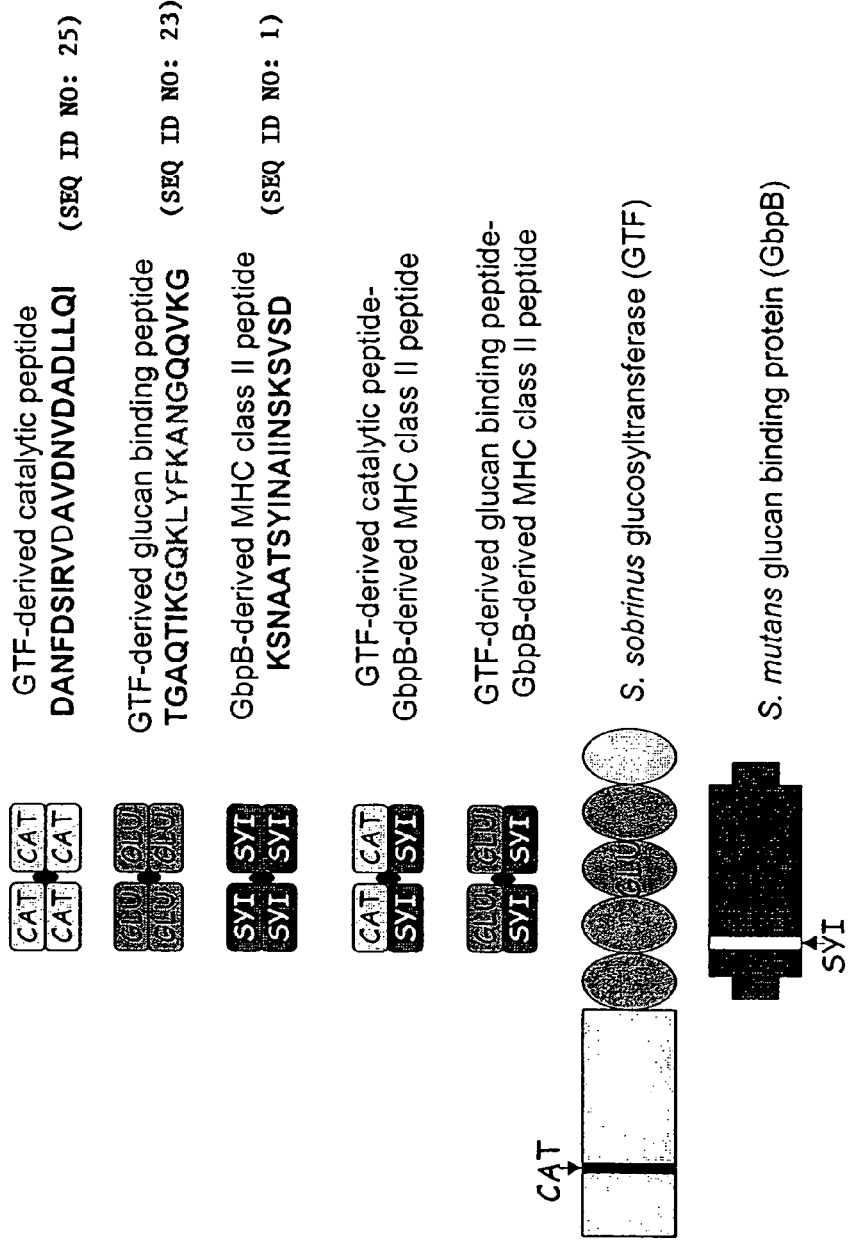
FIG. 12 is a pictorial representation of the peptide and protein antigens used for the immunization of rats in the ELISA binding assays (results of which are shown in FIGS. 7–11).

The SYI-CAT diepitopic construct significantly enhances the anti-peptide (CATI) responses over the mono-epitopic MAP (FIG. 10). Only the SYI-CAT diepitopic construct induced significant IgG antibody to the parent GTF protein in all rats (FIG. 11), and thus was the most efficient stimulus for antibody to both virulence antigens. Furthermore, the SYI-CAT diepitopic construct alone induced a significant serum IgG immune response to GTF in all animals (Table 4).

TABLE 4

Serum IgG responses to GTF

| Group | Serum IgG antibody to GTF Mean ± SE |
|---|---|
| Sham | 0.114 ± 0.029 |
| SYI-CAT | 0.955 ± 0.200 |
| SYI-GLU | 0.083 ± 0.018 |
| SYI | 0.073 ± 0.018 |
| CAT | 0.088 ± 0.018 |
| GLU | 0.108 ± 0.031 |
| GTF | 1.728 ± 0.098 |

The SYI-CAT construct induces significant levels of serum IgG antibody to both GbpB and GTF virulence antigens of *mutans streptococci*. In addition, the diepitopic construct enhanced the immune response to the CAT epitopes over that observed when monoepitopic CAT construct is used. Thus the SYI-CAT construct reduces the pathogenicity of *Streptococcus mutans* by inhibiting enzymatic activity (glucan formation) and inhibiting activity of glucan binding protein B.

All references cited herein are incorporated by reference in their entirety. While this invention has been particularly shown and described with references to preferred embodiments thereof, it will be understood by those skilled in the art that various changes in form and details may be made therein without departing from the scope of the invention encompassed by the appended claims.

---

What is claimed is:

1. A composition comprising a fragment of a glucan binding protein-B (GbpB), wherein said fragment binds to a major histocompatibility complex (MHC) class II protein.

2. The composition of claim 1, wherein said fragment binds to an HLA protein.

3. The composition of claim 1, wherein said fragment binds to an HLA protein selected from the group consisting of DRA, DRB1, DRB2, DQA1, DQB1, DPA1, DPB1, DMA, DMB, DOA, and DOB.

4. The composition of claim 1, wherein said fragment binds to an HLA protein, and wherein said HLA protein is DRB1.

5. The composition of claim 1, wherein said fragment of a GbpB protein comprises an amino acid sequence selected from the group consisting of SEQ ID NO's: 29, 30, 31, 32, and 33.

6. The composition of claim 1, wherein said fragment of a GbpB protein comprises the amino acid sequence of SEQ ID NO: 29.

7. The composition of claim 1, wherein said fragment is greater than 6 and less than 431 residues in length.

8. The composition of claim 1, wherein said fragment is less than 400 residues in length.

9. The composition of claim 1, wherein said fragment is less than 100 residues in length.

10. The composition of claims 1, wherein said fragment is 10–25 residues in length.

11. The composition of claim 1, wherein said fragment comprises an amino acid sequence selected from the group consisting of SEQ ID NO's: 1, 2, 3, 4, 5, 6, 7, 8, 9, 10, 11, 12, 13, 14, 15, 16, 17, 18, 19, 20, 21, 22, and 41.

12. The composition of claim 1, wherein said fragment comprises an amino acid sequence selected from the group consisting of SEQ ID NO's: 1 and 3.

13. A composition comprising a GbpB polypeptide and a glucosyltransferase polypeptide.

14. The composition of claim 13, wherein said GbpB polypeptide comprises an amino acid sequence selected from the group consisting of SEQ ID NO's: 1, 2, 3, 4, 5, 6, 7, 8, 9, 10, 11, 12, 13, 14, 15, 16, 17, 18, 19, 20, 21, 22, and 41.

15. The composition of claim 13, wherein said GbpB polypeptide comprises an amino acid sequence selected from the group consisting of SEQ ID NO: 1 and SEQ ID NO: 3.

16. The composition of claim 13, wherein said glucosyltransferase polypeptide comprises a catalytic domain selected from the group consisting of SEQ ID NO: 34, 35, 36, 37, 38, 39, and 40.

17. The composition of claim 16, wherein said catalytic domain comprises an amino acid sequence selected from the group consisting of SEQ ID NO: 24 and SEQ ID NO: 25.

18. The composition of claim 13, wherein said glucosyltransferase polypeptide comprises a glucan binding domain selected from the group consisting of SEQ ID NO: 34, 35, 36, 37, 38, 39, and 40.

19. The composition of claim 13, wherein said glucosyltransferase polypeptide comprises the amino acid sequence of SEQ ID NO: 23.

20. The composition of claim 13, wherein said glucosyltransferase polypeptide comprises an amino acid sequence selected from the group consisting of SEQ ID NO: 23, 24, 25, 26, 27, and 28.

21. The composition of claim 13, wherein said GbpB polypeptide comprises SEQ ID NO: 1 and said glucosyltransferase polypeptide comprises SEQ ID NO: 23.

22. The composition of claim 13, wherein said GbpB polypeptide comprises SEQ ID NO: 1 and said glucosyltransferase polypeptide comprises SEQ ID NO: 25.

23. The composition of claim 13, wherein said composition further comprises a peptidyl core matrix.

24. The composition of claim 23, wherein said core matrix comprises at least one lysine.

25. The composition of claim 23, wherein said core matrix comprises a plurality of lysine residues.

* * * * *

SEQUENCE LISTING

<160> NUMBER OF SEQ ID NOS: 41

<210> SEQ ID NO 1
<211> LENGTH: 20
<212> TYPE: PRT
<213> ORGANISM: Streptococcus mutans

<400> SEQUENCE: 1

Lys Ser Asn Ala Ala Thr Ser Tyr Ile Asn Ala Ile Ile Asn Ser Lys
1               5                   10                  15

Ser Val Ser Asp
            20

<210> SEQ ID NO 2

```
<211> LENGTH: 20
<212> TYPE: PRT
<213> ORGANISM: Streptococcus mutans

<400> SEQUENCE: 2

Lys His Lys Leu Ile Thr Ile Gln Gly Gln Val Ser Ala Leu Gln Thr
1               5                   10                  15

Gln Gln Ala Gly
            20

<210> SEQ ID NO 3
<211> LENGTH: 20
<212> TYPE: PRT
<213> ORGANISM: Streptococcus mutans

<400> SEQUENCE: 3

Thr Ala Thr Glu Ala Gln Pro Ser Ala Ser Ser Ala Ser Thr Ala Ala
1               5                   10                  15

Val Ala Ala Asn
            20

<210> SEQ ID NO 4
<211> LENGTH: 20
<212> TYPE: PRT
<213> ORGANISM: Streptococcus mutans

<400> SEQUENCE: 4

Leu Ser Ala Val Leu Val Ser Gly Val Thr Leu Ser Ser Ala Thr Thr
1               5                   10                  15

Leu Ser Ala Val
            20

<210> SEQ ID NO 5
<211> LENGTH: 20
<212> TYPE: PRT
<213> ORGANISM: Streptococcus mutans

<400> SEQUENCE: 5

Leu Ser Ser Ala Thr Thr Leu Ser Ala Val Lys Ala Asp Asp Phe Asp
1               5                   10                  15

Ala Gln Ile Ala
            20

<210> SEQ ID NO 6
<211> LENGTH: 20
<212> TYPE: PRT
<213> ORGANISM: Streptococcus mutans

<400> SEQUENCE: 6

Gln Ile Ala Ser Gln Asp Ser Lys Ile Asn Asn Leu Thr Ala Gln Gln
1               5                   10                  15

Gln Ala Ala Gln
            20

<210> SEQ ID NO 7
<211> LENGTH: 20
<212> TYPE: PRT
<213> ORGANISM: Streptococcus mutans

<400> SEQUENCE: 7

Gln Asp Ser Lys Ile Asn Asn Leu Thr Ala Gln Gln Gln Ala Ala Gln
1               5                   10                  15
```

```
Ala Gln Val Asn
            20

<210> SEQ ID NO 8
<211> LENGTH: 20
<212> TYPE: PRT
<213> ORGANISM: Streptococcus mutans

<400> SEQUENCE: 8

Gln Gln Ala Ala Gln Ala Gln Val Asn Thr Ile Gln Gly Gln Val Ser
1               5                   10                  15

Ala Leu Gln Thr
            20

<210> SEQ ID NO 9
<211> LENGTH: 20
<212> TYPE: PRT
<213> ORGANISM: Streptococcus mutans

<400> SEQUENCE: 9

Gln Ala Gln Val Asn Thr Ile Gln Gly Gln Val Ser Ala Leu Gln Thr
1               5                   10                  15

Gln Gln Ala Glu
            20

<210> SEQ ID NO 10
<211> LENGTH: 20
<212> TYPE: PRT
<213> ORGANISM: Streptococcus mutans

<400> SEQUENCE: 10

Gln Gln Ile Gln Thr Leu Ser Ser Lys Ile Val Ala Arg Asn Glu Ser
1               5                   10                  15

Leu Lys Gln Gln
            20

<210> SEQ ID NO 11
<211> LENGTH: 20
<212> TYPE: PRT
<213> ORGANISM: Streptococcus mutans

<400> SEQUENCE: 11

Ala Thr Ser Tyr Ile Asn Ala Ile Ile Asn Ser Lys Ser Val Ser Asp
1               5                   10                  15

Ala Ile Asn Arg
            20

<210> SEQ ID NO 12
<211> LENGTH: 20
<212> TYPE: PRT
<213> ORGANISM: Streptococcus mutans

<400> SEQUENCE: 12

Val Ser Ala Ile Arg Glu Val Val Ser Ala Asn Glu Lys Met Leu Gln
1               5                   10                  15

Gln Gln Glu Gln
            20

<210> SEQ ID NO 13
<211> LENGTH: 20
<212> TYPE: PRT
<213> ORGANISM: Streptococcus mutans
```

-continued

```
<400> SEQUENCE: 13

Thr Val Ala Ala Asn Gln Glu Thr Ile Ala Gln Asn Thr Asn Ala Leu
1               5                   10                  15

Asn Thr Gln Gln
            20

<210> SEQ ID NO 14
<211> LENGTH: 20
<212> TYPE: PRT
<213> ORGANISM: Streptococcus mutans

<400> SEQUENCE: 14

Ala Gln Leu Glu Ala Ala Gln Leu Asn Leu Gln Ala Glu Leu Thr Thr
1               5                   10                  15

Ala Gln Asp Gln
            20

<210> SEQ ID NO 15
<211> LENGTH: 20
<212> TYPE: PRT
<213> ORGANISM: Streptococcus mutans

<400> SEQUENCE: 15

Lys Ala Thr Leu Val Ala Gln Lys Ala Ala Glu Glu Ala Ala Arg
1               5                   10                  15

Gln Ala Ala Ala
            20

<210> SEQ ID NO 16
<211> LENGTH: 20
<212> TYPE: PRT
<213> ORGANISM: Streptococcus mutans

<400> SEQUENCE: 16

Ala Leu Gln Glu Gln Ala Ala Gln Ala Gln Val Ala Ala Asn Asn Asn
1               5                   10                  15

Thr Gln Ala Thr
            20

<210> SEQ ID NO 17
<211> LENGTH: 20
<212> TYPE: PRT
<213> ORGANISM: Streptococcus mutans

<400> SEQUENCE: 17

Thr Glu Gln Ser Ala Ala Gln Ala Val Asn Asn Ser Asp Gln Glu Ser
1               5                   10                  15

Thr Thr Ala Thr
            20

<210> SEQ ID NO 18
<211> LENGTH: 20
<212> TYPE: PRT
<213> ORGANISM: Streptococcus mutans

<400> SEQUENCE: 18

Gln Pro Ser Ala Ser Ser Ala Ser Thr Ala Ala Val Ala Ala Asn Thr
1               5                   10                  15

Ser Ser Ala Asn
            20
```

```
<210> SEQ ID NO 19
<211> LENGTH: 20
<212> TYPE: PRT
<213> ORGANISM: Streptococcus mutans

<400> SEQUENCE: 19

Gly Asn Tyr Trp Gly Asn Gly Gly Gln Trp Ala Ala Ser Ala Ala Ala
1               5                   10                  15

Ala Gly Tyr Arg
            20

<210> SEQ ID NO 20
<211> LENGTH: 20
<212> TYPE: PRT
<213> ORGANISM: Streptococcus mutans

<400> SEQUENCE: 20

Ala Gly Tyr Arg Val Gly Ser Thr Pro Ser Ala Gly Ala Val Ala Val
1               5                   10                  15

Trp Asn Asp Gly
            20

<210> SEQ ID NO 21
<211> LENGTH: 20
<212> TYPE: PRT
<213> ORGANISM: Streptococcus mutans

<400> SEQUENCE: 21

Asp Gly Gly Tyr Gly His Val Ala Tyr Val Thr Gly Val Gln Gly Gly
1               5                   10                  15

Gln Ile Gln Val
            20

<210> SEQ ID NO 22
<211> LENGTH: 20
<212> TYPE: PRT
<213> ORGANISM: Streptococcus mutans

<400> SEQUENCE: 22

Gln Glu Ala Asn Tyr Ala Gly Asn Gln Ser Ile Gly Asn Tyr Arg Gly
1               5                   10                  15

Trp Phe Asn Pro
            20

<210> SEQ ID NO 23
<211> LENGTH: 22
<212> TYPE: PRT
<213> ORGANISM: Streptococcus mutans

<400> SEQUENCE: 23

Thr Gly Ala Gln Thr Ile Lys Gly Gln Lys Leu Tyr Phe Lys Ala Asn
1               5                   10                  15

Gly Gln Gln Val Lys Gly
            20

<210> SEQ ID NO 24
<211> LENGTH: 21
<212> TYPE: PRT
<213> ORGANISM: Streptococcus mutans

<400> SEQUENCE: 24

Asp Ala Asn Phe Asp Ser Ile Arg Val Asp Ala Val Asp Asn Val Asp
1               5                   10                  15
```

```
Ala Asp Leu Leu Gln
            20

<210> SEQ ID NO 25
<211> LENGTH: 22
<212> TYPE: PRT
<213> ORGANISM: Streptococcus mutans

<400> SEQUENCE: 25

Asp Ala Asn Phe Asp Ser Ile Arg Val Asp Ala Val Asp Asn Val Asp
1               5                   10                  15

Ala Asp Leu Leu Gln Ile
            20

<210> SEQ ID NO 26
<211> LENGTH: 25
<212> TYPE: PRT
<213> ORGANISM: Streptococcus mutans

<400> SEQUENCE: 26

Pro Leu Asp Lys Arg Ser Gly Leu Asn Pro Leu Ile His Asn Ser Leu
1               5                   10                  15

Val Asp Arg Glu Val Asp Asp Arg Glu
            20                  25

<210> SEQ ID NO 27
<211> LENGTH: 20
<212> TYPE: PRT
<213> ORGANISM: Streptococcus mutans

<400> SEQUENCE: 27

Asp Gly Lys Leu Arg Tyr Tyr Asp Ala Asn Ser Gly Asp Gln Ala Phe
1               5                   10                  15

Asn Lys Ser Val
            20

<210> SEQ ID NO 28
<211> LENGTH: 14
<212> TYPE: PRT
<213> ORGANISM: Streptococcus mutans

<400> SEQUENCE: 28

Gln Trp Asn Gly Glu Ser Glu Lys Pro Tyr Asp Asp His Leu
1               5                   10

<210> SEQ ID NO 29
<211> LENGTH: 431
<212> TYPE: PRT
<213> ORGANISM: Streptococcus mutans

<400> SEQUENCE: 29

Met Lys Lys Arg Ile Leu Ser Ala Val Leu Val Ser Gly Val Thr Leu
1               5                   10                  15

Ser Ser Ala Thr Thr Leu Ser Ala Val Lys Ala Asp Asp Phe Asp Ala
            20                  25                  30

Gln Ile Ala Ser Gln Asp Ser Lys Ile Asn Asn Leu Thr Ala Gln Gln
        35                  40                  45

Gln Ala Ala Gln Ala Gln Val Asn Thr Ile Gln Gly Gln Val Ser Ala
    50                  55                  60

Leu Gln Thr Gln Gln Ala Glu Leu Gln Ala Glu Asn Gln Arg Leu Glu
65                  70                  75                  80
```

```
Ala Gln Ser Ala Thr Leu Gly Gln Gln Ile Gln Thr Leu Ser Ser Lys
                85                  90                  95

Ile Val Ala Arg Asn Glu Ser Leu Lys Gln Gln Ala Arg Ser Ala Gln
            100                 105                 110

Lys Ser Asn Ala Ala Thr Ser Tyr Ile Asn Ala Ile Ile Asn Ser Lys
            115                 120                 125

Ser Val Ser Asp Ala Ile Asn Arg Val Ser Ala Ile Arg Glu Val Val
    130                 135                 140

Ser Ala Asn Glu Lys Met Leu Gln Gln Glu Gln Asp Lys Ala Ala
145                 150                 155                 160

Val Glu Gln Lys Gln Gln Glu Asn Gln Ala Ala Ile Asn Thr Val Ala
                165                 170                 175

Ala Asn Gln Glu Thr Ile Ala Gln Asn Thr Asn Ala Leu Asn Thr Gln
            180                 185                 190

Gln Ala Gln Leu Glu Ala Ala Gln Leu Asn Leu Gln Ala Glu Leu Thr
        195                 200                 205

Thr Ala Gln Asp Gln Lys Ala Thr Leu Val Ala Gln Lys Ala Ala Ala
    210                 215                 220

Glu Glu Ala Ala Arg Gln Ala Ala Ala Gln Ala Ala Glu Ala
225                 230                 235                 240

Lys Ala Ala Ala Glu Ala Lys Ala Leu Gln Glu Gln Ala Ala Gln Ala
                245                 250                 255

Gln Val Ala Ala Asn Asn Asn Thr Gln Ala Thr Asp Ala Ser Asp Gln
            260                 265                 270

Gln Ala Ala Ala Asp Asn Thr Gln Ala Ala Gln Thr Gly Asp Ser
        275                 280                 285

Thr Glu Gln Ser Ala Ala Gln Ala Val Asn Asn Ser Asp Gln Glu Ser
    290                 295                 300

Thr Thr Ala Thr Glu Ala Gln Pro Ser Ala Ser Ser Ala Ser Thr Ala
305                 310                 315                 320

Ala Val Ala Ala Asn Thr Ser Ser Ala Asn Thr Tyr Pro Ala Gly Gln
                325                 330                 335

Cys Thr Trp Gly Val Lys Ser Leu Ala Pro Trp Val Gly Asn Tyr Trp
            340                 345                 350

Gly Asn Gly Gly Gln Trp Ala Ala Ser Ala Ala Ala Gly Tyr Arg
        355                 360                 365

Val Gly Ser Thr Pro Ser Ala Gly Ala Val Ala Val Trp Asn Asp Gly
    370                 375                 380

Gly Tyr Gly His Val Ala Tyr Val Thr Gly Val Gln Gly Gly Gln Ile
385                 390                 395                 400

Gln Val Gln Glu Ala Asn Tyr Ala Gly Asn Gln Ser Ile Gly Asn Tyr
                405                 410                 415

Arg Gly Trp Phe Asn Pro Gly Ser Val Ser Tyr Ile Tyr Pro Asn
            420                 425                 430

<210> SEQ ID NO 30
<211> LENGTH: 431
<212> TYPE: PRT
<213> ORGANISM: Streptococcus mutans

<400> SEQUENCE: 30

Met Lys Lys Arg Ile Leu Ser Ala Val Leu Ser Gly Val Thr Leu
1               5                   10                  15

Ser Ser Ala Thr Thr Leu Ser Ala Val Lys Ala Asp Asp Phe Asp Ala
```

-continued

```
                 20                  25                  30
Gln Ile Ala Ser Gln Asp Ser Lys Ile Asn Asn Leu Thr Ala Gln Gln
             35                  40                  45

Gln Ala Ala Gln Ala Gln Val Asn Thr Ile Gln Gly Gln Val Ser Ala
 50                  55                  60

Leu Gln Thr Gln Gln Ala Glu Leu Gln Ala Glu Asn Gln Arg Leu Glu
 65                  70                  75                  80

Ala Gln Ser Ala Thr Leu Gly Gln Gln Ile Gln Thr Leu Ser Ser Lys
                 85                  90                  95

Ile Val Ala Arg Asn Glu Ser Leu Lys Gln Gln Ala Arg Ser Ala Gln
             100                 105                 110

Lys Ser Asn Ala Ala Thr Ser Tyr Ile Asn Ala Ile Ile Asn Ser Lys
             115                 120                 125

Ser Val Ser Asp Ala Ile Asn Arg Val Ser Ala Ile Arg Glu Val Val
             130                 135                 140

Ser Ala Asn Glu Lys Met Leu Gln Gln Gln Glu Gln Asp Lys Ala Ala
145                 150                 155                 160

Val Glu Gln Lys Gln Gln Glu Asn Gln Ala Ala Ile Asn Thr Val Ala
             165                 170                 175

Ala Asn Gln Glu Thr Ile Ala Gln Asn Thr Asn Ala Leu Asn Thr Gln
             180                 185                 190

Gln Ala Gln Leu Glu Ala Ala Gln Leu Asn Leu Gln Ala Glu Leu Thr
             195                 200                 205

Thr Ala Gln Asp Gln Lys Ala Thr Leu Val Ala Gln Lys Ala Ala Ala
             210                 215                 220

Glu Glu Ala Ala Arg Gln Ala Ala Ala Gln Ala Ala Glu Ala
225                 230                 235                 240

Lys Ala Ala Glu Ala Lys Ala Leu Gln Glu Gln Ala Ala Gln Ala
             245                 250                 255

Gln Ala Ala Asn Asn Asn Thr Gln Ala Thr Asp Ala Ser Asp Gln
             260                 265                 270

Gln Ala Ala Ala Asp Asn Thr Gln Ala Ala Gln Thr Gly Asp Ser
             275                 280                 285

Thr Glu Gln Ser Ala Ala Gln Ala Val Asn Asn Ser Asp Gln Glu Ser
290                 295                 300

Thr Thr Ala Thr Glu Ala Gln Pro Ser Ala Ser Ser Ala Ser Thr Ala
305                 310                 315                 320

Ala Val Ala Ala Asn Thr Ser Ser Ala Asn Thr Tyr Pro Ala Gly Gln
             325                 330                 335

Cys Thr Trp Gly Val Lys Ser Leu Ala Pro Trp Val Gly Asn Tyr Trp
             340                 345                 350

Gly Asn Gly Gly Gln Trp Ala Ala Ser Ala Ala Ala Gly Tyr Arg
             355                 360                 365

Val Gly Ser Thr Pro Ser Ala Gly Val Ala Val Trp Asn Asp Gly
             370                 375                 380

Gly Tyr Gly His Val Ala Tyr Val Thr Gly Val Gln Gly Gly Gln Ile
385                 390                 395                 400

Gln Val Gln Glu Ala Asn Tyr Ala Gly Asn Gln Ser Ile Gly Asn Tyr
                 405                 410                 415

Arg Gly Trp Phe Asn Pro Gly Ser Val Ser Tyr Ile Tyr Pro Asn
             420                 425                 430

<210> SEQ ID NO 31
```

<211> LENGTH: 432
<212> TYPE: PRT
<213> ORGANISM: Streptococcus mutans

<400> SEQUENCE: 31

```
Met Lys Lys Arg Ile Leu Ser Ala Val Leu Val Ser Gly Val Thr Leu
1               5                   10                  15

Ser Ser Ala Thr Thr Leu Ser Ala Ile Lys Ala Asp Asp Phe Asp Ala
            20                  25                  30

Gln Ile Ala Ser Gln Asp Ser Lys Ile Asn Asn Leu Thr Ala Gln Gln
        35                  40                  45

Gln Ala Ala Gln Ala Gln Val Asn Thr Ile Gln Gly Gln Val Ser Ala
    50                  55                  60

Leu Gln Thr Gln Gln Ala Glu Leu Gln Ala Glu Asn Gln Arg Leu Glu
65                  70                  75                  80

Ala Gln Ser Ala Thr Leu Gly Gln Gln Ile Gln Thr Leu Ser Ser Lys
                85                  90                  95

Ile Val Ala Arg Asn Glu Ser Leu Lys Gln Ala Arg Ser Ala Gln
            100                 105                 110

Lys Ser Asn Ala Ala Thr Ser Tyr Ile Asn Ala Ile Ile Asn Ser Lys
        115                 120                 125

Ser Val Ser Asp Ala Ile Asn Arg Val Ser Ala Ile Arg Glu Val Val
    130                 135                 140

Ser Ala Asn Glu Lys Met Leu Gln Gln Gln Gln Asp Lys Ala Ala
145                 150                 155                 160

Val Glu Gln Lys Gln Gln Glu Asn Gln Ala Ala Ile Asn Thr Val Ala
                165                 170                 175

Ala Asn Gln Glu Thr Ile Ala Gln Asn Thr Asn Ala Leu Asn Thr Gln
            180                 185                 190

Gln Ala Gln Leu Glu Ala Ala Gln Leu Asn Leu Gln Ala Glu Leu Thr
        195                 200                 205

Thr Ala Gln Asp Gln Lys Ala Thr Leu Val Ala Gln Lys Ala Ala Ala
    210                 215                 220

Glu Glu Ala Ala Arg Gln Ala Ala Ala Gln Ala Ala Ala Glu Ala
225                 230                 235                 240

Lys Ala Ala Ala Glu Ala Lys Ala Leu Gln Glu Gln Ala Ala Gln Ala
                245                 250                 255

Gln Ala Ala Ala Asn Asn Asn Thr Gln Ala Thr Asp Ala Ser Asp
            260                 265                 270

Gln Gln Ala Ala Ala Ala Asp Asn Thr Gln Ala Ala Gln Thr Gly Asp
        275                 280                 285

Ser Thr Asp Gln Ser Ala Ala Gln Ala Val Asn Asn Ser Asp Gln Glu
    290                 295                 300

Ser Thr Thr Ala Thr Ala Ala Gln Pro Ser Ala Ser Ser Ala Ser Thr
305                 310                 315                 320

Ala Ala Val Ala Ala Asn Thr Ser Ser Ala Asn Thr Tyr Pro Ala Gly
                325                 330                 335

Gln Cys Thr Trp Gly Val Lys Ser Leu Ala Pro Trp Val Gly Asn Tyr
            340                 345                 350

Trp Gly Asn Gly Gly Gln Trp Ala Ser Ala Ala Ala Gly Tyr
        355                 360                 365

Arg Val Gly Ser Thr Pro Ser Ala Gly Ala Val Ala Val Trp Asn Asp
    370                 375                 380

Gly Gly Tyr Gly His Val Ala Tyr Val Thr Gly Val Gln Gly Gly Gln
```

```
                385                 390                 395                 400
Ile Gln Val Gln Glu Ala Asn Tyr Ala Gly Asn Gln Ser Ile Gly Asn
                    405                 410                 415

Tyr Arg Gly Trp Phe Asn Pro Gly Ser Val Ser Tyr Ile Tyr Pro Asn
                    420                 425                 430

<210> SEQ ID NO 32
<211> LENGTH: 432
<212> TYPE: PRT
<213> ORGANISM: Streptococcus mutans

<400> SEQUENCE: 32

Met Lys Lys Arg Ile Leu Ser Ala Val Leu Ser Gly Val Thr Leu
1               5                   10                  15

Ser Ser Ala Thr Thr Leu Ser Ala Val Lys Ala Asp Asp Phe Asp Ala
                20                  25                  30

Gln Ile Ala Ser Gln Asp Ser Lys Ile Asn Asn Leu Thr Ala Gln Gln
            35                  40                  45

Gln Ala Ala Gln Ala Gln Val Asn Thr Ile Gln Gly Gln Val Ser Ala
        50                  55                  60

Leu Gln Thr Gln Gln Ala Glu Leu Gln Ala Glu Asn Gln Arg Leu Glu
65                  70                  75                  80

Ala Gln Ser Ala Thr Leu Gly Gln Gln Ile Gln Thr Leu Ser Ser Lys
                85                  90                  95

Ile Val Ala Arg Asn Glu Ser Leu Lys Gln Gln Ala Arg Ser Ala Gln
            100                 105                 110

Lys Ser Asn Ala Ala Thr Ser Tyr Ile Asn Ala Ile Asn Ser Lys
        115                 120                 125

Ser Val Ser Asp Ala Ile Asn Arg Val Ser Ala Ile Arg Glu Val Val
        130                 135                 140

Ser Ala Asn Glu Lys Met Leu His Gln Gln Gln Asp Lys Ala Ala
145                 150                 155                 160

Val Glu Gln Lys His Gln Glu Asn Gln Ala Ala Ile Asn Thr Val Ala
                165                 170                 175

Ala Asn Gln Glu Thr Ile Ala Gln Asn Thr Asn Ala Leu Asn Thr Gln
            180                 185                 190

Gln Ala Gln Leu Glu Ala Ala Gln Leu Asn Leu Gln Ala Glu Leu Thr
        195                 200                 205

Thr Ala Gln Asp Gln Lys Ala Thr Leu Val Ala Gln Lys Ala Ala Ala
210                 215                 220

Glu Glu Ala Ala Arg Gln Ala Ala Ala Gln Ala Ala Glu Ala
225                 230                 235                 240

Lys Ala Ala Glu Ala Lys Ala Leu Gln Glu Gln Ala Ala Gln Ala
                245                 250                 255

Gln Ala Ala Asn Asn Asn Thr Gln Ala Thr Asp Ala Ser Asp
            260                 265                 270

Gln Gln Ala Ala Ala Asp Asn Thr Gln Ala Ala Gln Thr Gly Asp
        275                 280                 285

Ser Thr Asp Gln Ser Ala Ala Gln Ala Val Asn Asn Ser Asp Gln Glu
        290                 295                 300

Ser Thr Thr Ala Thr Ala Ala Gln Pro Ser Ala Ser Ser Ala Ser Thr
305                 310                 315                 320

Ala Ala Val Ala Ala Asn Thr Ser Ser Ala Asn Thr Tyr Pro Ala Gly
                325                 330                 335
```

```
Gln Cys Thr Trp Gly Val Lys Ser Leu Ala Pro Trp Val Gly Asn Tyr
                340                 345                 350

Trp Gly Asn Gly Gly Gln Trp Ala Ala Ser Ala Ala Ala Gly Tyr
        355                 360                 365

Arg Val Gly Ser Thr Pro Ser Ala Gly Ala Val Ala Val Trp Asn Asp
        370                 375                 380

Gly Gly Tyr Gly His Val Ala Tyr Val Thr Gly Val Gln Gly Gly Gln
385                 390                 395                 400

Ile Gln Val Gln Glu Ala Asn Tyr Ala Gly Asn Gln Ser Ile Gly Asn
                405                 410                 415

Tyr Arg Gly Trp Phe Asn Pro Gly Ser Val Ser Tyr Ile Tyr Pro Asn
                420                 425                 430

<210> SEQ ID NO 33
<211> LENGTH: 431
<212> TYPE: PRT
<213> ORGANISM: Streptococcus mutans

<400> SEQUENCE: 33

Met Lys Lys Arg Ile Leu Ser Ala Val Leu Ser Gly Val Thr Leu
1               5                   10                  15

Ser Ser Ala Thr Thr Leu Ser Ala Val Lys Ala Asp Asp Phe Asp Ala
                20                  25                  30

Gln Ile Ala Ser Gln Asp Ser Lys Ile Asn Asn Leu Thr Ala Gln Gln
        35                  40                  45

Gln Ala Ala Gln Ala Gln Val Asn Thr Ile Gln Gly Gln Val Ser Ala
    50                  55                  60

Leu Gln Thr Gln Gln Ala Glu Leu Gln Ala Glu Asn Gln Arg Leu Glu
65                  70                  75                  80

Ala Gln Ser Ala Thr Leu Gly Gln Gln Ile Gln Thr Leu Ser Ser Lys
                85                  90                  95

Ile Val Ala Arg Asn Glu Ser Leu Lys Gln Ala Arg Ser Ala Gln
                100                 105                 110

Lys Ser Asn Ala Ala Thr Ser Tyr Ile Asn Ala Ile Ile Asn Ser Lys
        115                 120                 125

Ser Val Ser Asp Ala Ile Asn Arg Val Ser Ala Ile Arg Glu Val Val
    130                 135                 140

Ser Ala Asn Glu Lys Met Leu Gln Gln Gln Glu Gln Asp Lys Ala Ala
145                 150                 155                 160

Val Glu Gln Lys Gln Gln Glu Asn Gln Ala Ala Ile Asn Thr Val Ala
                165                 170                 175

Ala Asn Gln Glu Thr Ile Ala Gln Asn Thr Asn Ala Leu Asn Thr Gln
        180                 185                 190

Gln Ala Gln Leu Glu Ala Ala Gln Leu Asn Leu Gln Ala Glu Leu Thr
    195                 200                 205

Thr Ala Gln Asp Gln Lys Ala Thr Leu Val Ala Gln Lys Ala Ala Ala
210                 215                 220

Glu Glu Ala Ala Arg Gln Ala Ala Ala Gln Ala Ala Glu Ala
225                 230                 235                 240

Lys Ala Ala Ala Glu Lys Ala Leu Gln Glu Gln Ala Ala Gln Ala
                245                 250                 255

Gln Ala Ala Ala Asn Asn Asn Thr Gln Ala Thr Asp Ala Ser Asp Gln
        260                 265                 270

Gln Ala Ala Ala Ala Asp Asn Thr Gln Ala Ala Gln Thr Gly Asp Ser
    275                 280                 285
```

```
Thr Glu Gln Ser Ala Ala Gln Ala Val Asn Asn Ser Asp Gln Glu Ser
    290                 295                 300

Thr Thr Ala Thr Glu Ala Gln Pro Ser Ala Ser Ser Ala Ser Thr Ala
305                 310                 315                 320

Val Val Thr Ala Asn Thr Ser Ser Ala Asn Thr Tyr Pro Ala Gly Gln
                325                 330                 335

Cys Thr Trp Gly Val Lys Ser Leu Ala Pro Trp Val Gly Asn Tyr Trp
            340                 345                 350

Gly Asn Gly Gly Gln Trp Ala Ala Ser Ala Ala Ala Gly Tyr Arg
        355                 360                 365

Val Gly Ser Thr Pro Ser Ala Gly Ala Val Ala Val Trp Asn Asp Gly
370                 375                 380

Gly Tyr Gly His Val Ala Tyr Val Thr Gly Val Gln Gly Gly Gln Ile
385                 390                 395                 400

Gln Val Gln Glu Ala Asn Tyr Ala Gly Asn Gln Ser Ile Gly Asn Tyr
                405                 410                 415

Arg Gly Trp Phe Asn Pro Gly Ser Val Ser Tyr Ile Tyr Pro Asn
            420                 425                 430

<210> SEQ ID NO 34
<211> LENGTH: 1475
<212> TYPE: PRT
<213> ORGANISM: Streptococcus mutans

<400> SEQUENCE: 34

Met Asp Lys Lys Val Arg Tyr Lys Leu Arg Lys Val Lys Lys Arg Trp
1               5                   10                  15

Val Thr Val Ser Val Ala Ser Ala Val Met Thr Leu Thr Thr Leu Ser
                20                  25                  30

Gly Gly Leu Val Lys Ala Asp Ser Asn Glu Ser Lys Ser Gln Ile Ser
            35                  40                  45

Asn Asp Ser Asn Thr Ser Val Val Thr Ala Asn Glu Glu Ser Asn Val
    50                  55                  60

Ile Thr Glu Ala Thr Ser Lys Gln Glu Ala Ser Ser Gln Thr Asn
65                  70                  75                  80

His Thr Val Thr Thr Ser Ser Ser Thr Ser Val Val Asn Pro Lys
                85                  90                  95

Glu Val Val Ser Asn Pro Tyr Thr Val Gly Glu Thr Ala Ser Asn Gly
                100                 105                 110

Glu Lys Leu Gln Asn Gln Thr Thr Val Asp Lys Thr Ser Glu Ala
            115                 120                 125

Ala Ala Asn Asn Ile Ser Lys Gln Thr Thr Glu Ala Asp Thr Asp Val
    130                 135                 140

Ile Asp Asp Ser Asn Ala Ala Asn Leu Gln Ile Leu Glu Lys Leu Pro
145                 150                 155                 160

Asn Val Lys Glu Ile Asp Gly Lys Tyr Tyr Tyr Asp Asn Asn Gly
                165                 170                 175

Lys Val Arg Thr Asn Phe Thr Leu Ile Ala Asp Gly Lys Ile Leu His
            180                 185                 190

Phe Asp Glu Thr Gly Ala Tyr Thr Asp Thr Ser Ile Asp Thr Val Asn
        195                 200                 205

Lys Asp Ile Val Thr Thr Arg Ser Asn Leu Tyr Lys Lys Tyr Asn Gln
    210                 215                 220

Val Tyr Asp Arg Ser Ala Gln Ser Phe Glu His Val Asp His Tyr Leu
```

-continued

```
            225                 230                 235                 240
Thr Ala Glu Ser Trp Tyr Arg Pro Lys Tyr Ile Leu Lys Asp Gly Lys
                245                 250                 255
Thr Trp Thr Gln Ser Thr Glu Lys Asp Phe Arg Pro Leu Leu Met Thr
                260                 265                 270
Trp Trp Pro Asp Gln Glu Thr Gln Arg Gln Tyr Val Asn Tyr Met Asn
            275                 280                 285
Ala Gln Leu Gly Ile Asn Lys Thr Tyr Asp Asp Thr Ser Asn Gln Leu
        290                 295                 300
Gln Leu Asn Ile Ala Ala Ala Thr Ile Gln Ala Lys Ile Glu Ala Lys
305                 310                 315                 320
Ile Thr Thr Leu Lys Asn Thr Asp Trp Leu Arg Gln Thr Ile Ser Ala
                325                 330                 335
Phe Val Lys Thr Gln Ser Ala Trp Asn Ser Asp Ser Glu Lys Pro Phe
                340                 345                 350
Asp Asp His Leu Gln Asn Gly Ala Val Leu Tyr Asp Asn Glu Gly Lys
            355                 360                 365
Leu Thr Pro Tyr Ala Asn Ser Asn Tyr Arg Ile Leu Asn Arg Thr Pro
        370                 375                 380
Thr Asn Gln Thr Gly Lys Lys Asp Pro Arg Tyr Thr Ala Asp Asn Thr
385                 390                 395                 400
Ile Gly Gly Tyr Glu Phe Leu Leu Ala Asn Asp Val Asp Asn Ser Asn
                405                 410                 415
Pro Val Val Gln Ala Glu Gln Leu Asn Trp Leu His Phe Leu Met Asn
            420                 425                 430
Phe Gly Asn Ile Tyr Ala Asn Asp Pro Asp Ala Asn Phe Asp Ser Ile
        435                 440                 445
Arg Val Asp Ala Val Asp Asn Val Asp Ala Asp Leu Leu Gln Ile Ala
        450                 455                 460
Gly Asp Tyr Leu Lys Ala Ala Lys Gly Ile His Lys Asn Asp Lys Ala
465                 470                 475                 480
Ala Asn Asp His Leu Ser Ile Leu Glu Ala Trp Ser Asp Asn Asp Thr
                485                 490                 495
Pro Tyr Leu His Asp Asp Gly Asp Asn Met Ile Asn Met Asp Asn Lys
            500                 505                 510
Leu Arg Leu Ser Leu Leu Phe Ser Leu Ala Lys Pro Leu Asn Gln Arg
        515                 520                 525
Ser Gly Met Asn Pro Leu Ile Thr Asn Ser Leu Val Asn Arg Thr Asp
        530                 535                 540
Asp Asn Ala Glu Thr Ala Ala Val Pro Ser Tyr Ser Phe Ile Arg Ala
545                 550                 555                 560
His Asp Ser Glu Val Gln Asp Leu Ile Ala Asp Ile Ile Lys Ala Glu
                565                 570                 575
Ile Asn Pro Asn Val Val Gly Tyr Ser Phe Thr Met Glu Glu Ile Lys
            580                 585                 590
Lys Ala Phe Glu Ile Tyr Asn Lys Asp Leu Leu Ala Thr Glu Lys Lys
        595                 600                 605
Tyr Thr His Tyr Asn Thr Ala Leu Ser Tyr Ala Leu Leu Leu Thr Asn
        610                 615                 620
Lys Ser Ser Val Pro Arg Val Tyr Tyr Gly Asp Met Phe Thr Asp Asp
625                 630                 635                 640
Gly Gln Tyr Met Ala His Lys Thr Ile Asn Tyr Glu Ala Ile Glu Thr
                645                 650                 655
```

-continued

Leu Leu Lys Ala Arg Ile Lys Tyr Val Ser Gly Gly Gln Ala Met Arg
            660                 665                 670

Asn Gln Gln Val Gly Asn Ser Glu Ile Ile Thr Ser Val Arg Tyr Gly
        675                 680                 685

Lys Gly Ala Leu Lys Ala Thr Asp Thr Gly Asp Arg Thr Thr Arg Thr
        690                 695                 700

Ser Gly Val Ala Val Ile Glu Gly Asn Pro Ser Leu Arg Leu Lys
705                 710                 715                 720

Ala Ser Asp Arg Val Val Asn Met Gly Ala His Lys Asn Gln
            725                 730                 735

Ala Tyr Arg Pro Leu Leu Thr Thr Asp Asn Gly Ile Lys Ala Tyr
            740                 745                 750

His Ser Asp Gln Glu Ala Ala Gly Leu Val Arg Tyr Thr Asn Asp Arg
        755                 760                 765

Gly Glu Leu Ile Phe Thr Ala Ala Asp Ile Lys Gly Tyr Ala Asn Pro
        770                 775                 780

Gln Val Ser Gly Tyr Leu Gly Val Trp Val Pro Val Gly Ala Ala Leu
785                 790                 795                 800

Ile Lys Met Phe Ala Leu Arg Leu Ala Arg Pro His Gln Met Ala
            805                 810                 815

Ser Val His Gln Asn Ala Ala Leu Asp Ser Arg Val Met Phe Glu Gly
            820                 825                 830

Phe Ser Asn Phe Gln Ala Phe Ala Thr Lys Lys Glu Glu Tyr Thr Asn
        835                 840                 845

Val Val Ile Ala Lys Asn Val Asp Lys Phe Ala Glu Trp Gly Val Thr
    850                 855                 860

Asp Phe Glu Met Ala Pro Gln Tyr Val Ser Ser Thr Asp Gly Ser Phe
865                 870                 875                 880

Leu Asp Ser Val Ile Gln Asn Gly Tyr Ala Phe Thr Asp Arg Tyr Asp
            885                 890                 895

Leu Gly Ile Ser Lys Pro Asn Lys Tyr Gly Thr Ala Asp Asp Leu Val
            900                 905                 910

Lys Ala Ile Lys Ala Leu His Ser Lys Gly Ile Lys Val Met Ala Asp
        915                 920                 925

Trp Val Pro Asp Gln Met Tyr Ala Phe Pro Glu Lys Val Val Thr
930                 935                 940

Ala Thr Arg Val Asp Lys Tyr Gly Thr Pro Val Ala Gly Ser Gln Ile
945                 950                 955                 960

Lys Asn Thr Leu Tyr Val Val Asp Gly Lys Ser Ser Gly Lys Asp Gln
            965                 970                 975

Gln Ala Lys Tyr Gly Gly Ala Phe Leu Glu Glu Leu Gln Ala Lys Tyr
            980                 985                 990

Pro Glu Leu Phe Ala Arg Lys Gln Ile Ser Thr Gly Val Pro Met Asp
        995                 1000                1005

Pro Ser Val Lys Ile Lys Gln Trp Ser Ala Lys Tyr Phe Asn Gly
    1010                1015                1020

Thr Asn Ile Leu Gly Arg Gly Ala Gly Tyr Val Leu Lys Asp Gln
    1025                1030                1035

Ala Thr Asn Thr Tyr Phe Asn Ile Ser Asp Asn Lys Glu Ile Asn
    1040                1045                1050

Phe Leu Pro Lys Thr Leu Leu Asn Gln Asp Ser Gln Val Gly Phe
    1055                1060                1065

-continued

```
Ser Tyr Asp Gly Lys Gly Tyr Val Tyr Tyr Ser Thr Ser Gly Tyr
    1070            1075                1080

Gln Ala Lys Asn Thr Phe Ile Ser Glu Gly Asp Lys Trp Tyr Tyr
    1085            1090                1095

Phe Asp Asn Asn Gly Tyr Met Val Thr Gly Ala Gln Ser Ile Asn
    1100            1105                1110

Gly Val Asn Tyr Tyr Phe Leu Ser Asn Gly Leu Gln Leu Arg Asp
    1115            1120                1125

Ala Ile Leu Lys Asn Glu Asp Gly Thr Tyr Ala Tyr Tyr Gly Asn
    1130            1135                1140

Asp Gly Arg Arg Tyr Glu Asn Gly Tyr Tyr Gln Phe Met Ser Gly
    1145            1150                1155

Val Trp Arg His Phe Asn Asn Gly Glu Met Ser Val Gly Leu Thr
    1160            1165                1170

Val Ile Asp Gly Gln Val Gln Tyr Phe Asp Glu Met Gly Tyr Gln
    1175            1180                1185

Ala Lys Gly Lys Phe Val Thr Thr Ala Asp Gly Lys Ile Arg Tyr
    1190            1195                1200

Phe Asp Lys Gln Ser Gly Asn Met Tyr Arg Asn Arg Phe Ile Glu
    1205            1210                1215

Asn Glu Glu Gly Lys Trp Leu Tyr Leu Gly Glu Asp Gly Ala Ala
    1220            1225                1230

Val Thr Gly Ser Gln Thr Ile Asn Gly Gln His Leu Tyr Phe Arg
    1235            1240                1245

Ala Asn Gly Val Gln Val Lys Gly Glu Phe Val Thr Asp His His
    1250            1255                1260

Gly Arg Ile Ser Tyr Tyr Asp Gly Asn Ser Gly Asp Gln Ile Arg
    1265            1270                1275

Asn Arg Phe Val Arg Asn Ala Gln Gly Gln Trp Phe Tyr Phe Asp
    1280            1285                1290

Asn Asn Gly Tyr Ala Val Thr Gly Ala Arg Thr Ile Asn Gly Gln
    1295            1300                1305

Leu Leu Tyr Phe Arg Ala Asn Gly Val Gln Val Lys Gly Glu Phe
    1310            1315                1320

Val Thr Asp Arg Tyr Gly Arg Ile Ser Tyr Tyr Asp Gly Asn Ser
    1325            1330                1335

Gly Asp Gln Ile Arg Asn Arg Phe Val Arg Asn Ala Gln Gly Gln
    1340            1345                1350

Trp Phe Tyr Phe Asp Asn Asn Gly Tyr Ala Val Thr Gly Ala Arg
    1355            1360                1365

Thr Ile Asn Gly Gln His Leu Tyr Phe Arg Ala Asn Gly Val Gln
    1370            1375                1380

Val Lys Gly Glu Phe Val Thr Asp Arg His Gly Arg Ile Ser Tyr
    1385            1390                1395

Tyr Asp Gly Asn Ser Gly Asp Gln Ile Arg Asn Arg Phe Val Arg
    1400            1405                1410

Asn Ala Gln Gly Gln Trp Phe Tyr Phe Asp Asn Asn Gly Tyr Ala
    1415            1420                1425

Val Thr Gly Ala Arg Thr Ile Asn Gly Gln His Leu Tyr Phe Arg
    1430            1435                1440

Ala Asn Gly Val Gln Val Lys Gly Glu Phe Val Thr Asp Arg Tyr
    1445            1450                1455

Gly Arg Ile Ser Tyr Tyr Asp Ala Asn Ser Gly Glu Arg Val Arg
```

-continued

```
                1460                1465                1470
Ile Asn
    1475

<210> SEQ ID NO 35
<211> LENGTH: 1375
<212> TYPE: PRT
<213> ORGANISM: Streptococcus mutans

<400> SEQUENCE: 35

Met Glu Lys Lys Val Arg Phe Lys Leu Arg Lys Val Lys Lys Arg Trp
1               5                   10                  15

Val Thr Val Ser Ile Ala Ser Ala Val Thr Leu Thr Ser Leu Ser
            20                  25                  30

Gly Ser Leu Val Lys Ala Asp Ser Thr Asp Arg Gln Gln Ala Val
        35                  40                  45

Thr Glu Ser Gln Ala Ser Leu Val Thr Ser Glu Ala Ala Lys Glu
    50                  55                  60

Thr Leu Thr Ala Thr Asp Thr Ser Thr Ala Ser Ala Thr Ser Gln
65                  70                  75                  80

Pro Thr Ala Thr Val Thr Asp Asn Val Ser Thr Thr Asn Gln Ser Thr
                85                  90                  95

Asn Thr Thr Ala Asn Thr Ala Asn Phe Val Val Lys Pro Thr Thr Thr
            100                 105                 110

Ser Glu Gln Ala Lys Thr Asp Asn Ser Asp Lys Ile Ile Thr Thr Ser
        115                 120                 125

Lys Ala Val Asn Arg Leu Thr Ala Thr Gly Lys Phe Val Pro Ala Asn
    130                 135                 140

Asn Asn Thr Ala His Pro Lys Thr Val Thr Asp Lys Ile Val Pro Ile
145                 150                 155                 160

Lys Pro Lys Ile Gly Lys Leu Lys Gln Pro Ser Ser Leu Ser Gln Asp
                165                 170                 175

Asp Ile Ala Ala Leu Gly Asn Val Lys Asn Ile Arg Lys Val Asn Gly
            180                 185                 190

Lys Tyr Tyr Tyr Tyr Lys Glu Asp Gly Thr Leu Gln Lys Asn Tyr Ala
        195                 200                 205

Leu Asn Ile Asn Gly Lys Thr Phe Phe Asp Glu Thr Gly Ala Leu
    210                 215                 220

Ser Asn Asn Thr Leu Pro Ser Lys Lys Gly Asn Ile Thr Asn Asn Asp
225                 230                 235                 240

Asn Thr Asn Ser Phe Ala Gln Tyr Asn Gln Val Tyr Ser Thr Asp Val
                245                 250                 255

Ala Asn Phe Glu His Val Asp His Tyr Leu Thr Ala Glu Ser Trp Tyr
            260                 265                 270

Arg Pro Lys Tyr Ile Leu Lys Asp Gly Lys Thr Trp Thr Gln Ser Thr
        275                 280                 285

Glu Lys Asp Phe Arg Pro Leu Leu Met Thr Trp Trp Pro Asp Gln Glu
    290                 295                 300

Thr Gln Arg Gln Tyr Val Asn Tyr Met Asn Ala Gln Leu Gly Ile His
305                 310                 315                 320

Gln Thr Tyr Asn Thr Ala Thr Ser Pro Leu Gln Leu Asn Leu Ala Ala
                325                 330                 335

Gln Thr Ile Gln Thr Lys Ile Glu Glu Lys Ile Thr Ala Glu Lys Asn
            340                 345                 350
```

```
Thr Asn Trp Leu Arg Gln Thr Ile Ser Ala Phe Val Lys Thr Gln Ser
            355                 360                 365

Ala Trp Asn Ser Asp Ser Glu Lys Pro Phe Asp Asp His Leu Gln Lys
    370                 375                 380

Gly Ala Leu Leu Tyr Ser Asn Asn Ser Lys Leu Thr Ser Gln Ala Asn
385                 390                 395                 400

Ser Asn Tyr Arg Ile Leu Asn Arg Thr Pro Thr Asn Gln Thr Gly Lys
                405                 410                 415

Lys Asp Pro Arg Tyr Thr Ala Asp Arg Thr Ile Gly Gly Tyr Glu Phe
                420                 425                 430

Leu Leu Ala Asn Asp Val Asp Asn Ser Asn Pro Val Gln Ala Glu
            435                 440                 445

Gln Leu Asn Trp Leu His Phe Leu Met Asn Phe Gly Asn Ile Tyr Ala
    450                 455                 460

Asn Asp Pro Asp Ala Asn Phe Asp Ser Ile Arg Val Asp Ala Val Asp
465                 470                 475                 480

Asn Val Asp Ala Asp Leu Leu Gln Ile Ala Gly Asp Tyr Leu Lys Ala
                485                 490                 495

Ala Lys Gly Ile His Lys Asn Asp Lys Ala Ala Asn Asp His Leu Ser
            500                 505                 510

Ile Leu Glu Ala Trp Ser Tyr Asn Asp Thr Pro Tyr Leu His Asp Asp
    515                 520                 525

Gly Asp Asn Met Ile Asn Met Asp Asn Arg Leu Arg Leu Ser Leu Leu
530                 535                 540

Tyr Ser Leu Ala Lys Pro Leu Asn Gln Arg Ser Gly Met Asn Pro Leu
545                 550                 555                 560

Ile Thr Asn Ser Leu Val Asn Arg Thr Asp Asp Asn Ala Glu Thr Ala
                565                 570                 575

Ala Val Pro Ser Tyr Ser Phe Ile Arg Ala His Asp Ser Glu Val Gln
            580                 585                 590

Asp Leu Ile Arg Asn Ile Ile Arg Thr Glu Ile Asn Pro Asn Val Val
    595                 600                 605

Gly Tyr Ser Phe Thr Thr Glu Glu Ile Lys Lys Ala Phe Glu Ile Tyr
610                 615                 620

Asn Lys Asp Leu Leu Ala Thr Glu Lys Lys Tyr Thr His Tyr Asn Thr
625                 630                 635                 640

Ala Leu Ser Tyr Ala Leu Leu Leu Thr Asn Lys Ser Ser Val Pro Arg
                645                 650                 655

Val Tyr Tyr Gly Asp Met Phe Thr Asp Asp Gly Gln Tyr Met Ala His
            660                 665                 670

Lys Thr Ile Asn Tyr Glu Ala Ile Glu Thr Leu Leu Lys Ala Arg Ile
    675                 680                 685

Lys Tyr Val Ser Gly Gly Gln Ala Met Arg Asn Gln Gln Val Gly Asn
    690                 695                 700

Ser Glu Ile Ile Thr Ser Val Arg Tyr Gly Lys Gly Ala Leu Lys Ala
705                 710                 715                 720

Thr Asp Thr Gly Asp Arg Thr Thr Arg Thr Ser Gly Val Ala Val Ile
                725                 730                 735

Glu Gly Asn Asn Pro Ser Leu Arg Leu Lys Ala Ser Asp Arg Val Val
            740                 745                 750

Val Asn Met Gly Ala Ala His Lys Asn Gln Ala Tyr Arg Pro Leu Leu
    755                 760                 765

Leu Thr Thr Asp Asn Gly Ile Lys Ala Tyr His Ser Asp Gln Glu Ala
```

-continued

```
            770             775             780
Ala Gly Leu Val Arg Tyr Thr Asn Asp Arg Gly Glu Leu Ile Phe Thr
785             790                     795                 800

Ala Ala Asp Ile Lys Gly Tyr Ala Asn Pro Gln Val Ser Gly Tyr Leu
            805             810                     815

Gly Val Trp Val Pro Val Gly Ala Ala Asp Gln Asp Val Arg Val
            820             825                 830

Ala Ala Ser Thr Ala Pro Ser Thr Asp Gly Lys Ser Val His Gln Asn
            835             840                 845

Ala Ala Leu Asp Ser Arg Val Met Phe Glu Gly Phe Ser Asn Phe Gln
850             855                     860

Ala Phe Ala Thr Lys Lys Glu Glu Tyr Thr Asn Val Val Ile Ala Lys
865             870                     875                 880

Asn Val Asp Lys Phe Ala Glu Trp Gly Val Thr Asp Phe Glu Met Ala
            885                     890                 895

Pro Gln Tyr Val Ser Ser Thr Asp Gly Ser Phe Leu Asp Ser Val Ile
            900             905                     910

Gln Asn Gly Tyr Ala Phe Thr Asp Arg Tyr Asp Leu Gly Ile Ser Lys
            915             920                     925

Pro Asn Lys Tyr Gly Thr Ala Asp Asp Leu Val Lys Ala Ile Lys Ala
930             935                     940

Leu His Ser Lys Gly Ile Lys Val Met Ala Asp Trp Val Pro Asp Gln
945             950                     955                 960

Met Tyr Ala Leu Pro Glu Lys Glu Val Val Thr Ala Thr Arg Val Asp
            965                     970                 975

Lys Tyr Gly Thr Pro Val Ala Gly Ser Gln Ile Lys Asn Thr Leu Tyr
            980                     985                 990

Val Val Asp Gly Lys Ser Ser Gly  Lys Asp Gln Gln Ala  Lys Tyr Gly
            995             1000                    1005

Gly Ala  Phe Leu Glu Glu Leu  Gln Ala Lys Tyr Pro  Glu Leu Phe
1010                    1015                    1020

Ala Arg Lys Gln Ile Ser Thr  Gly Val Pro Met Asp  Pro Ser Val
1025                    1030                    1035

Lys Ile Lys Gln Trp Ser Ala  Lys Tyr Phe Asn Gly  Thr Asn Ile
1040                    1045                    1050

Leu Gly  Arg Gly Ala Gly Tyr  Val Leu Lys Asp Gln  Ala Thr Asn
1055                    1060                    1065

Thr Tyr  Phe Ser Leu Val Ser  Asp Asn Thr Phe Leu  Pro Lys Ser
1070                    1075                    1080

Leu Val  Asn Pro Asn His Gly  Thr Ser Ser Ser Val  Thr Gly Leu
1085                    1090                    1095

Val Phe  Asp Gly Lys Gly Tyr  Val Tyr Tyr Ser Thr  Ser Gly Asn
1100                    1105                    1110

Gln Ala  Lys Asn Ala Phe Ile  Ser Leu Gly Asn Asn  Trp Tyr Tyr
1115                    1120                    1125

Phe Asp  Asn Asn Gly Tyr Met  Val Thr Gly Ala Gln  Ser Ile Asn
1130                    1135                    1140

Gly Ala  Asn Tyr Tyr Phe Leu  Ser Asn Gly Ile Gln  Leu Arg Asn
1145                    1150                    1155

Ala Ile  Tyr Asp Asn Gly Asn  Lys Val Leu Ser Tyr  Tyr Gly Asn
1160                    1165                    1170

Asp Gly  Arg Arg Tyr Glu Asn  Gly Tyr Tyr Leu Phe  Gly Gln Gln
1175                    1180                    1185
```

-continued

Trp Arg Tyr Phe Gln Asn Gly Ile Met Ala Val Gly Leu Thr Arg
    1190                1195                1200

Val His Gly Ala Val Gln Tyr Phe Asp Ala Ser Gly Phe Gln Ala
    1205                1210                1215

Lys Gly Gln Phe Ile Thr Thr Ala Asp Gly Lys Leu Arg Tyr Phe
    1220                1225                1230

Asp Arg Asp Ser Gly Asn Gln Ile Ser Asn Arg Phe Val Arg Asn
    1235                1240                1245

Ser Lys Gly Glu Trp Phe Leu Phe Asp His Asn Gly Val Ala Val
    1250                1255                1260

Thr Gly Thr Val Thr Phe Asn Gly Gln Arg Leu Tyr Phe Lys Pro
    1265                1270                1275

Asn Gly Val Gln Ala Lys Gly Glu Phe Ile Arg Asp Ala Asn Gly
    1280                1285                1290

Tyr Leu Arg Tyr Tyr Asp Pro Asn Ser Gly Asn Glu Val Arg Asn
    1295                1300                1305

Arg Phe Val Arg Asn Ser Lys Gly Glu Trp Phe Leu Phe Asp His
    1310                1315                1320

Asn Gly Ile Ala Val Thr Gly Ala Arg Val Val Asn Gly His Ala
    1325                1330                1335

Ser Ile Leu Ser Leu Met Val Phe Arg Leu Arg Glu Ser Ser Leu
    1340                1345                1350

Gln Ser Val Lys Val Val Ser Asn Thr Met Ile Leu Ile Pro Glu
    1355                1360                1365

Met Lys Phe Val Ile Val Met
    1370                1375

<210> SEQ ID NO 36
<211> LENGTH: 1430
<212> TYPE: PRT
<213> ORGANISM: Streptococcus mutans

<400> SEQUENCE: 36

Met Glu Thr Lys Arg Arg Tyr Lys Met His Lys Val Lys Lys His Trp
1               5                   10                  15

Val Thr Val Ala Val Ala Ser Gly Leu Ile Thr Leu Gly Thr Thr Thr
                20                  25                  30

Leu Gly Ser Ser Val Ser Ala Glu Thr Glu Gln Gln Thr Ser Asp Lys
            35                  40                  45

Val Val Thr Gln Lys Ser Glu Asp Lys Ala Ala Ser Glu Ser Ser
        50                  55                  60

Gln Thr Asp Ala Pro Lys Thr Lys Gln Ala Gln Thr Glu Gln Thr Gln
65                  70                  75                  80

Ala Gln Ser Gln Ala Asn Val Ala Asp Thr Ser Thr Ile Thr Lys
                85                  90                  95

Glu Thr Pro Ser Gln Asn Ile Thr Thr Gln Ala Asn Ser Asp Asp Lys
            100                 105                 110

Thr Val Thr Asn Thr Lys Ser Glu Glu Ala Gln Thr Ser Glu Glu Arg
        115                 120                 125

Thr Lys Gln Ser Glu Glu Ala Gln Thr Thr Ala Ser Ser Gln Ala Leu
    130                 135                 140

Thr Gln Ala Lys Ala Glu Leu Thr Lys Gln Arg Gln Thr Ala Ala Gln
145                 150                 155                 160

Glu Asn Lys Asn Pro Val Asp Leu Ala Ala Ile Pro Asn Val Lys Gln

-continued

```
                165                 170                 175
Ile Asp Gly Lys Tyr Tyr Ile Gly Ser Asp Gly Gln Pro Lys Lys
            180                 185                 190
Asn Phe Ala Leu Thr Val Asn Asn Lys Val Leu Tyr Phe Asp Lys Asn
            195                 200                 205
Thr Gly Ala Leu Thr Asp Thr Ser Gln Tyr Gln Phe Lys Gln Gly Leu
        210                 215                 220
Thr Lys Leu Asn Asn Asp Tyr Thr Pro His Asn Gln Ile Val Asn Phe
225                 230                 235                 240
Glu Asn Thr Ser Leu Glu Thr Ile Asp Asn Tyr Val Thr Ala Asp Ser
                245                 250                 255
Trp Tyr Arg Pro Lys Asp Ile Leu Lys Asn Gly Lys Thr Trp Thr Ala
                260                 265                 270
Ser Ser Glu Ser Asp Leu Arg Pro Leu Leu Met Ser Trp Trp Pro Asp
            275                 280                 285
Lys Gln Thr Gln Ile Ala Tyr Leu Asn Tyr Met Asn Gln Gln Gly Leu
        290                 295                 300
Gly Thr Gly Glu Asn Tyr Thr Ala Asp Ser Ser Gln Glu Ser Leu Asn
305                 310                 315                 320
Leu Ala Ala Gln Thr Val Gln Val Lys Ile Glu Thr Lys Ile Ser Gln
                325                 330                 335
Thr Gln Gln Thr Gln Trp Leu Arg Asp Ile Ile Asn Ser Phe Val Lys
            340                 345                 350
Thr Gln Pro Asn Trp Asn Ser Gln Thr Glu Ser Asp Thr Ser Ala Gly
        355                 360                 365
Glu Lys Asp His Leu Gln Gly Gly Ala Leu Leu Tyr Ser Asn Ser Asp
370                 375                 380
Lys Thr Ala Tyr Ala Asn Ser Asp Tyr Arg Leu Leu Asn Arg Thr Pro
385                 390                 395                 400
Thr Ser Gln Thr Gly Lys Pro Lys Tyr Phe Glu Asp Asn Ser Ser Gly
                405                 410                 415
Gly Tyr Asp Phe Leu Leu Ala Asn Asp Ile Asp Asn Ser Asn Pro Val
            420                 425                 430
Val Gln Ala Glu Gln Leu Asn Trp Leu His Tyr Leu Met Asn Tyr Gly
        435                 440                 445
Ser Ile Val Ala Asn Asp Pro Glu Ala Asn Phe Asp Gly Val Arg Val
450                 455                 460
Asp Ala Val Asp Asn Val Asn Ala Asp Leu Leu Gln Ile Ala Ser Asp
465                 470                 475                 480
Tyr Leu Lys Ala His Tyr Gly Val Asp Lys Ser Glu Lys Asn Ala Ile
                485                 490                 495
Asn His Leu Ser Ile Leu Glu Ala Trp Ser Asp Asn Asp Pro Gln Tyr
            500                 505                 510
Asn Lys Asp Thr Lys Gly Ala Gln Leu Pro Ile Asp Asn Lys Leu Arg
        515                 520                 525
Leu Ser Leu Leu Tyr Ala Leu Thr Arg Pro Leu Glu Lys Asp Ala Ser
    530                 535                 540
Asn Lys Asn Glu Ile Arg Ser Gly Leu Glu Pro Val Ile Thr Asn Ser
545                 550                 555                 560
Leu Asn Asn Arg Ser Ala Glu Gly Lys Asn Ser Glu Arg Met Ala Asn
                565                 570                 575
Tyr Ile Phe Ile Arg Ala His Asp Ser Glu Val Gln Thr Val Ile Ala
            580                 585                 590
```

-continued

```
Lys Ile Ile Lys Ala Gln Ile Asn Pro Lys Thr Asp Gly Leu Thr Phe
            595                 600                 605
Thr Leu Asp Glu Leu Lys Gln Ala Phe Lys Ile Tyr Asn Glu Asp Met
            610                 615                 620
Arg Gln Ala Lys Lys Lys Tyr Thr Gln Ser Asn Ile Pro Thr Ala Tyr
625                 630                 635                 640
Ala Leu Met Leu Ser Asn Lys Asp Ser Ile Thr Arg Leu Tyr Tyr Gly
            645                 650                 655
Asp Met Tyr Ser Asp Asp Gly Gln Tyr Met Ala Thr Lys Ser Pro Tyr
            660                 665                 670
Tyr Asp Ala Ile Asp Thr Leu Leu Lys Ala Arg Ile Lys Tyr Ala Ala
            675                 680                 685
Gly Gly Gln Asp Met Lys Ile Thr Tyr Val Glu Gly Asp Lys Ser His
            690                 695                 700
Met Asp Trp Asp Tyr Thr Gly Val Leu Thr Ser Val Arg Tyr Gly Thr
705                 710                 715                 720
Gly Ala Asn Glu Ala Thr Asp Gln Gly Ser Glu Ala Thr Lys Thr Gln
            725                 730                 735
Gly Met Ala Val Ile Thr Ser Asn Asn Pro Ser Leu Lys Leu Asn Gln
            740                 745                 750
Asn Asp Lys Val Ile Val Asn Met Gly Ala Ala His Lys Asn Gln Glu
            755                 760                 765
Tyr Arg Pro Leu Leu Leu Thr Thr Lys Asp Gly Leu Thr Ser Tyr Thr
            770                 775                 780
Ser Asp Ala Ala Ala Lys Ser Leu Tyr Arg Lys Thr Asn Asp Lys Gly
785                 790                 795                 800
Glu Leu Val Phe Asp Ala Ser Asp Ile Gln Gly Tyr Leu Asn Pro Gln
            805                 810                 815
Val Ser Gly Tyr Leu Ala Val Trp Val Pro Val Gly Ala Ser Asp Asn
            820                 825                 830
Gln Asp Val Arg Val Ala Ala Ser Asn Lys Ala Asn Ala Thr Gly Gln
            835                 840                 845
Val Tyr Glu Ser Ser Ser Ala Leu Asp Ser Gln Leu Ile Tyr Glu Gly
            850                 855                 860
Phe Ser Asn Phe Gln Asp Phe Val Thr Lys Asp Ser Asp Tyr Thr Asn
865                 870                 875                 880
Lys Lys Ile Ala Gln Asn Val Gln Leu Phe Lys Ser Trp Gly Val Thr
            885                 890                 895
Ser Phe Glu Met Ala Pro Gln Tyr Val Ser Ser Glu Asp Gly Ser Phe
            900                 905                 910
Leu Asp Ser Ile Ile Gln Asn Gly Tyr Ala Phe Glu Asp Arg Tyr Asp
            915                 920                 925
Leu Ala Met Ser Lys Asn Asn Lys Tyr Gly Ser Gln Gln Asp Met Ile
            930                 935                 940
Asn Ala Val Lys Ala Leu His Lys Ser Gly Ile Gln Val Ile Ala Asp
945                 950                 955                 960
Trp Val Pro Asp Gln Ile Tyr Asn Leu Pro Gly Lys Glu Val Val Thr
            965                 970                 975
Ala Thr Arg Val Asn Asp Tyr Gly Glu Tyr Arg Lys Asp Ser Glu Ile
            980                 985                 990
Lys Asn Thr Leu Tyr Ala Ala Asn  Thr Lys Ser Asn Gly  Lys Asp Tyr
            995                 1000                1005
```

```
Gln Ala Lys Tyr Gly Gly Ala Phe Leu Ser Glu Leu Ala Ala Lys
    1010                1015                1020
Tyr Pro Ser Ile Phe Asn Arg Thr Gln Ile Ser Asn Gly Lys Lys
    1025                1030                1035
Ile Asp Pro Ser Glu Lys Ile Thr Ala Trp Lys Ala Lys Tyr Phe
    1040                1045                1050
Asn Gly Thr Asn Ile Leu Gly Arg Gly Val Gly Tyr Val Leu Lys
    1055                1060                1065
Asp Asn Ala Ser Asp Lys Tyr Phe Glu Leu Lys Gly Asn Gln Thr
    1070                1075                1080
Tyr Leu Pro Lys Gln Met Thr Asn Lys Glu Ala Ser Thr Gly Phe
    1085                1090                1095
Val Asn Asp Gly Asn Gly Met Thr Phe Tyr Ser Thr Ser Gly Tyr
    1100                1105                1110
Gln Ala Lys Asn Ser Phe Val Gln Asp Ala Lys Gly Asn Trp Tyr
    1115                1120                1125
Tyr Phe Asp Asn Asn Gly His Met Val Tyr Gly Leu Gln Gln Leu
    1130                1135                1140
Asn Gly Glu Val Gln Tyr Phe Leu Ser Asn Gly Val Gln Leu Arg
    1145                1150                1155
Glu Ser Phe Leu Glu Asn Ala Asp Gly Ser Lys Asn Tyr Phe Gly
    1160                1165                1170
His Leu Gly Asn Arg Tyr Ser Asn Gly Tyr Tyr Ser Phe Asp Asn
    1175                1180                1185
Asp Ser Lys Trp Arg Tyr Phe Asp Ala Ser Gly Val Met Ala Val
    1190                1195                1200
Gly Leu Lys Thr Ile Asn Gly Asn Thr Gln Tyr Phe Asp Gln Asp
    1205                1210                1215
Gly Tyr Gln Val Lys Gly Ala Trp Ile Thr Gly Ser Asp Gly Lys
    1220                1225                1230
Lys Arg Tyr Phe Asp Asp Gly Ser Gly Asn Met Ala Val Asn Arg
    1235                1240                1245
Phe Ala Asn Asp Lys Asn Gly Asp Trp Tyr Tyr Leu Asn Ser Asp
    1250                1255                1260
Gly Ile Ala Leu Val Gly Val Gln Thr Ile Asn Gly Lys Thr Tyr
    1265                1270                1275
Tyr Phe Gly Gln Asp Gly Lys Gln Ile Lys Gly Lys Ile Ile Thr
    1280                1285                1290
Asp Asn Gly Lys Leu Lys Tyr Phe Leu Ala Asn Ser Gly Glu Leu
    1295                1300                1305
Ala Arg Asn Ile Phe Ala Thr Asp Ser Gln Asn Asn Trp Tyr Tyr
    1310                1315                1320
Phe Gly Ser Asp Gly Val Ala Val Thr Gly Ser Gln Thr Ile Ala
    1325                1330                1335
Gly Lys Lys Leu Tyr Phe Ala Ser Asp Gly Lys Gln Val Lys Gly
    1340                1345                1350
Ser Phe Val Thr Tyr Asn Gly Lys Val His Tyr Tyr His Ala Asp
    1355                1360                1365
Ser Gly Glu Leu Gln Val Asn Arg Phe Glu Ala Asp Lys Asp Gly
    1370                1375                1380
Asn Trp Tyr Tyr Leu Asp Ser Asn Gly Glu Ala Leu Thr Gly Ser
    1385                1390                1395
Gln Arg Ile Asn Asp Gln Arg Val Phe Phe Thr Arg Glu Gly Lys
```

-continued

```
                1400                1405                1410
       Gln Val Lys Gly Asp Val Ala Tyr Asp Glu Arg Arg Leu Leu Val
           1415                1420                1425

Tyr Arg
           1430
```

<210> SEQ ID NO 37
<211> LENGTH: 1590
<212> TYPE: PRT
<213> ORGANISM: Streptococcus sobrinus

<400> SEQUENCE: 37

```
Met Glu Lys Asn Val Arg Phe Lys Met His Lys Val Lys Lys Arg Trp
 1               5                  10                  15

Val Thr Leu Ser Val Ala Ser Ala Thr Met Leu Ala Ser Ala Leu Gly
                20                  25                  30

Ala Ser Val Ala Ser Ala Asp Thr Asp Thr Ala Ser Asp Asp Ser Asn
            35                  40                  45

Gln Ala Val Val Thr Gly Asp Gln Thr Thr Asn Asn Gln Ala Thr Asp
        50                  55                  60

Gln Thr Ser Ile Ala Ala Thr Ala Thr Ser Glu Gln Ser Ala Ser Thr
65                  70                  75                  80

Asp Ala Ala Thr Asp Gln Ala Ser Ala Ala Glu Gln Thr Gln Gly Thr
                85                  90                  95

Thr Ala Ser Thr Asp Thr Ala Ala Gln Thr Thr Thr Asn Ala Asn Glu
                100                 105                 110

Ala Lys Trp Val Pro Thr Glu Asn Glu Asn Gln Gly Phe Thr Asp Glu
            115                 120                 125

Met Leu Ala Glu Ala Lys Asn Val Ala Thr Ala Glu Ser Asp Ser Ile
        130                 135                 140

Pro Ser Asp Leu Ala Lys Met Ser Asn Val Lys Gln Val Asp Gly Lys
145                 150                 155                 160

Tyr Tyr Tyr Tyr Asp Gln Asp Gly Asn Val Lys Lys Asn Phe Ala Val
                165                 170                 175

Ser Val Gly Asp Lys Ile Tyr Tyr Phe Asp Glu Thr Gly Ala Tyr Lys
                180                 185                 190

Asp Thr Ser Lys Val Asp Ala Asp Lys Ser Ser Ser Ala Val Ser Gln
            195                 200                 205

Asn Ala Thr Ile Phe Ala Ala Asn Asn Arg Ala Tyr Ser Thr Ser Ala
        210                 215                 220

Lys Asn Phe Glu Ala Val Asp Asn Tyr Leu Thr Ala Asp Ser Trp Tyr
225                 230                 235                 240

Arg Pro Lys Ser Ile Leu Lys Asp Gly Lys Thr Trp Thr Glu Ser Gly
                245                 250                 255

Lys Asp Asp Phe Arg Pro Leu Leu Met Ala Trp Trp Pro Asp Thr Glu
                260                 265                 270

Thr Lys Arg Asn Tyr Val Asn Tyr Met Asn Lys Val Val Gly Ile Asp
            275                 280                 285

Lys Thr Tyr Thr Ala Glu Thr Ser Gln Ala Asp Leu Thr Ala Ala Ala
        290                 295                 300

Glu Leu Val Gln Ala Arg Ile Glu Gln Lys Ile Thr Ser Glu Asn Asn
305                 310                 315                 320

Thr Lys Trp Leu Arg Glu Ala Ile Ser Ala Phe Val Lys Thr Gln Pro
                325                 330                 335
```

```
Gln Trp Asn Gly Glu Ser Glu Lys Pro Tyr Asp Asp His Leu Gln Asn
                340                 345                 350

Gly Ala Leu Leu Phe Asp Asn Gln Thr Asp Leu Thr Pro Asp Thr Gln
                355                 360                 365

Ser Asn Tyr Arg Leu Leu Asn Arg Thr Pro Thr Asn Gln Thr Gly Ser
        370                 375                 380

Leu Asp Ser Arg Phe Thr Tyr Asn Pro Asn Asp Pro Leu Gly Gly Tyr
385                 390                 395                 400

Asp Phe Leu Leu Ala Asn Asp Val Asp Asn Ser Asn Pro Val Val Gln
                405                 410                 415

Ala Glu Gln Leu Asn Trp Leu His Tyr Leu Leu Asn Phe Gly Ser Ile
                420                 425                 430

Tyr Ala Asn Asp Ala Asp Ala Asn Phe Asp Ser Ile Arg Val Asp Ala
                435                 440                 445

Val Asp Asn Val Asp Ala Asp Leu Leu Gln Ile Ser Ser Asp Tyr Leu
        450                 455                 460

Lys Ala Ala Tyr Gly Ile Asp Lys Asn Asn Lys Asn Ala Asn Asn His
465                 470                 475                 480

Val Ser Ile Val Glu Ala Trp Ser Asp Asn Asp Thr Pro Tyr Leu His
                485                 490                 495

Asp Asp Gly Asp Asn Leu Met Asn Met Asp Asn Lys Phe Arg Leu Ser
                500                 505                 510

Met Leu Trp Ser Leu Ala Lys Pro Leu Asp Lys Arg Ser Gly Leu Asn
                515                 520                 525

Pro Leu Ile His Asn Ser Leu Val Asp Arg Glu Val Asp Asp Arg Glu
        530                 535                 540

Val Glu Thr Val Pro Ser Tyr Ser Phe Ala Arg Ala His Asp Ser Glu
545                 550                 555                 560

Val Gln Asp Ile Ile Arg Asp Ile Ile Lys Ala Glu Ile Asn Pro Asn
                565                 570                 575

Ser Phe Gly Tyr Ser Phe Thr Gln Glu Glu Ile Glu Gln Ala Phe Lys
                580                 585                 590

Ile Tyr Asn Glu Asp Leu Lys Lys Thr Asp Lys Lys Tyr Thr His Tyr
        595                 600                 605

Asn Val Pro Leu Ser Tyr Thr Leu Leu Leu Thr Asn Lys Gly Ser Ile
        610                 615                 620

Pro Arg Val Tyr Tyr Gly Asp Met Phe Thr Asp Asp Gly Gln Tyr Met
625                 630                 635                 640

Ala Asn Lys Thr Val Asn Tyr Asp Ala Ile Glu Ser Leu Leu Lys Ala
                645                 650                 655

Arg Met Lys Tyr Val Ser Gly Gln Ala Met Gln Asn Tyr Gln Ile
                660                 665                 670

Gly Asn Gly Glu Ile Leu Thr Ser Val Arg Tyr Gly Lys Gly Ala Leu
        675                 680                 685

Lys Gln Ser Asp Lys Gly Asp Ala Thr Thr Arg Thr Ser Gly Val Gly
        690                 695                 700

Val Val Met Gly Asn Gln Pro Asn Phe Ser Leu Asp Gly Lys Val Val
705                 710                 715                 720

Ala Leu Asn Met Gly Ala Ala His Ala Asn Gln Glu Tyr Arg Ala Leu
                725                 730                 735

Met Val Ser Thr Lys Asp Gly Val Ala Thr Tyr Ala Thr Asp Ala Asp
                740                 745                 750

Ala Ser Lys Ala Gly Leu Val Lys Arg Thr Asp Glu Asn Gly Tyr Leu
```

-continued

```
                755                 760                 765
Tyr Phe Leu Asn Asp Asp Leu Lys Gly Val Ala Asn Pro Gln Val Ser
770                 775                 780

Gly Phe Leu Gln Val Trp Val Pro Val Gly Ala Ala Asp Asp Gln Asp
785                 790                 795                 800

Ile Arg Val Ala Ala Ser Asp Thr Ala Ser Thr Asp Gly Lys Ser Leu
                805                 810                 815

His Gln Asp Ala Ala Met Asp Ser Arg Val Met Phe Glu Gly Phe Ser
                820                 825                 830

Asn Phe Gln Ser Phe Ala Thr Lys Glu Glu Tyr Thr Asn Val Val
                835                 840                 845

Ile Ala Asn Asn Val Asp Lys Phe Val Ser Trp Gly Ile Thr Asp Phe
850                 855                 860

Glu Met Ala Pro Gln Tyr Val Ser Ser Thr Asp Gly Gln Phe Leu Asp
865                 870                 875                 880

Ser Val Ile Gln Asn Gly Tyr Ala Phe Thr Asp Arg Tyr Asp Leu Gly
                885                 890                 895

Met Ser Lys Ala Asn Lys Tyr Gly Thr Ala Asp Gln Leu Val Lys Ala
                900                 905                 910

Ile Lys Ala Leu His Ala Lys Gly Leu Lys Val Met Ala Asp Trp Val
                915                 920                 925

Pro Asp Gln Met Tyr Thr Phe Pro Lys Gln Glu Val Val Thr Val Thr
930                 935                 940

Arg Thr Asp Lys Phe Gly Lys Pro Ile Ala Gly Ser Gln Ile Asn His
945                 950                 955                 960

Ser Leu Tyr Val Thr Asp Thr Lys Ser Ser Gly Asp Asp Tyr Gln Ala
                965                 970                 975

Lys Tyr Gly Gly Ala Phe Leu Asp Glu Leu Lys Glu Lys Tyr Pro Glu
                980                 985                 990

Leu Phe Thr Lys Lys Gln Ile Ser  Thr Gly Gln Ala Ile  Asp Pro Ser
                995                 1000                1005

Val Lys  Ile Lys Gln Trp Ser  Ala Lys Tyr Phe Asn  Gly Ser Asn
1010                1015                1020

Ile Leu  Gly Arg Gly Ala Asp  Tyr Val Leu Ser Asp  Gln Val Ser
1025                1030                1035

Asn Lys  Tyr Phe Asn Val Ala  Ser Asp Thr Leu Phe  Leu Pro Ser
1040                1045                1050

Ser Leu  Leu Gly Lys Val Val  Glu Ser Gly Ile Arg  Tyr Asp Gly
1055                1060                1065

Lys Gly  Tyr Ile Tyr Asn Ser  Ser Ala Thr Gly Asp  Gln Val Lys
1070                1075                1080

Ala Ser  Phe Ile Thr Glu Ala  Gly Asn Leu Tyr  Phe Gly Lys
1085                1090                1095

Asp Gly  Tyr Met Val Thr Gly  Ala Gln Thr Ile Asn  Gly Ala Asn
1100                1105                1110

Tyr Phe  Phe Leu Glu Asn Gly  Thr Ala Leu Arg Asn  Thr Ile Tyr
1115                1120                1125

Thr Asp  Ala Gln Gly Asn Ser  His Tyr Tyr Ala Asn  Asp Gly Lys
1130                1135                1140

Arg Tyr  Glu Asn Gly Tyr Gln  Gln Phe Gly Asn Asp  Trp Arg Tyr
1145                1150                1155

Phe Lys  Asp Gly Asn Met Ala  Val Gly Leu Thr Thr  Val Asp Gly
1160                1165                1170
```

-continued

```
Asn Val Gln Tyr Phe Asp Lys Asp Gly Val Gln Ala Lys Asp Lys
    1175                1180                1185

Ile Ile Val Thr Arg Asp Gly Lys Val Arg Tyr Phe Asp Gln His
    1190                1195                1200

Asn Gly Asn Ala Ala Thr Asn Thr Phe Ile Ala Asp Lys Thr Gly
    1205                1210                1215

His Trp Tyr Tyr Leu Gly Lys Asp Gly Val Ala Val Thr Gly Ala
    1220                1225                1230

Gln Thr Val Gly Lys Gln Lys Leu Tyr Phe Glu Ala Asn Gly Gln
    1235                1240                1245

Gln Val Lys Gly Asp Phe Val Thr Ser Asp Glu Gly Lys Leu Tyr
    1250                1255                1260

Phe Tyr Asp Val Asp Ser Gly Asp Met Trp Thr Asp Thr Phe Ile
    1265                1270                1275

Glu Asp Lys Ala Gly Asn Trp Phe Tyr Leu Gly Lys Asp Gly Ala
    1280                1285                1290

Ala Val Thr Gly Ala Gln Thr Ile Arg Gly Gln Lys Leu Tyr Phe
    1295                1300                1305

Lys Ala Asn Gly Gln Gln Val Lys Gly Asp Ile Val Lys Gly Thr
    1310                1315                1320

Asp Gly Lys Ile Arg Tyr Tyr Asp Ala Lys Ser Gly Glu Gln Val
    1325                1330                1335

Phe Asn Lys Thr Val Lys Ala Ala Asp Gly Lys Thr Tyr Val Ile
    1340                1345                1350

Gly Asn Asp Gly Val Ala Val Asp Pro Ser Val Val Lys Gly Gln
    1355                1360                1365

Thr Phe Lys Asp Ala Ser Gly Ala Leu Arg Phe Tyr Asn Leu Lys
    1370                1375                1380

Gly Gln Leu Val Thr Gly Ser Gly Trp Tyr Glu Thr Ala Asn His
    1385                1390                1395

Asp Trp Val Tyr Ile Gln Ser Gly Lys Ala Leu Thr Gly Glu Gln
    1400                1405                1410

Thr Ile Asn Gly Gln His Leu Tyr Phe Lys Glu Asp Gly His Gln
    1415                1420                1425

Val Lys Gly Gln Leu Val Thr Gly Thr Asp Gly Lys Val Arg Tyr
    1430                1435                1440

Tyr Asp Ala Asn Ser Gly Asp Gln Ala Phe Asn Lys Ser Val Thr
    1445                1450                1455

Val Asn Gly Lys Thr Tyr Tyr Phe Gly Asn Asp Gly Thr Ala Gln
    1460                1465                1470

Thr Ala Gly Asn Pro Lys Gly Gln Thr Phe Lys Asp Gly Ser Asp
    1475                1480                1485

Ile Arg Phe Tyr Ser Met Glu Gly Gln Leu Val Thr Gly Ser Gly
    1490                1495                1500

Trp Tyr Glu Asn Ala Gln Gln Trp Leu Tyr Val Lys Asn Gly
    1505                1510                1515

Lys Val Leu Thr Gly Leu Gln Thr Val Gly Ser Gln Arg Val Tyr
    1520                1525                1530

Phe Asp Glu Asn Gly Ile Gln Ala Lys Gly Lys Ala Val Arg Thr
    1535                1540                1545

Ser Asp Gly Lys Ile Arg Tyr Phe Asp Glu Asn Ser Gly Ser Met
    1550                1555                1560
```

```
Ile Thr Asn Gln Trp Lys Phe Val Tyr Gly Gln Tyr Tyr Tyr Phe
    1565            1570                1575

Gly Asn Asp Gly Ala Arg Ile Tyr Arg Gly Trp Asn
    1580            1585            1590

<210> SEQ ID NO 38
<211> LENGTH: 1554
<212> TYPE: PRT
<213> ORGANISM: Streptococcus sobrinus

<400> SEQUENCE: 38

Met Glu Lys Lys Leu His Tyr Lys Leu His Val Lys Lys His Trp
1               5                   10                  15

Val Thr Ile Ala Val Ala Ser Ile Gly Leu Val Ser Leu Val Gly Ala
            20                  25                  30

Gly Thr Val Ser Ala Glu Asp Lys Val Ala Asn Asp Thr Ala Gln
                35                  40                  45

Ala Thr Val Gly Val Asp Thr Gly Gln Asp Gln Ala Thr Thr Asn Asp
    50                  55                  60

Ala Asn Thr Asn Thr Thr Asp Thr Asp Thr Ala Asp Gln Ser Ala Asn
65                  70                  75                  80

Thr Asn Gln Asp Gln Ala Gly Ser Asp Gln Ser Asn Asn Gln Asp Gln
                85                  90                  95

Ala Lys Gln Asp Thr Ala Asn Thr Asp Arg Asn Gln Ala Asp Asn Ser
            100                 105                 110

Gln Thr Asp Asn Asn Gln Ala Thr Asp Gln Ala Thr Ser Pro Ala Thr
        115                 120                 125

Asp Gly Thr Ser Val Gln Arg Arg Asp Ala Ala Asn Val Ala Thr Ala
    130                 135                 140

Ala Asp Gln Glu Gly Gln Thr Ala Pro Ser Glu Gln Glu Lys Ser Ala
145                 150                 155                 160

Ala Leu Ser Leu Asp Asn Val Lys Leu Ile Asp Gly Lys Tyr Tyr Tyr
                165                 170                 175

Val Gln Ala Asp Gly Ser Tyr Lys Lys Asn Phe Ala Ile Thr Val Asn
            180                 185                 190

Gly Gln Met Leu Tyr Phe Asp Ser Asp Thr Gly Ala Leu Ser Ser Thr
        195                 200                 205

Ser Thr Tyr Ser Phe Ser Gln Gly Thr Thr Asn Leu Val Asp Asp Phe
    210                 215                 220

Ser Ser His Asn Lys Ala Tyr Asp Ser Thr Ala Lys Ser Phe Glu Leu
225                 230                 235                 240

Val Asn Gly Tyr Leu Thr Ala Asn Ser Trp Tyr Arg Pro Ala Gly Ile
                245                 250                 255

Leu Arg Asn Gly Gln Thr Trp Glu Ala Ser Asn Glu Asn Asp Leu Arg
            260                 265                 270

Pro Val Leu Met Ser Trp Trp Pro Asp Lys Asp Thr Gln Val Ala Tyr
        275                 280                 285

Val Asn Tyr Met Asn Lys Tyr Leu Ser Ala Asn Glu Thr Glu Val Thr
    290                 295                 300

Asn Glu Thr Ser Gln Val Asp Leu Asn Lys Glu Ala Gln Ser Ile Gln
305                 310                 315                 320

Thr Lys Ile Glu Gln Lys Ile Thr Ser Asp Asn Ser Thr Gln Trp Leu
                325                 330                 335

Arg Thr Ala Met Glu Ala Phe Val Ala Ala Gln Pro Lys Trp Asn Met
            340                 345                 350
```

-continued

```
Ser Thr Glu Asn Phe Asn Lys Gly Asp His Leu Gln Gly Gly Ala Leu
        355                 360                 365
Leu Tyr Thr Asn Ser Asp Leu Thr Pro Trp Ala Asn Ser Asp Tyr Arg
    370                 375                 380
Leu Leu Asn Arg Thr Pro Thr Gln Gln Asp Gly Thr Lys Lys Tyr Phe
385                 390                 395                 400
Thr Glu Gly Gly Glu Gly Tyr Glu Phe Leu Leu Ser Asn Asp Val
                405                 410                 415
Asp Asn Ser Asn Pro Val Val Gln Ala Glu Gln Leu Asn Gln Leu His
            420                 425                 430
Tyr Leu Met Asn Trp Gly Asp Ile Val Met Gly Asp Lys Asp Ala Asn
        435                 440                 445
Phe Asp Gly Val Arg Val Asp Ala Val Asp Asn Val Asn Ala Asp Leu
    450                 455                 460
Leu Gln Val Tyr Ser Asn Tyr Phe Lys Asp Asn Tyr Lys Val Thr Asp
465                 470                 475                 480
Ser Glu Ala Asn Ala Leu Ala His Ile Ser Ile Leu Glu Ala Trp Ser
                485                 490                 495
Leu Asn Asp Asn Gln Tyr Asn Glu Asp Thr Asn Gly Thr Ala Leu Ser
            500                 505                 510
Ile Asp Asn Ser Ser Arg Leu Thr Ser Leu Ala Val Leu Thr Lys Gln
        515                 520                 525
Pro Gly Gln Arg Ile Asp Leu Ser Asn Leu Ile Ser Glu Ser Val Asn
    530                 535                 540
Lys Glu Arg Ala Asn Asp Thr Ala Tyr Gly Asp Thr Ile Pro Thr Tyr
545                 550                 555                 560
Ser Phe Val Arg Ala His Asp Ser Glu Val Gln Thr Val Ile Ala Lys
                565                 570                 575
Ile Val Lys Glu Lys Ile Asp Thr Asn Ser Asp Gly Tyr Thr Phe Thr
            580                 585                 590
Leu Asp Gln Leu Lys Asp Ala Phe Lys Ile Tyr Asn Glu Asp Met Ala
        595                 600                 605
Lys Val Asn Lys Thr Tyr Thr His Tyr Asn Ile Pro Ala Ala Tyr Ala
    610                 615                 620
Leu Leu Leu Ser Asn Met Glu Ser Val Pro Arg Val Tyr Tyr Gly Asp
625                 630                 635                 640
Leu Tyr Thr Asp Asp Gly Gln Tyr Met Ala Lys Lys Ser Pro Tyr Tyr
                645                 650                 655
Asp Ala Ile Ala Thr Met Leu Gln Gly Arg Ile Ala Tyr Val Ser Gly
            660                 665                 670
Gly Gln Ser Glu Glu Val His Lys Val Asn Gly Asn Gln Ile Leu
        675                 680                 685
Ser Ser Val Arg Tyr Gly Gln Asp Leu Met Ser Ala Asp Thr Gln
    690                 695                 700
Gly Thr Asp Leu Ser Arg Thr Ser Gly Leu Val Thr Leu Val Ser Asn
705                 710                 715                 720
Asp Pro Asn Leu Asp Leu Gly Gly Asp Ser Leu Thr Val Asn Met Gly
                725                 730                 735
Arg Ala His Ala Asn Gln Ala Tyr Arg Pro Leu Ile Leu Gly Thr Lys
            740                 745                 750
Asp Gly Val Gln Ser Tyr Leu Lys Asp Ser Asp Thr Asn Ile Val Lys
        755                 760                 765
```

-continued

Tyr Thr Asp Ala Asn Gly Asn Leu Thr Phe Thr Ala Asp Asp Ile Lys
770                 775                 780

Gly Tyr Ser Thr Val Asp Met Ser Gly Tyr Leu Ala Val Trp Val Pro
785                 790                 795                 800

Val Gly Ala Lys Asp Gly Gln Asp Val Arg Val Ala Ala Asp Thr Asn
            805                 810                 815

Gln Lys Ala Asp Gly Lys Ser Leu Lys Thr Ser Ala Ala Leu Asp Ser
            820                 825                 830

Gln Val Ile Tyr Glu Gly Phe Ser Asn Phe Gln Asp Phe Ala Asn Asn
            835                 840                 845

Asp Ala Asp Tyr Thr Asn Lys Lys Ile Ala Glu Asn Ala Asp Phe Phe
850                 855                 860

Lys Lys Leu Gly Ile Thr Ser Phe Glu Met Ala Pro Gln Tyr Val Ser
865                 870                 875                 880

Ala Thr Asp Gly Ser Phe Leu Asp Ser Ile Ile Gln Asn Gly Tyr Ala
            885                 890                 895

Phe Ser Asp Arg Tyr Asp Leu Ala Met Ser Lys Asn Asn Lys Tyr Gly
            900                 905                 910

Ser Lys Asp Asp Leu Ala Asn Ala Leu Lys Ala Leu His Ala Asn Gly
            915                 920                 925

Ile Gln Ala Ile Ala Asp Trp Val Pro Asp Gln Ile Tyr Gln Leu Pro
930                 935                 940

Gly Glu Glu Val Val Thr Ala Lys Arg Thr Asn Ser Tyr Gly Asn Pro
945                 950                 955                 960

Thr Phe Asp Ala Tyr Ile Asn Asn Ala Leu Tyr Ala Thr Asn Thr Lys
            965                 970                 975

Ser Ser Gly Ser Asp Tyr Gln Ala Gln Tyr Gly Gly Ala Phe Leu Asp
            980                 985                 990

Glu Leu Lys Ala Lys Tyr Pro Asp Met Phe Thr Val Asn Met Ile Ser
            995                 1000                1005

Thr Gly Lys Pro Ile Asp Pro Ser Thr Lys Ile Lys Gln Trp Glu
    1010            1015            1020

Ala Lys Tyr Phe Asn Gly Thr Asn Val Leu Gly Lys Gly Ala Gly
    1025            1030            1035

Tyr Val Leu Ser Asp Asp Ala Thr Gly Lys Tyr Phe Thr Val Asn
    1040            1045            1050

Glu Asn Gly Asp Phe Leu Pro Ala Ser Phe Thr Gly Asp Gln Asn
    1055            1060            1065

Ala Lys Thr Gly Phe Tyr Tyr Asp Gly Thr Gly Met Ala Tyr Tyr
    1070            1075            1080

Ser Thr Ser Gly Asn Lys Ala Val Asn Ser Phe Ile Tyr Glu Gly
    1085            1090            1095

Gly His Tyr Tyr Tyr Phe Asp Lys Asp Gly His Met Val Thr Gly
    1100            1105            1110

Ser Tyr Lys Ala Glu Asp Gly Asn Asp Tyr Tyr Phe Leu Pro Asn
    1115            1120            1125

Gly Ile Gln Met Arg Asp Ala Ile Tyr Gln Asp Ala Gln Gly Asn
    1130            1135            1140

Ser Tyr Tyr Tyr Gly Arg Thr Gly Ile Leu Tyr Lys Gly Asp Asn
    1145            1150            1155

Trp Tyr Pro Phe Val Asp Pro Asn Asn Ala Asn Lys Thr Val Phe
    1160            1165            1170

Arg Tyr Phe Asp Ala Asn Asn Val Met Ala Ile Gly Tyr Arg Asn

-continued

```
            1175                1180                1185

Met Tyr Gly Gln Thr Tyr Tyr Phe Asp Glu Asn Gly Phe Gln Ala
    1190                1195                1200

Lys Gly Gln Leu Leu Thr Asp Asp Lys Gly Thr His Tyr Phe Asp
    1205                1210                1215

Glu Asp Asn Gly Ala Met Ala Lys Asn Lys Phe Val Asn Val Gly
    1220                1225                1230

Asp Asp Trp Tyr Tyr Met Asp Gly Asn Gly Asn Ala Val Lys Gly
    1235                1240                1245

Gln Tyr Pro Val Asn Asn Gln Ile Leu Tyr Phe Asn Pro Glu Thr
    1250                1255                1260

Gly Val Gln Val Lys Gly Gln Phe Ile Thr Asp Ala Gln Gly Arg
    1265                1270                1275

Thr Ser Tyr Tyr Asp Ala Asn Ser Gly Ala Leu Lys Ser Ser Gly
    1280                1285                1290

Phe Phe Thr Pro Asn Gly Ser Asp Trp Tyr Tyr Ala Glu Asn Gly
    1295                1300                1305

Tyr Val Tyr Lys Gly Phe Lys Gln Val Ala Glu Asn Gln Asp Gln
    1310                1315                1320

Trp Tyr Tyr Phe Asp Gln Thr Thr Gly Lys Gln Ala Lys Gly Ala
    1325                1330                1335

Ala Lys Val Asp Gly Arg Asp Leu Tyr Phe Asn Pro Asp Ser Gly
    1340                1345                1350

Val Gln Val Lys Gly Asp Phe Ala Thr Asp Glu Ser Gly Asn Thr
    1355                1360                1365

Ser Phe Tyr His Gly Asp Asn Gly Asp Lys Val Val Gly Gly Phe
    1370                1375                1380

Phe Thr Thr Gly Asn Asn Ala Trp Tyr Tyr Ala Asp Asn Asn Gly
    1385                1390                1395

Asn Leu Val Lys Gly Phe Gln Glu Ile Asp Gly Lys Trp Tyr His
    1400                1405                1410

Phe Asp Glu Val Thr Gly Gln Gln Ala Lys Gly Ala Ala Leu Val
    1415                1420                1425

Asn Gly Gln Gln Leu Tyr Phe Asp Val Asp Ser Gly Ile Gln Val
    1430                1435                1440

Lys Gly Asp Phe Val Thr Asp Gly Gln Gly Asn Thr Ser Tyr Tyr
    1445                1450                1455

Asp Val Asn Ser Gly Asp Lys Lys Val Asn Gly Phe Phe Thr Thr
    1460                1465                1470

Gly Asp Asn Ala Trp Tyr Tyr Ala Asp Gly Gln Gly Asn Leu Ala
    1475                1480                1485

Lys Gly Arg Lys Ser Ile Asp Asn Gln Asp Leu Tyr Phe Asp Pro
    1490                1495                1500

Ala Thr Gly Lys Gln Val Lys Gly Gln Leu Val Ser Ile Asp Gly
    1505                1510                1515

Arg Asn Tyr Tyr Phe Asp Ser Gly Ser Gly Asn Met Ala Lys Asn
    1520                1525                1530

Arg Phe Val Arg Ile Gly Asp Gln Trp Ile Tyr Phe Gly Asn Asp
    1535                1540                1545

Gly Ala Ala Thr Asn Leu
    1550
```

<210> SEQ ID NO 39

```
<211> LENGTH: 1365
<212> TYPE: PRT
<213> ORGANISM: Streptococcus downei

<400> SEQUENCE: 39

Met Glu Lys Asn Leu Arg Tyr Lys Leu His Lys Val Lys Lys Gln Trp
1               5                   10                  15

Val Ala Ile Gly Val Thr Thr Val Thr Leu Ser Phe Leu Ala Gly Gly
            20                  25                  30

Gln Val Val Ala Ala Asp Thr Asn Asn Asp Gly Thr Ser Val Gln
        35                  40                  45

Val Asn Lys Met Val Pro Ser Asp Pro Lys Phe Asp Ala Gln Ala Gln
    50                  55                  60

Asn Gly Gln Leu Ala Gln Ala Met Phe Lys Ala Ala Asn Gln Ala Asp
65                  70                  75                  80

Gln Thr Ala Thr Ser Gln Val Ser Pro Ala Thr Asp Gly Arg Val Asp
                85                  90                  95

Asn Gln Val Thr Pro Ala Ala Asn Gln Pro Ala Ala Asn Val Ala Asn
            100                 105                 110

Gln Asp Val Ala Asn Pro Ala Thr Asp Ala Gly Ala Leu Asn Arg Gln
        115                 120                 125

Ser Ala Ala Asp Thr Ser Thr Asp Gly Lys Ala Val Pro Gln Thr Ser
130                 135                 140

Asp Gln Pro Gly His Leu Glu Thr Val Asp Gly Lys Thr Tyr Tyr Val
145                 150                 155                 160

Asp Ala Asn Gly Gln Arg Leu Lys Asn Tyr Ser Met Val Ile Asp Gly
                165                 170                 175

Lys Thr Tyr Tyr Phe Asp Gly Gln Thr Gly Glu Ala Gln Thr Asp Leu
            180                 185                 190

Pro Lys Thr Gly Gln Ala Asn Gln Asp Asn Val Pro Asp Ser Tyr Gln
        195                 200                 205

Ala Asn Asn Gln Ala Tyr Ser Asn Glu Ala Ser Ser Phe Glu Thr Val
    210                 215                 220

Asp Asn Tyr Leu Thr Ala Asp Ser Trp Tyr Arg Pro Arg Lys Ile Leu
225                 230                 235                 240

Lys Asn Gly Gln Ser Trp Gln Ala Ser Ser Glu Gly Asp Leu Arg Pro
                245                 250                 255

Ile Leu Met Thr Trp Trp Pro Asp Ala Ala Thr Lys Ala Ala Tyr Ala
            260                 265                 270

Asn Phe Trp Ala Lys Glu Gly Leu Ile Ser Gly Ser Tyr Arg Gln Asn
        275                 280                 285

Ser Ala Asn Leu Asp Ala Ala Thr Gln Asn Ile Gln Ser Ala Ile Glu
    290                 295                 300

Lys Lys Ile Ala Ser Glu Gly Asn Thr Asn Trp Leu Arg Asp Lys Met
305                 310                 315                 320

Ser Gln Phe Val Lys Ser Gln Asn Gln Trp Ser Ile Ala Ser Glu Asn
                325                 330                 335

Glu Thr Val Tyr Pro Asn Gln Asp His Met Gln Gly Gly Ala Leu Leu
            340                 345                 350

Phe Ser Asn Ser Lys Asp Thr Glu His Ala Asn Ser Asp Trp Arg Leu
        355                 360                 365

Leu Asn Arg Asn Pro Thr Phe Gln Gly Lys Gln Lys Tyr Phe Thr
    370                 375                 380

Thr Asn Tyr Ala Gly Tyr Glu Leu Leu Leu Ala Asn Asp Val Asp Asn
```

-continued

```
            385                 390                 395                 400
Ser Asn Pro Val Val Gln Ala Glu Gln Leu Asn His Leu His Tyr Leu
            405                 410                 415
Met Asn Trp Gly Asp Ile Val Met Gly Asp Lys Asp Ala Asn Phe Asp
            420                 425                 430
Gly Val Arg Val Asp Ala Val Asp Asn Val Asn Ala Asp Leu Leu Gln
            435                 440                 445
Ile Gln Arg Asp Tyr Tyr Lys Ala Lys Tyr Gly Thr Asp Gln Asn Glu
            450                 455                 460
Lys Asn Ala Ile Asp His Leu Ser Ile Leu Glu Ala Trp Ser Gly Asn
465                 470                 475                 480
Asp Asn Asp Tyr Val Lys Asp Gln Asn Asn Phe Ser Leu Ser Ile Asp
            485                 490                 495
Asn Asp Gln Arg Ser Gly Met Leu Lys Ala Phe Gly Tyr Ala Ser Ala
            500                 505                 510
Tyr Arg Gly Asn Leu Ser Asn Leu Ala Thr Ala Gly Leu Lys Asn Arg
            515                 520                 525
Ser Ala Asn Pro Asp Ser Asp Pro Val Pro Asn Tyr Val Phe Ile Arg
530                 535                 540
Ala His Asp Ser Glu Val Gln Thr Arg Ile Ala Lys Ile Ile Arg Glu
545                 550                 555                 560
Lys Leu Gly Lys Thr Asn Ala Asp Gly Leu Thr Asn Leu Thr Leu Asp
            565                 570                 575
Asp Leu Asn Lys Ala Phe Asp Ile Tyr Asn Gln Asp Met Asn Ala Thr
            580                 585                 590
Asp Lys Val Tyr Tyr Pro Asn Asn Leu Pro Met Ala Tyr Ala Trp Met
            595                 600                 605
Leu Gln Asn Lys Asp Thr Val Thr Arg Val Tyr Tyr Gly Asp Met Tyr
            610                 615                 620
Thr Asp Asn Gly Gln Tyr Met Ala Thr Lys Thr Pro Phe Tyr Asn Ala
625                 630                 635                 640
Ile Glu Thr Leu Leu Lys Gly Arg Ile Lys Tyr Val Ala Gly Gly Gln
            645                 650                 655
Ala Val Ser Tyr Lys Gln Asp Trp Ser Ser Gly Ile Leu Thr Ser Val
            660                 665                 670
Arg Tyr Gly Lys Gly Ala Asn Ser Ala Ser Asp Ala Gly Asn Thr Glu
            675                 680                 685
Thr Arg Asn Ser Gly Met Ala Leu Leu Ile Asn Asn Arg Pro Asn Phe
            690                 695                 700
Arg Ala Tyr Arg Asn Leu Thr Leu Asn Met Gly Ala Ala His Lys Ser
705                 710                 715                 720
Gln Ala Tyr Arg Pro Leu Leu Leu Ser Thr Lys Asp Gly Ile Ala Thr
            725                 730                 735
Tyr Leu Asn Asp Ser Asp Val Asp Ser Arg Gln Tyr Lys Tyr Thr Asp
            740                 745                 750
Ser Gln Gly Asn Leu Ser Phe Ser Ala Ser Glu Leu Gln Ser Val Ala
            755                 760                 765
Asn Ala Gln Val Ser Gly Met Ile Gln Val Trp Val Pro Val Gly Ala
            770                 775                 780
Ala Asp Asn Gln Asp Val Arg Thr Ser Pro Ser Thr Gln Ala Thr Lys
785                 790                 795                 800
Asp Gly Asn Ile Tyr His Gln Ser Asp Ala Leu Asp Ser Gln Val Ile
            805                 810                 815
```

-continued

```
Tyr Glu Gly Phe Ser Asn Phe Gln Ala Phe Ala Gln Ser Pro Asp Gln
            820                 825                 830

Tyr Thr Asn Ala Val Ile Ala Lys Asn Gly Asp Leu Phe Lys Ser Trp
            835                 840                 845

Gly Ile Thr Gln Phe Glu Met Ala Pro Gln Tyr Val Ser Ser Glu Asp
            850                 855                 860

Gly Thr Phe Leu Asp Ser Val Ile Leu Asn Gly Tyr Ala Phe Ser Asp
865                 870                 875                 880

Arg Tyr Asp Leu Ala Met Ser Lys Asn Lys Tyr Gly Ser Lys Gln
                    885                 890                 895

Asp Leu Ala Asn Ala Ile Lys Gly Leu Gln Ser Ala Gly Ile Lys Val
                900                 905                 910

Leu Ser Asp Leu Val Pro Asn Gln Leu Tyr Asn Leu Pro Gly Lys Glu
            915                 920                 925

Val Val Thr Ala Thr Arg Val Asn Gln Tyr Gly Gln Ala Lys Ser Gly
            930                 935                 940

Ala Thr Ile Asn Lys Thr Pro Tyr Val Ala Asn Thr Arg Ser Tyr Gly
945                 950                 955                 960

Asp Tyr Gln Glu Gln Tyr Gly Gly Lys Phe Leu Asp Leu Gln Lys
                    965                 970                 975

Leu Tyr Pro Arg Leu Phe Ser Thr Lys Gln Ile Ser Thr Gly Lys Pro
            980                 985                 990

Ile Asp Pro Ser Val Lys Ile Thr Asn Trp Ser Ala Lys Tyr Phe Asn
            995                 1000                1005

Gly Ser Asn Ile Leu Gly Arg Gly Ala Lys Tyr Val Leu Ser Glu
            1010                1015                1020

Gly Asn Lys Tyr Leu Asn Leu Ala Asp Gly Lys Leu Phe Leu Pro
            1025                1030                1035

Thr Val Leu Asn Asn Thr Tyr Gly Gln Pro Gln Val Ser Ala Asn
            1040                1045                1050

Gly Phe Ile Ser Lys Asn Gly Gly Ile His Tyr Leu Asp Lys Asn
            1055                1060                1065

Gly Gln Glu Val Lys Asn Arg Phe Lys Glu Ile Ser Gly Ser Trp
            1070                1075                1080

Tyr Tyr Phe Asp Ser Asp Gly Lys Met Ala Thr Gly Lys Thr Lys
            1085                1090                1095

Ile Gly Asn Asp Thr Tyr Leu Phe Met Pro Asn Gly Lys Gln Leu
            1100                1105                1110

Lys Glu Gly Val Trp Tyr Asp Gly Lys Lys Ala Tyr Tyr Tyr Asp
            1115                1120                1125

Asp Asn Gly Arg Thr Trp Thr Asn Lys Gly Phe Val Glu Phe Arg
            1130                1135                1140

Val Asp Gly Gln Asp Lys Trp Arg Tyr Phe Asn Gly Asp Gly Thr
            1145                1150                1155

Ile Ala Ile Gly Leu Val Ser Leu Asp Asn Arg Thr Leu Tyr Phe
            1160                1165                1170

Asp Ala Tyr Gly Tyr Gln Val Lys Gly Gln Thr Val Thr Ile Asn
            1175                1180                1185

Gly Lys Ser Tyr Thr Phe Asp Ala Asp Gln Gly Asp Leu Val Gln
            1190                1195                1200

Thr Asp Asn Ala Asn Pro Ala Pro Gln Gly Gln Ala Gly Trp Lys
            1205                1210                1215
```

```
Leu Leu Gly Asp Asn Gln Trp Gly Tyr Arg Lys Asp Gly Gln Leu
1220                1225                1230

Leu Thr Gly Glu Gln Thr Ile Asp Gly Gln Lys Val Phe Phe Gln
    1235                1240                1245

Asp Asn Gly Val Gln Val Lys Gly Gly Thr Ala Thr Asp Ala Ser
1250                1255                1260

Gly Val Leu Arg Phe Tyr Arg Asp Gln Gly His Gln Val Gly
    1265                1270                1275

Lys Gly Trp Tyr Ser Thr Ser Asp Asp Asn Trp Val Tyr Val Asn
    1280                1285                1290

Glu Ser Gly Gln Val Leu Thr Gly Leu Gln Thr Ile Asp Gly Gln
    1295                1300                1305

Thr Val Tyr Phe Asp Asp Lys Gly Ile Gln Ala Lys Gly Lys Ala
    1310                1315                1320

Val Trp Asp Glu Asn Gly Asn Leu Arg Tyr Phe Asp Ala Asp Ser
1325                1330                1335

Gly Asn Met Leu Arg Asp Arg Trp Lys Asn Val Asp Gly Asn Trp
    1340                1345                1350

Tyr Tyr Phe Asn Arg Asn Gly Leu Ala Thr Arg Trp
    1355                1360                1365

<210> SEQ ID NO 40
<211> LENGTH: 1518
<212> TYPE: PRT
<213> ORGANISM: Streptococcus salivarius

<400> SEQUENCE: 40

Met Glu Asn Lys Ile His Tyr Lys Leu His Lys Val Lys Lys Gln Trp
1               5                   10                  15

Val Thr Ile Ala Val Ala Ser Val Ala Leu Ala Thr Val Leu Gly Gly
                20                  25                  30

Leu Ser Val Thr Thr Ser Ser Val Ser Ala Asp Glu Thr Gln Asp Lys
            35                  40                  45

Thr Val Thr Gln Ser Asn Ser Gly Thr Thr Ala Ser Leu Val Thr Ser
        50                  55                  60

Pro Glu Ala Thr Lys Glu Ala Asp Lys Arg Thr Asn Thr Lys Glu Ala
65                  70                  75                  80

Asp Val Leu Thr Pro Ala Lys Glu Thr Asn Ala Val Glu Thr Ala Thr
                85                  90                  95

Thr Thr Asn Thr Gln Ala Thr Ala Glu Ala Ala Thr Thr Ala Thr Thr
            100                 105                 110

Ala Asp Val Ala Val Ala Val Pro Asn Lys Glu Ala Val Val Thr
        115                 120                 125

Thr Asp Ala Pro Ala Val Thr Thr Glu Lys Ala Glu Glu Gln Pro Ala
    130                 135                 140

Thr Val Lys Ala Glu Val Val Asn Thr Glu Val Lys Ala Pro Glu Ala
145                 150                 155                 160

Ala Leu Lys Asp Ser Glu Val Glu Ala Ala Leu Ser Leu Lys Asn Ile
                165                 170                 175

Lys Asn Ile Asp Gly Lys Tyr Tyr Val Asn Glu Asp Gly Ser His
            180                 185                 190

Lys Glu Asn Phe Ala Ile Thr Val Asn Gly Gln Leu Leu Tyr Phe Gly
        195                 200                 205

Lys Asp Gly Ala Leu Thr Ser Ser Ser Thr Tyr Ser Phe Thr Pro Gly
    210                 215                 220
```

```
Thr Thr Asn Ile Val Asp Gly Phe Ser Ile Asn Asn Arg Ala Tyr Asp
225                 230                 235                 240

Ser Ser Glu Ala Ser Phe Glu Leu Ile Asp Gly Tyr Leu Thr Ala Asp
            245                 250                 255

Ser Trp Tyr Arg Pro Ala Ser Ile Ile Lys Asp Gly Val Thr Trp Gln
            260                 265                 270

Ala Ser Thr Ala Glu Asp Phe Arg Pro Leu Leu Met Ala Trp Trp Pro
            275                 280                 285

Asn Val Asp Thr Gln Val Asn Tyr Leu Asn Tyr Met Ser Lys Val Phe
290                 295                 300

Asn Leu Asp Ala Lys Tyr Ser Ser Thr Asp Lys Gln Glu Thr Leu Lys
305                 310                 315                 320

Val Ala Ala Lys Asp Ile Gln Ile Lys Ile Glu Gln Lys Ile Gln Ala
            325                 330                 335

Glu Lys Ser Thr Gln Trp Leu Arg Glu Thr Ile Ser Ala Phe Val Lys
            340                 345                 350

Thr Gln Pro Gln Trp Asn Lys Glu Thr Glu Asn Tyr Ser Lys Gly Gly
            355                 360                 365

Gly Glu Asp His Leu Gln Gly Gly Ala Leu Leu Tyr Val Asn Asp Ser
            370                 375                 380

Arg Thr Pro Trp Ala Asn Ser Asp Tyr Arg Arg Leu Asn Arg Thr Ala
385                 390                 395                 400

Thr Asn Gln Thr Gly Thr Ile Asp Lys Ser Ile Leu Asp Glu Gln Ser
            405                 410                 415

Asp Pro Asn His Met Gly Gly Phe Asp Phe Leu Leu Ala Asn Asp Val
            420                 425                 430

Asp Leu Ser Asn Pro Val Val Gln Ala Glu Gln Leu Asn Gln Ile His
            435                 440                 445

Tyr Leu Met Asn Trp Gly Ser Ile Val Met Gly Asp Lys Asp Ala Asn
450                 455                 460

Phe Asp Gly Ile Arg Val Asp Ala Val Asp Asn Val Asp Ala Asp Met
465                 470                 475                 480

Leu Gln Leu Tyr Thr Asn Tyr Phe Arg Glu Tyr Tyr Gly Val Asn Lys
            485                 490                 495

Ser Glu Ala Asn Ala Leu Ala His Ile Ser Val Leu Glu Ala Trp Ser
            500                 505                 510

Leu Asn Asp Asn His Tyr Asn Asp Lys Thr Asp Gly Ala Ala Leu Ala
            515                 520                 525

Met Glu Asn Lys Gln Arg Leu Ala Leu Leu Phe Ser Leu Ala Lys Pro
530                 535                 540

Ile Lys Glu Arg Thr Pro Ala Val Ser Pro Leu Tyr Asn Asn Thr Phe
545                 550                 555                 560

Asn Thr Thr Gln Arg Asp Glu Lys Thr Asp Trp Ile Asn Lys Asp Gly
            565                 570                 575

Ser Lys Ala Tyr Asn Glu Asp Gly Thr Val Lys Gln Ser Thr Ile Gly
            580                 585                 590

Lys Tyr Asn Glu Lys Tyr Gly Asp Ala Ser Gly Asn Tyr Val Phe Ile
            595                 600                 605

Arg Ala His Asp Asn Asn Val Gln Asp Ile Ile Ala Glu Ile Ile Lys
            610                 615                 620

Lys Glu Ile Asn Pro Lys Ser Asp Gly Phe Thr Ile Thr Asp Ala Glu
625                 630                 635                 640
```

-continued

```
Met Lys Gln Ala Phe Glu Ile Tyr Asn Lys Asp Met Leu Ser Ser Asp
            645                 650                 655

Lys Lys Tyr Thr Leu Asn Asn Ile Pro Ala Ala Tyr Ala Val Met Leu
            660                 665                 670

Gln Asn Met Glu Thr Ile Thr Arg Val Tyr Tyr Gly Asp Leu Tyr Thr
            675                 680                 685

Asp Asp Gly His Tyr Met Glu Thr Lys Ser Pro Tyr Tyr Asp Thr Ile
690                 695                 700

Val Asn Leu Met Lys Ser Arg Ile Lys Tyr Val Ser Gly Gly Gln Ala
705                 710                 715                 720

Gln Arg Ser Tyr Trp Leu Pro Thr Asp Gly Lys Met Asp Asn Ser Asp
            725                 730                 735

Val Glu Leu Tyr Arg Thr Asn Glu Val Tyr Thr Ser Val Arg Tyr Gly
            740                 745                 750

Lys Asp Ile Met Thr Ala Asn Asp Thr Glu Gly Ser Lys Tyr Ser Arg
            755                 760                 765

Thr Ser Gly Gln Val Thr Leu Val Ala Asn Asn Pro Lys Leu Asn Leu
770                 775                 780

Asp Gln Ser Ala Lys Leu Asn Val Glu Met Gly Lys Ile His Ala Asn
785                 790                 795                 800

Gln Lys Tyr Arg Ala Leu Ile Val Gly Thr Ala Asp Gly Ile Lys Asn
            805                 810                 815

Phe Thr Ser Asp Ala Asp Ala Ile Ala Ala Gly Tyr Val Lys Glu Thr
            820                 825                 830

Asp Ser Asn Gly Val Leu Thr Phe Gly Ala Asn Asp Ile Lys Gly Tyr
835                 840                 845

Glu Thr Phe Asp Met Ser Gly Phe Val Ala Val Trp Val Pro Val Gly
850                 855                 860

Ala Ser Asp Asn Gln Asp Ile Arg Val Ala Pro Ser Thr Glu Ala Lys
865                 870                 875                 880

Lys Glu Gly Glu Leu Thr Leu Lys Ala Thr Glu Ala Tyr Asp Ser Gln
            885                 890                 895

Leu Ile Tyr Glu Gly Phe Ser Asn Phe Gln Thr Ile Pro Asp Gly Ser
            900                 905                 910

Asp Pro Ser Val Tyr Thr Asn Arg Lys Ile Ala Glu Asn Val Asp Leu
            915                 920                 925

Phe Lys Ser Trp Gly Val Thr Ser Phe Glu Met Ala Pro Gln Phe Val
930                 935                 940

Ser Ala Asp Asp Gly Thr Phe Leu Asp Ser Val Ile Gln Asn Gly Tyr
945                 950                 955                 960

Ala Phe Ala Asp Arg Tyr Asp Leu Ala Met Ser Lys Asn Asn Lys Tyr
            965                 970                 975

Gly Ser Lys Glu Asp Leu Arg Asp Ala Leu Lys Ala Leu His Lys Ala
            980                 985                 990

Gly Ile Gln Ala Ile Ala Asp Trp Val Pro Asp Gln Ile Tyr Gln Leu
            995                 1000                1005

Pro Gly Lys Glu Val Val Thr Ala Thr Arg Thr Asp Gly Ala Gly
            1010                1015                1020

Arg Lys Ile Ala Asp Ala Ile Ile Asp His Ser Leu Tyr Val Ala
            1025                1030                1035

Asn Ser Lys Ser Ser Gly Lys Asp Tyr Gln Ala Lys Tyr Gly Gly
            1040                1045                1050

Glu Phe Leu Ala Glu Leu Lys Ala Lys Tyr Pro Glu Met Phe Lys
```

-continued

```
                1055                1060                1065
Val Asn Met Ile Ser Thr Gly Lys Pro Ile Asp Asp Ser Val Lys
    1070                1075                1080
Leu Lys Gln Trp Lys Ala Glu Tyr Phe Asn Gly Thr Asn Val Leu
    1085                1090                1095
Glu Arg Gly Val Gly Tyr Val Leu Ser Asp Glu Ala Thr Gly Lys
    1100                1105                1110
Tyr Phe Thr Val Thr Lys Glu Gly Asn Phe Ile Pro Leu Gln Leu
    1115                1120                1125
Thr Gly Lys Glu Lys Val Ile Thr Gly Phe Ser Ser Asp Gly Lys
    1130                1135                1140
Gly Ile Thr Tyr Phe Gly Thr Ser Gly Thr Gln Ala Lys Ser Ala
    1145                1150                1155
Phe Val Thr Phe Asn Gly Asn Thr Tyr Tyr Phe Asp Ala Arg Gly
    1160                1165                1170
His Met Val Thr Asn Ser Glu Tyr Ser Pro Asn Gly Lys Asp Val
    1175                1180                1185
Tyr Arg Phe Leu Pro Asn Gly Ile Met Leu Ser Asn Ala Phe Tyr
    1190                1195                1200
Ile Asp Ala Asn Gly Asn Thr Tyr Leu Tyr Asn Ser Lys Gly Gln
    1205                1210                1215
Met Tyr Lys Gly Gly Tyr Thr Lys Phe Asp Val Ser Glu Thr Asp
    1220                1225                1230
Lys Asp Gly Lys Glu Ser Lys Val Val Lys Phe Arg Tyr Phe Thr
    1235                1240                1245
Asn Glu Gly Val Met Ala Lys Gly Val Thr Val Ile Asp Gly Phe
    1250                1255                1260
Thr Gln Tyr Phe Gly Glu Asp Gly Phe Gln Ala Lys Asp Lys Leu
    1265                1270                1275
Val Thr Phe Lys Gly Lys Thr Tyr Tyr Phe Asp Ala His Thr Gly
    1280                1285                1290
Asn Gly Ile Lys Asp Thr Trp Arg Asn Ile Asn Gly Lys Trp Tyr
    1295                1300                1305
Tyr Phe Asp Ala Asn Gly Val Ala Ala Thr Gly Ala Gln Val Ile
    1310                1315                1320
Asn Gly Gln Lys Leu Tyr Phe Asn Glu Asp Gly Ser Gln Val Lys
    1325                1330                1335
Gly Gly Val Val Lys Asn Ala Asp Gly Thr Tyr Ser Lys Tyr Lys
    1340                1345                1350
Glu Gly Phe Gly Glu Leu Val Thr Asn Glu Phe Phe Thr Thr Asp
    1355                1360                1365
Gly Asn Val Trp Tyr Tyr Ala Gly Ala Asn Gly Lys Thr Val Thr
    1370                1375                1380
Gly Ala Gln Val Ile Asn Gly Gln His Leu Tyr Phe Asn Ala Asp
    1385                1390                1395
Gly Ser Gln Val Lys Gly Gly Val Val Lys Asn Ala Asp Gly Thr
    1400                1405                1410
Tyr Ser Lys Tyr Asn Ala Ser Thr Gly Glu Arg Leu Thr Asn Glu
    1415                1420                1425
Phe Phe Thr Thr Gly Asp Asn Asn Trp Tyr Tyr Ile Gly Ala Asn
    1430                1435                1440
Gly Lys Ser Val Thr Gly Glu Val Lys Ile Gly Asp Asp Thr Tyr
    1445                1450                1455
```

```
Phe Phe Ala Lys Asp Gly Lys Gln Val Lys Gly Gln Thr Val Ser
    1460            1465            1470

Ala Gly Asn Gly Arg Ile Ser Tyr Tyr Tyr Gly Asp Ser Gly Lys
    1475            1480            1485

Arg Ala Val Ser Thr Trp Ile Glu Ile Gln Pro Gly Val Tyr Val
    1490            1495            1500

Tyr Phe Asp Lys Asn Gly Leu Ala Tyr Pro Pro Arg Val Leu Asn
    1505            1510            1515

<210> SEQ ID NO 41
<211> LENGTH: 20
<212> TYPE: PRT
<213> ORGANISM: Streptococcus mutans

<400> SEQUENCE: 41

Gly Asn Tyr Trp Gly Asn Gly Gly Gln Trp Ala Ala Ser Ala Ala Ala
1               5                   10                  15

Ala Gly Arg Tyr
            20
```